US012648719B2

(12) United States Patent
Subramaniam et al.

(10) Patent No.: US 12,648,719 B2
(45) Date of Patent: Jun. 9, 2026

(54) METHODS AND APPARATUS FOR MAKING A DETERMINATION ABOUT A PRESENCE OR AN ABSENCE OF A PARASITE IN A BLOOD SAMPLE

(71) Applicant: Ohio State Innovation Foundation, Columbus, OH (US)

(72) Inventors: Vishwanath Subramaniam, Toronto (CA); Mark Drew, Upper Arlington, OH (US); Jonathan Kadowaki, Chardon, OH (US); Travis Jones, Columbus, OH (US); Joseph West, Richwood, OH (US); Marcel Yotebieng, Mamaroneck, NY (US); Shaurya Prakash, Columbus, OH (US); Alexander Scarmuzzi, Dublin, OH (US); Redi Llapi, Mason, OH (US); Jack Crowley, Shaker Heights, OH (US); Sandra Metzler, West Jefferson, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 1135 days.

(21) Appl. No.: 17/614,879

(22) PCT Filed: May 29, 2020

(86) PCT No.: PCT/US2020/035095

§ 371 (c)(1),
(2) Date: Nov. 29, 2021

(87) PCT Pub. No.: WO2020/243413

PCT Pub. Date: Dec. 3, 2020

(65) Prior Publication Data

US 2022/0218242 A1 Jul. 14, 2022

Related U.S. Application Data

(60) Provisional application No. 62/854,100, filed on May 29, 2019, provisional application No. 62/854,108, filed on May 29, 2019.

(51) Int. Cl.
*A61B 5/145* (2006.01)
*A61B 5/00* (2006.01)
*G16H 50/20* (2018.01)

(52) U.S. Cl.
CPC ........ *A61B 5/14546* (2013.01); *A61B 5/0022* (2013.01); *A61B 5/6898* (2013.01); *A61B 5/7264* (2013.01); *G16H 50/20* (2018.01)

(58) Field of Classification Search
CPC . A61B 5/14546; A61B 5/0022; A61B 5/6898; A61B 5/7264; G16H 50/20; Y02A 50/30
See application file for complete search history.

(56) References Cited

U.S. PATENT DOCUMENTS

2012/0169863 A1 7/2012 Bachelet et al.
2020/0023359 A1* 1/2020 Ezra .................. B01L 3/502715

FOREIGN PATENT DOCUMENTS

WO WO-2013071365 A1 * 5/2013 ........... A61K 31/343

OTHER PUBLICATIONS

Nam et al., Magnetic Separation of Malaria-Infected Red Blood Cells in Various Developmental Stages, 2013, American Chemical Society, 85, 7316-7323. (Year: 2013).*

(Continued)

*Primary Examiner* — Kathryn Elizabeth Limbaugh
(74) *Attorney, Agent, or Firm* — Meunier Carlin & Curfman LLC

(57) ABSTRACT

Disclosed herein are methods and apparatus for making a determination whether a blood sample is, or is not, infected with a malaria parasite. The determination is made using a (Continued)

trained machine-learning (ML) algorithm. In some aspects, a microfluidic chip is used for the concentration of red blood cells infected with these parasites from uninfected red blood cells, the staining of the blood sample which differentially stains infected and uninfected red blood cells, and holds the sample of interest for imaging. The microfluidic chip is inserted into an optical subsystem that magnifies the image created from transmitted light microscopy. The magnified image is captured with a camera, and a trained ML algorithm assesses if the sample does or does not contain the parasite. Generally, the ML algorithm is executed on a portable computing device such as a smartphone.

15 Claims, 60 Drawing Sheets

(56) References Cited

OTHER PUBLICATIONS

Wikipedia, Smartphone, Nov. 4, 2017, https://web.archive.org/web/20171104093234/https://en.wikipedia.org/wiki/Smartphone. (Year: 2017).*

International Search Report and Written Opinion, issued by the International Searching Authority (ISA/US) in PCT Application No. 2020/035095 on Oct. 19, 2020. 12 pages.

Rajaraman, S., et al. "Understanding the learned behavior of customized convolutional neural networks toward malaria parasite detection in thin blood smear images." Journal of Medical Imaging 5.3 (2018): 034501. 11 pages.

'Smartphone', Wikipedia, 2015. Retrieved from <https://en.wikipedia.org/wiki/Smartphone> on Aug. 11, 2020. 54 pages.

Poostchi, M., et al. "Image analysis and machine learning for detecting malaria." Transl Res. Apr. 2018; 194:36-55. doi: 10.1016/j.trsl.2017.12.004.

* cited by examiner

Acquire An Image Of A Stained Blood Sample
702

Analyze The Image Using A Trained Machine-Learning
(ML) Algorithm
704

Determine A Presence Or An Absence Of A Malaria
Parasite In The Blood Sample Based On The Analysis Of
The Image Of The Blood Sample Using The Trained ML
Algorithm
706

METHODS AND APPARATUS FOR MAKING A DETERMINATION ABOUT A PRESENCE OR AN ABSENCE OF A PARASITE IN A BLOOD SAMPLE

CROSS-REFERENCE TO RELATED APPLICATIONS

This application is a national stage application filed under 35 U.S.C. § 371 of PCT/US2020/035095 filed May 29, 2020, which claims priority to and benefit of U.S. provisional patent application Ser. No. 62/854,100 filed May 29, 2019, and U.S. provisional patent application Ser. No. 62/854,108 filed May 29, 2019, both of which are fully incorporated by reference and made a part hereof.

BACKGROUND

Malaria affects 40% of the world's population, resulting in 300 to 500 million new infections yearly. Of the different human malarias, *Plasmodium falciparum* (PF) is the most deadly parasite, but is curable if detected. There are two commonly used techniques for assessing a patient's blood for the presence of the malaria parasite, blood smear microscopy and rapid diagnostic tests (RDTs).

Presently the gold standard for diagnosis in the field is through a peripheral blood draw and microscopic analysis by an experienced pathologist. Blood smear microscopy is an accurate and reliable diagnostic test for malaria, but it requires a properly maintained microscope and the expertise of a trained technician or clinician. The materials needed for these tests, along with the labor cost of a trained operator, make it relatively expensive, and the infrastructure makes it often an inaccessible process. Frequently, physicians will administer antimalarial treatments to patients prior to the test results which is a concern regarding over-administration antimalarial therapeutics which contributes to development of resistant parasite strains.

RDT systems derive their value from the low expense-per-test and improved accessibility that they afford due to their ease-of-shipment. The downsides of this method are the thermal instability of the buffers and stain compounds, which demands refrigeration, and the poor performance in terms of accuracy when the RDTs are used outside of a clinical setting. Because the results are unreliable, physicians often prescribe anti-malarial medication regardless of RDT assessment, which again contributes to developing drug resistance.

Although non-invasive diagnostics that do not require a blood draw remain a sought after solution to this global problem, a more presently attainable goal is a diagnostic device that is inexpensive, improves the diagnostic accuracy, and either improves the diagnostic accuracy of a pathologist's diagnosis or eliminates the need for an optical microscope and a well-trained microscopist or pathologist altogether Therefore, methods, apparatus and systems are desired that overcome challenges in the art, some of which are described above.

SUMMARY

Described herein are devices and methods to analyze a blood sample and make a determination whether the sample is, or is not, infected with a malaria parasite. In this disclosure, devices and methods are described that take advantage of rapid technological development in three different areas; widespread availability of smart cell phones, availability of open source machine learning algorithms and codes, and 3-D printing, to provide a malaria diagnostic system. For example, an individual user with a smartphone equipped with the described Machine Learning (ML) application (App) is used to analyze blood samples.

In contrast to blood smear microscopy, the disclosed systems and methods have inexpensive components and are designed to be performed by any consumer, without the need for a trained operator. The machine learning component replaces the role of a trained operator. In contrast to conventional RDT technology, the disclosed systems and methods have a comparable cost-per-test to the RDT systems in use today and provide rapid assessment of ill patients with malaria-like symptoms in endemic areas and the mitigation of developing drug resistance that is accelerated by over-administration of antimalarial medication.

In some instances, a cell phone camera attachment (somewhat similar to the 3-D printed smartphone microscope described by the Pacific Northwest National Laboratory (PNNL) at https://availabletechnologies.pnnl.gov/technology.aso?id=393, incorporated by reference, and shown in FIG. 1A) is used to image a blood sample that is produced with a disposable lancet-equipped chip (also outfitted with a built-in reservoir that contains a parasite-selective stain) such as the one shown in FIG. 1B. The ML app then analyzes the blood sample and in the local language or through an indicator such as a red or green light that displays on the display of the smartphone or another associated display, indicates whether or not the malaria parasite is detected. In some instances, the disclosed methods and devices can assist existing microscopists or pathologists in the field by reducing the number of false negatives due to inadequate microscope maintenance, blood-sample quality, and human fatigue.

In other instances, microfluidic technologies are used with machine learning to create a powerful, easy to use diagnostic platform. The microfluidic platform concentrates the parasite-infected red blood cells concentrations, affording lower power magnification, affordable optical equipment, and increased sensitivity. The artificial intelligence (AI) analysis and diagnosis relieves the need for clinicians who are necessary for the current 'gold-standard' smear microscopy diagnoses.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure.

As used in the specification and the appended claims, the singular forms “a,” “an” and “the” include plural referents unless the context clearly dictates otherwise. Ranges may be expressed herein as from “about” one particular value, and/or to “about” another particular value. When such a range is expressed, another embodiment includes from the one particular value and/or to the other particular value. Similarly, when values are expressed as approximations, by use of the antecedent “about,” it will be understood that the particular value forms another embodiment. It will be further understood that the endpoints of each of the ranges are significant both in relation to the other endpoint, and independently of the other endpoint.

“Optional” or “optionally” means that the subsequently described event or circumstance may or may not occur, and that the description includes instances where said event or circumstance occurs and instances where it does not.

Throughout the description and claims of this specification, the word “comprise” and variations of the word, such as “comprising” and “comprises,” means “including but not limited to,” and is not intended to exclude, for example, other additives, components, integers or steps. “Exemplary” means “an example of” and is not intended to convey an indication of a preferred or ideal embodiment. “Such as” is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

Figure 1B:
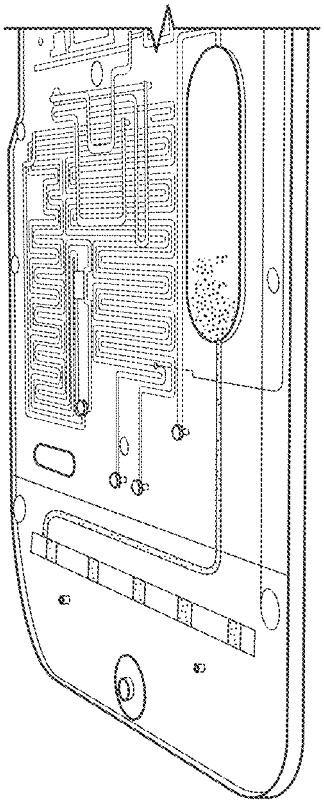
FIG. 1B is an image of an example of a microfluidic device for blood analysis along with the camera attachment shown in FIG. 1A.
Figure 1A:
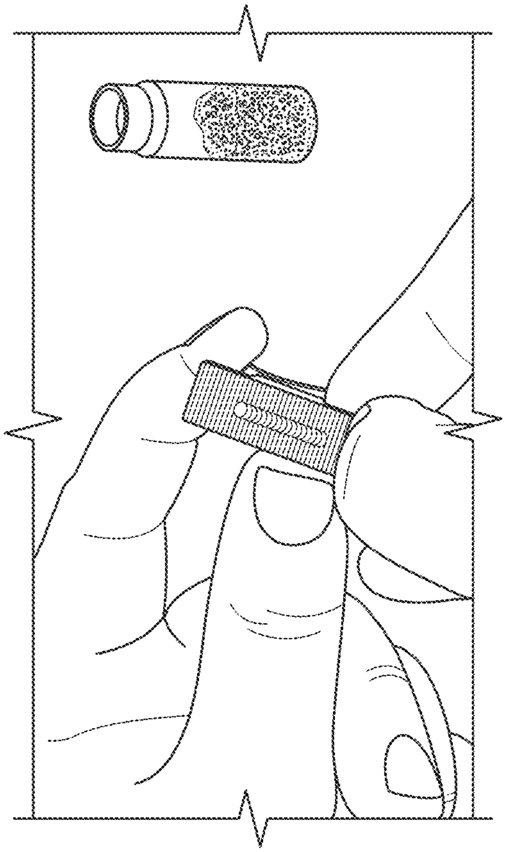
FIG. 1A is an image of a smartphone camera imaging attachment that incorporates a blood smear strip for malaria detection.
Figure 1C:
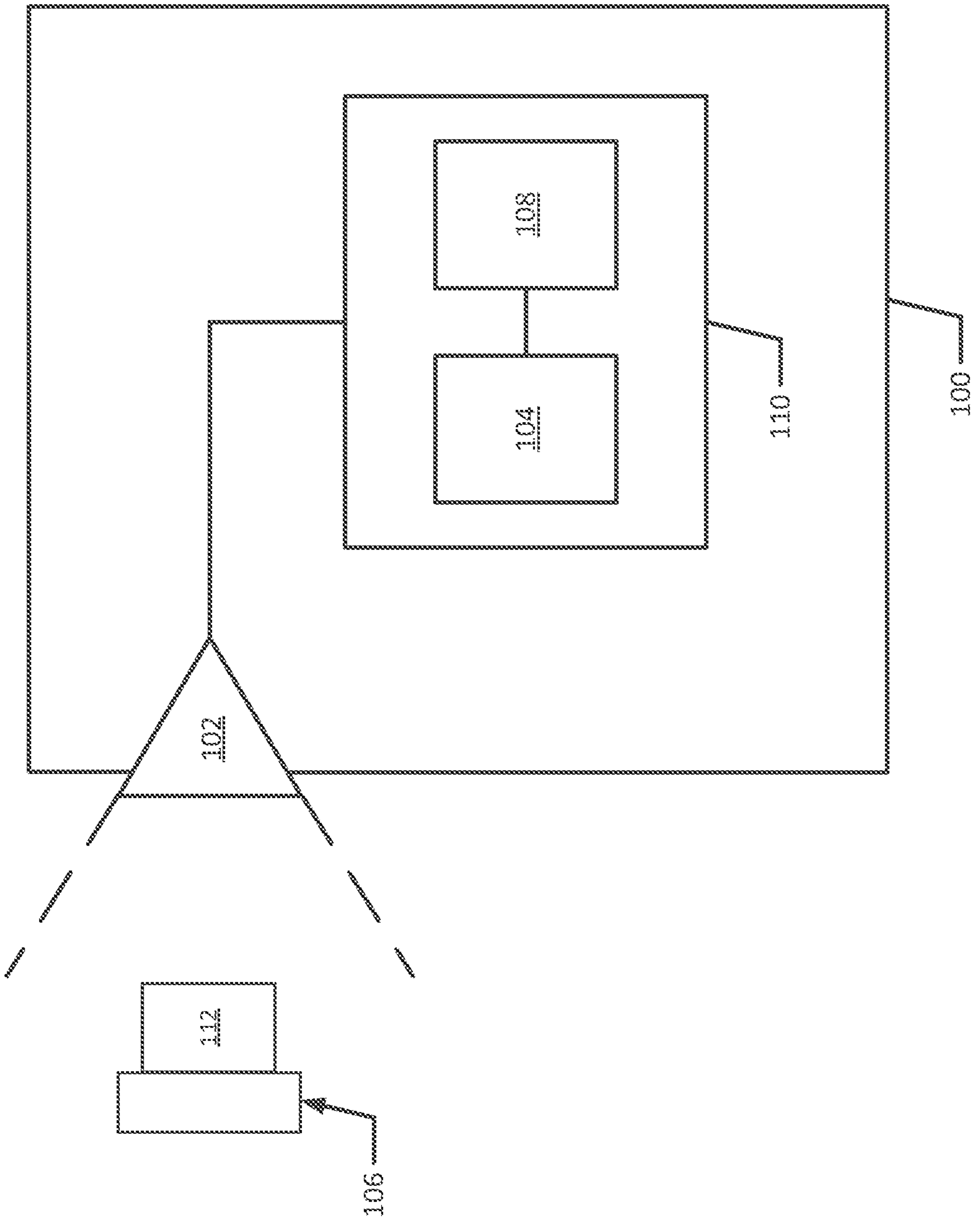
FIG. 1C illustrates an exemplary overview apparatus for making a determination whether or not the malaria parasite is detected in a blood sample.

FIG. 1C illustrates an exemplary overview apparatus for making a determination whether or not the malaria parasite is detected in a blood sample. As shown in FIG. 1C, one embodiment of the apparatus 100 comprises an image capture mechanism 102. In one aspect, the image capture mechanism 102 can be camera. The image capture mechanism 102 can take still and/or video images. Generally, the image capture mechanism 102 will be a digital camera, but can be an analog device equipped with or in communication with an appropriate analog/digital converter. The image capture mechanism 102 may also be a webcam, scanner, recorder, or any other device capable of capturing a still image or a video.

In one aspect, the image capture mechanism 102 is in direct communication with a computing device 110 through, for example, a network (wired (including fiber optic), wireless or a combination of wired and wireless) or a direct-connect cable (e.g., using a universal serial bus (USB) connection, IEEE 1394 “Firewire” connections, and the like). In other aspects, the image capture mechanism 102 can be located remotely from the computing device 110, but capable of capturing an image and storing it on a memory device such that the image can be downloaded or transferred to the computing device 110 using, for example, a portable memory device and the like. In one aspect, the computing device 110 and the image capture mechanism 102 can comprise or be a part of a device such as a smartphone, table, laptop computer or any other mobile computing device.

In a basic configuration, the computing device 110 can be comprised of a processor 104 and a memory 108. The processor 104 can execute computer-readable instructions that are stored in the memory 108. Moreover, images captured by the image capture device 102, whether still images or video, can be stored in the memory 108 and processed by the processor 104 using computer-readable instructions stored in the memory 108.

The processor 104 is in communication with the image capture device 102 and the memory 108. The processor 104 can execute computer-readable instructions stored on the memory 108 to capture, using the image capture device 102, an image of a blood sample on or contained in a blood smear test strip 106 such as the one shown in FIG. 1B. In some instances, the lens of the image capture device 102 may work in concert with a magnification device 112 such as a microscope configured to adapt to a smartphone camera so that the captured image is a magnification of the blood sample on or contained in a blood smear test strip 106.

The processor 104 can further execute computer-readable instructions stored on the memory 108 to detect, from the image of the blood sample on or contained in a blood smear test strip 106, the presence or absence of the malaria parasite in the blood sample represented by the blood sample on or contained in a blood smear test strip 106. Generally, the processor 104 of the apparatus 100 executing computer-readable instructions stored in the memory 108 cause the processor 104 to make a determination about the image acquired by the image capture device 102 of the blood sample on or contained in a blood smear test strip 106. The processor executes machine learning (ML) code 116 that has been trained to identify the malaria parasite in the image of the blood sample on or contained in a blood smear test strip 106 captured by the image capture device 102. Generally, the executable ML code 116 is stored in the memory 108.

Generally, the blood sample undergoes a staining process prior to the image capture step. For example, device staining of *Plasmodium* parasites within human red blood cells comprises collecting approximately 5 microliters of whole blood by sterile finger (or heel) stick and drawn by capillary action into the blood smear test strip 106. As the blood flows into a chamber of the blood smear test strip 106, it mixes with both a preloaded parasite stain and an aqueous diluent/buffer. Following incubation, the blood smear test strip can be inserted into the smartphone magnification device 112 and imaged using the image capture device 102. In one non-limiting specific example, the stain comprises a blend of azure B (trimethylthionine) and eosin Y (tetrabromofluorescein) in methanol; the diluent comprises phosphate buffered saline (PBS), pH 6.8; the final dilution of RBC sample in stain and diluent is approximately 1:1,000; and the staining protocol is optimized for use at ambient temperatures with an incubation time of 5 minutes.

Figure 1D:
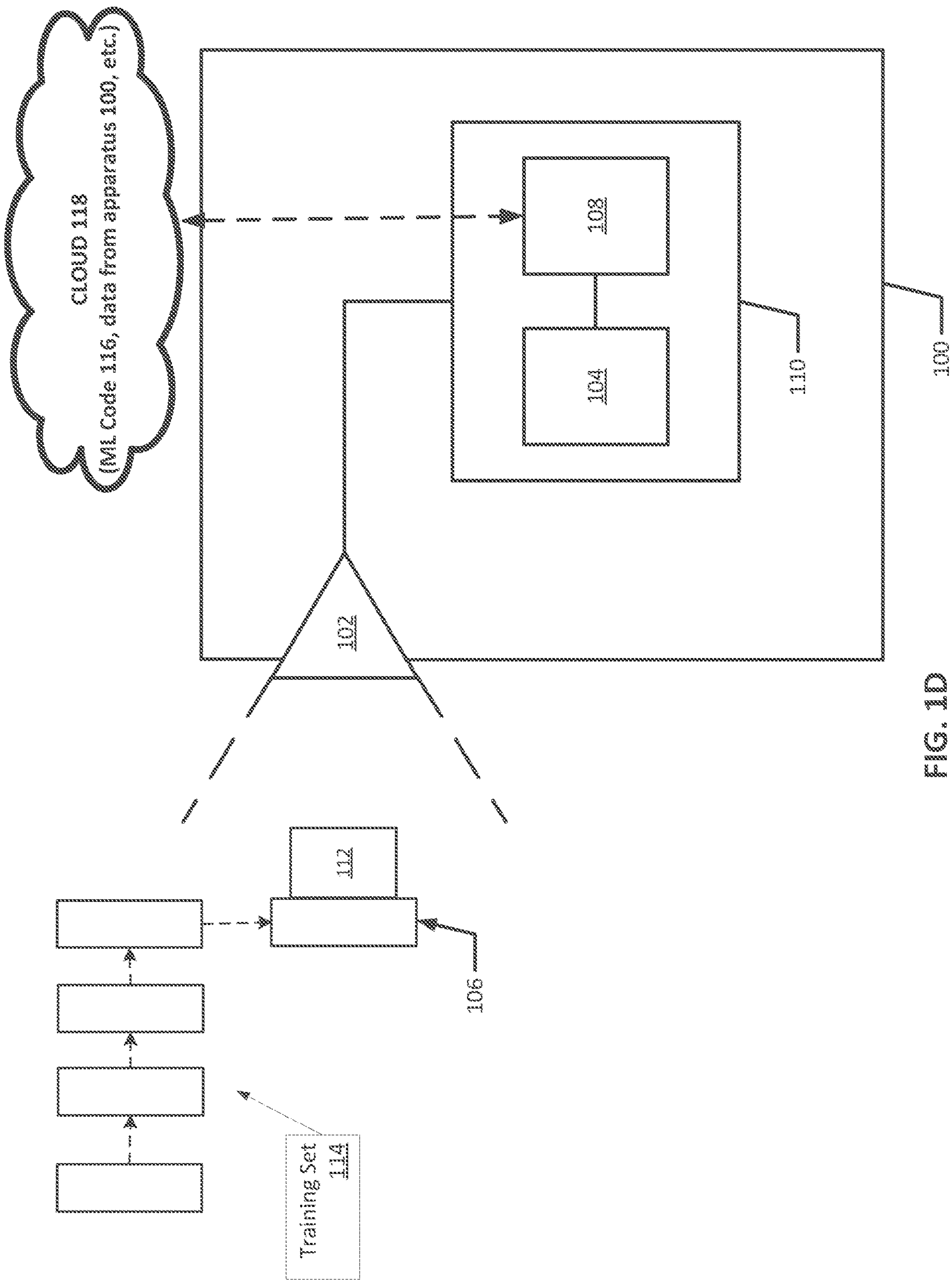
FIG. 1D is an illustration of an apparatus for making a determination whether or not the malaria parasite is detected in a blood sample, wherein the ML code is trained using a training set of blood sample images.
Figure 2A:
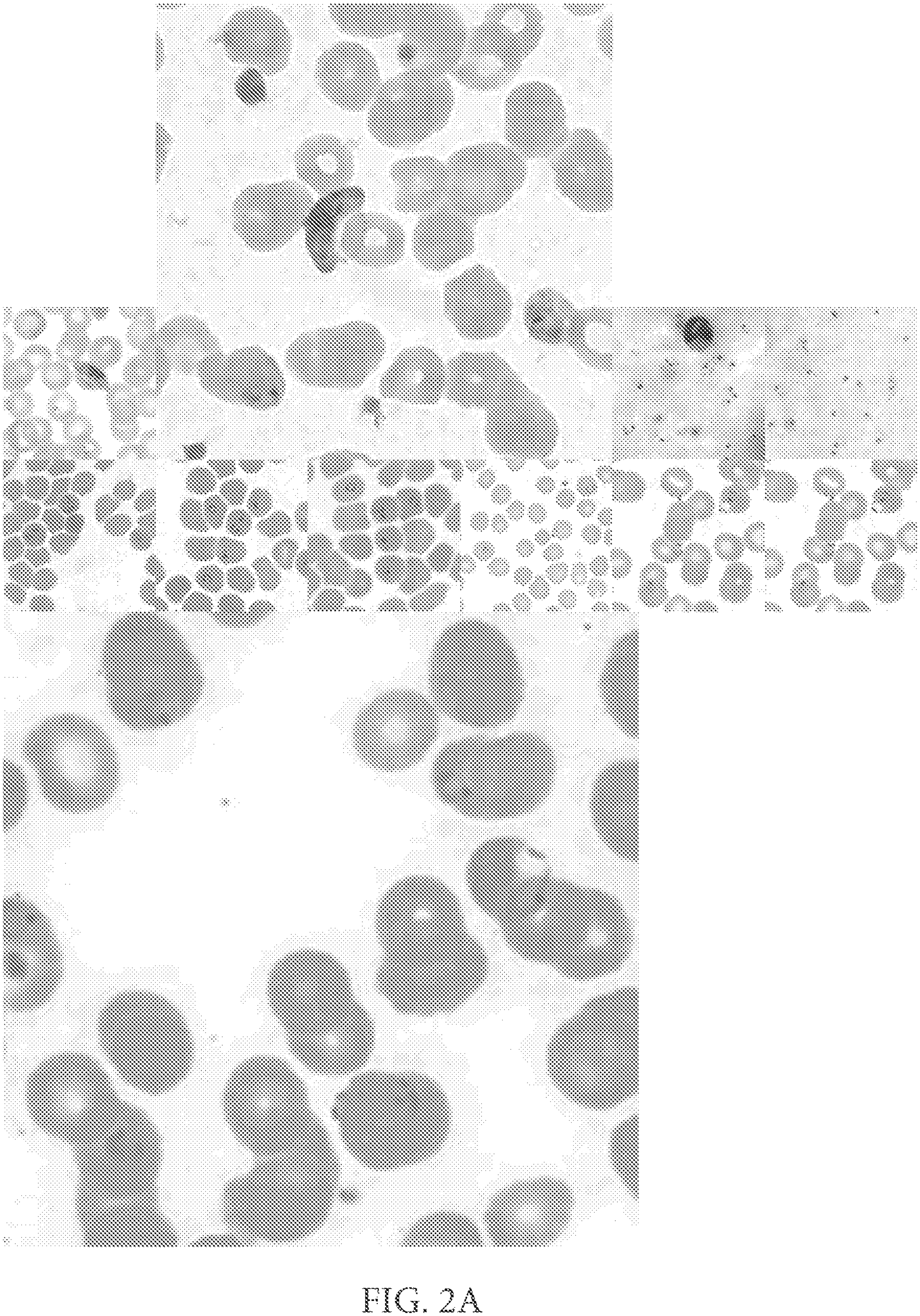
FIGS. 2A-2J are images of known malaria positive blood samples used for training and/or testing the ML algorithm.
Figure 2B:
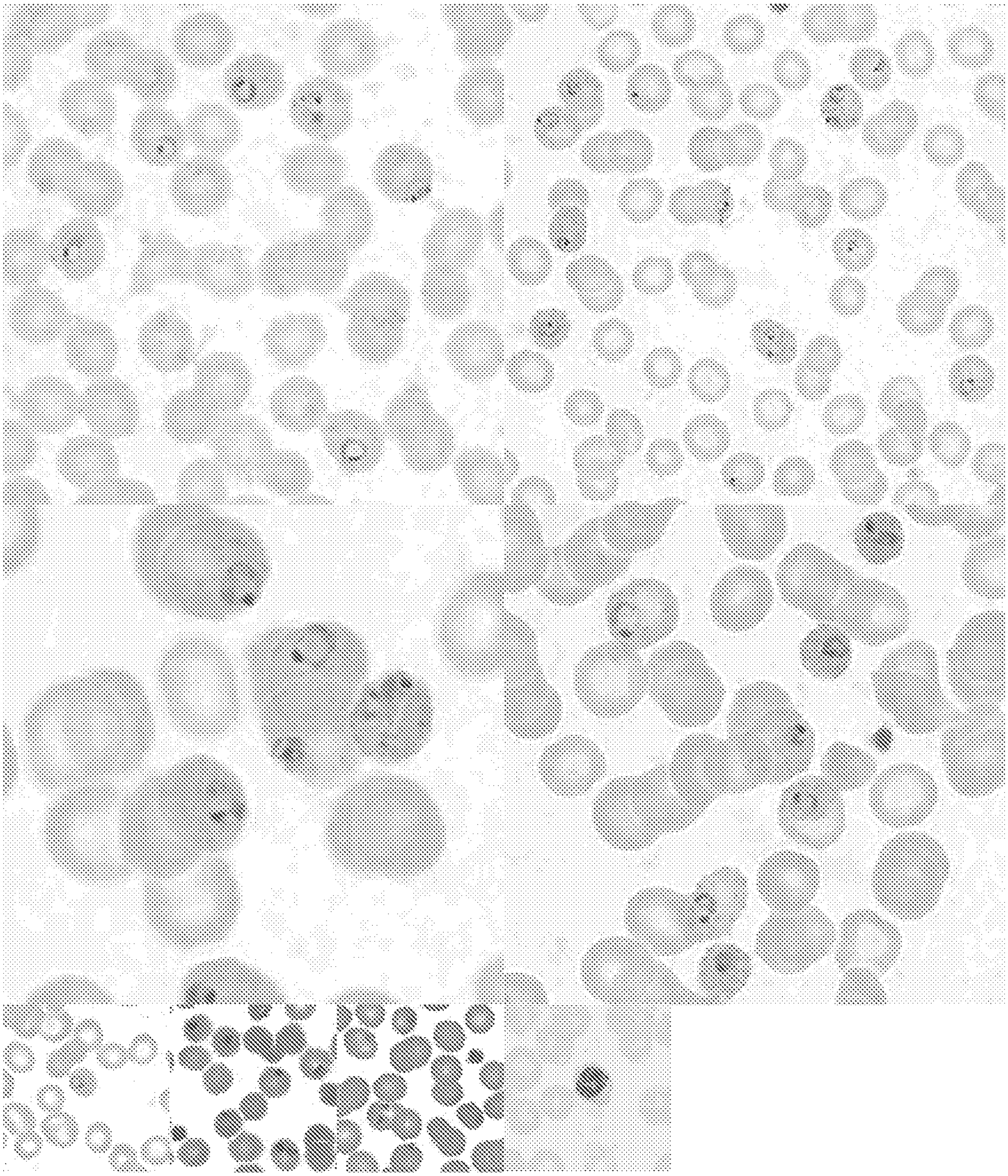
Figure 2C:
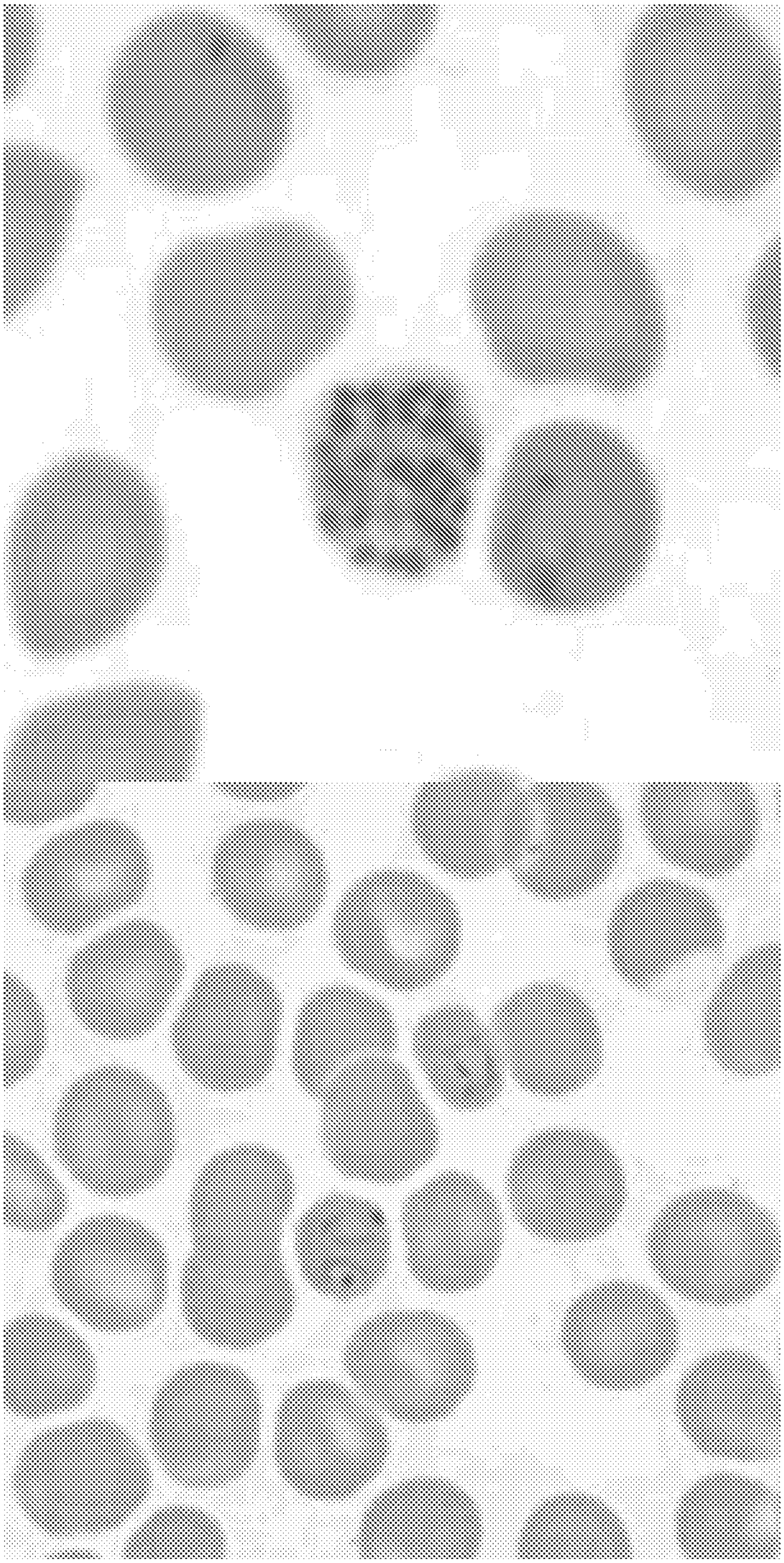
Figure 2D:
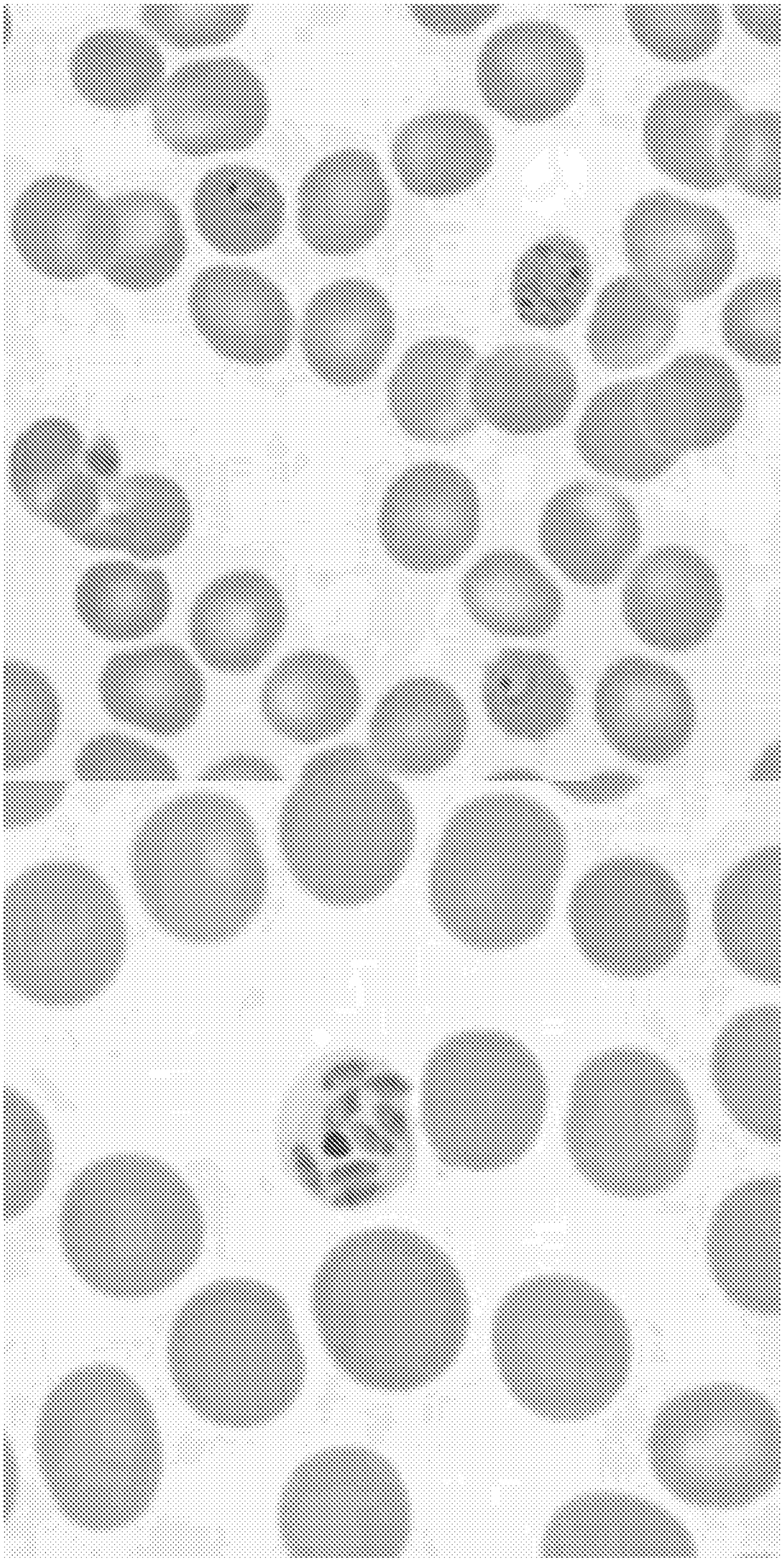
Figure 2E:
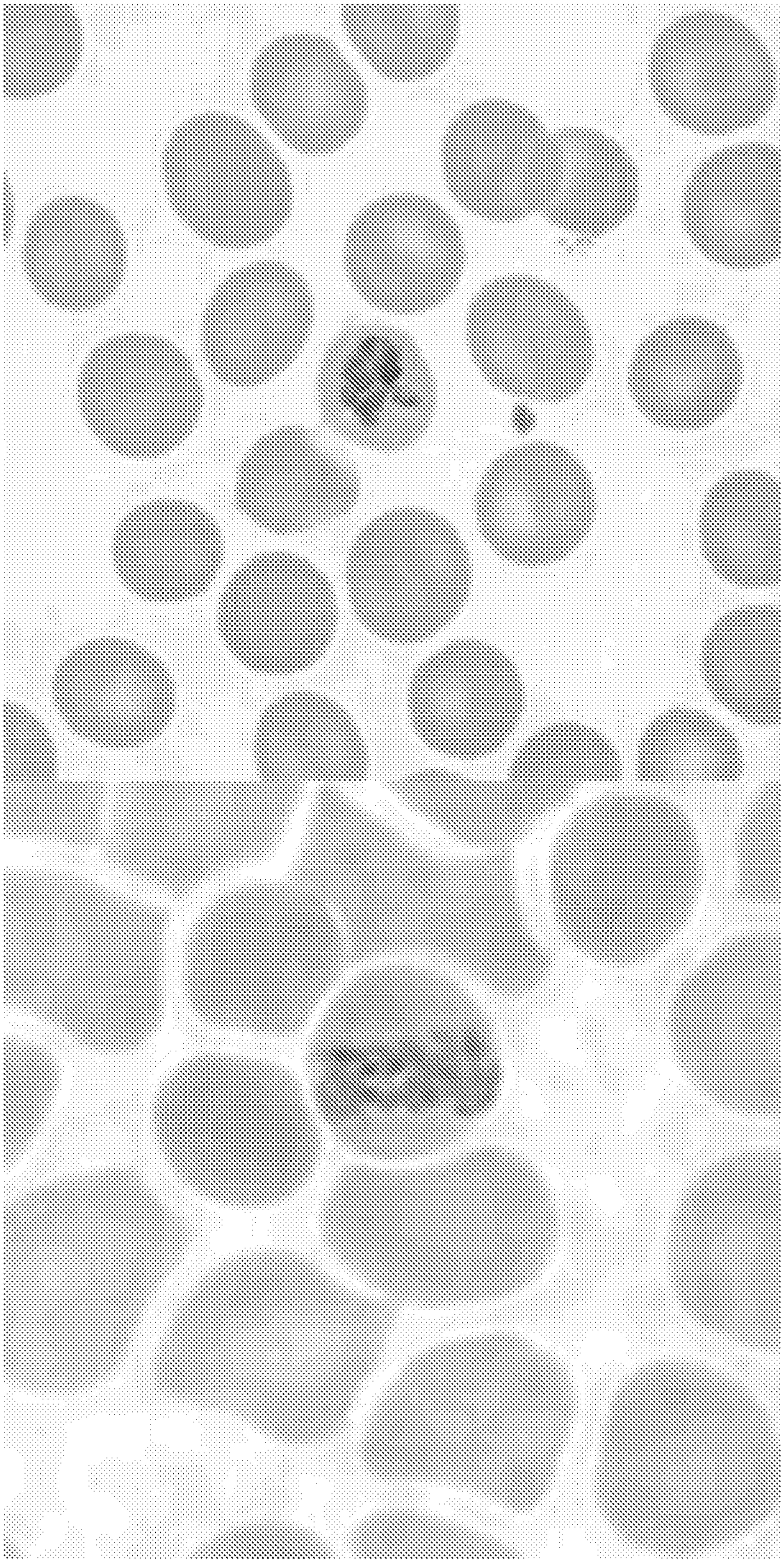
Figure 2F:
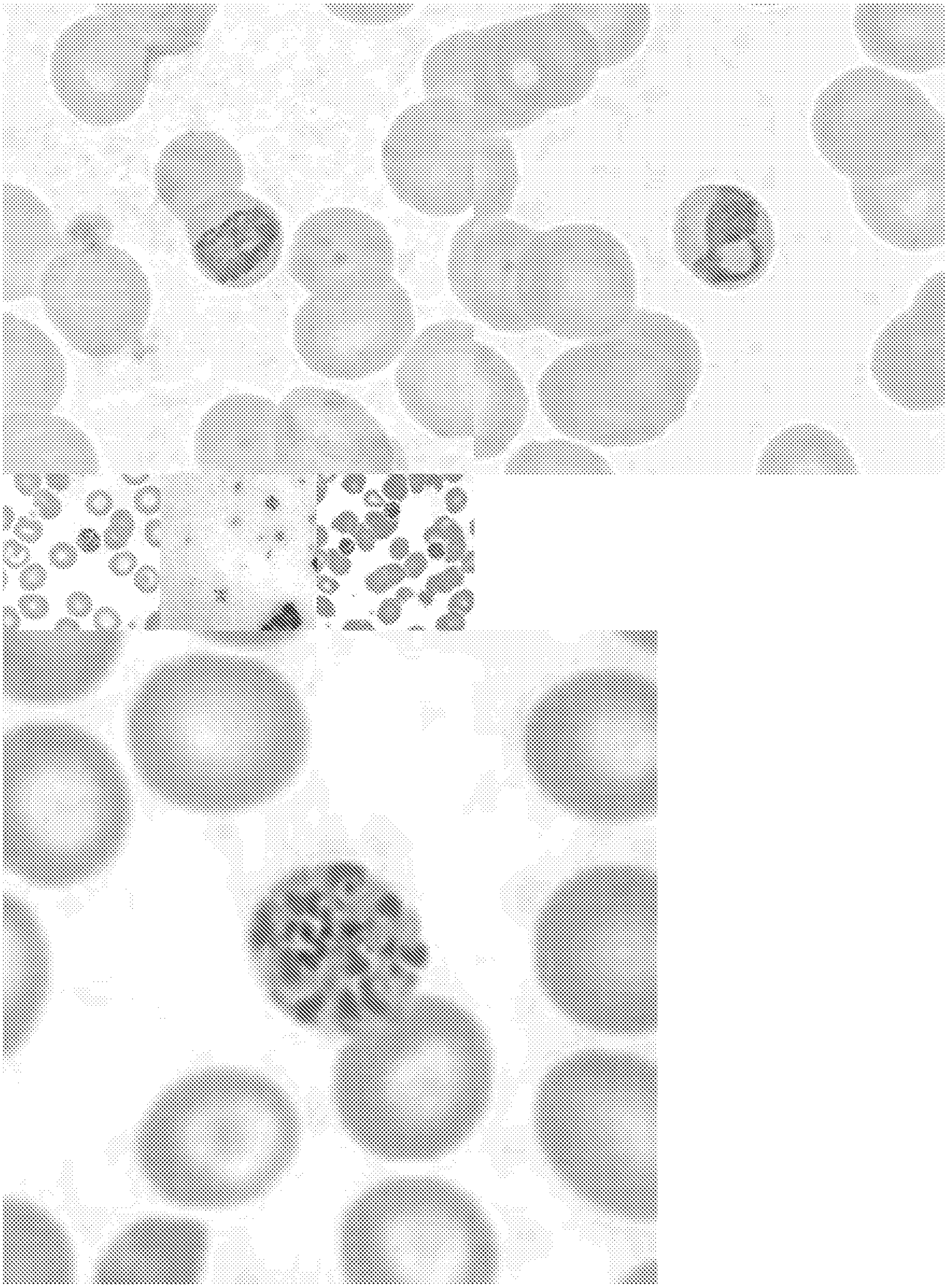
Figure 2G:
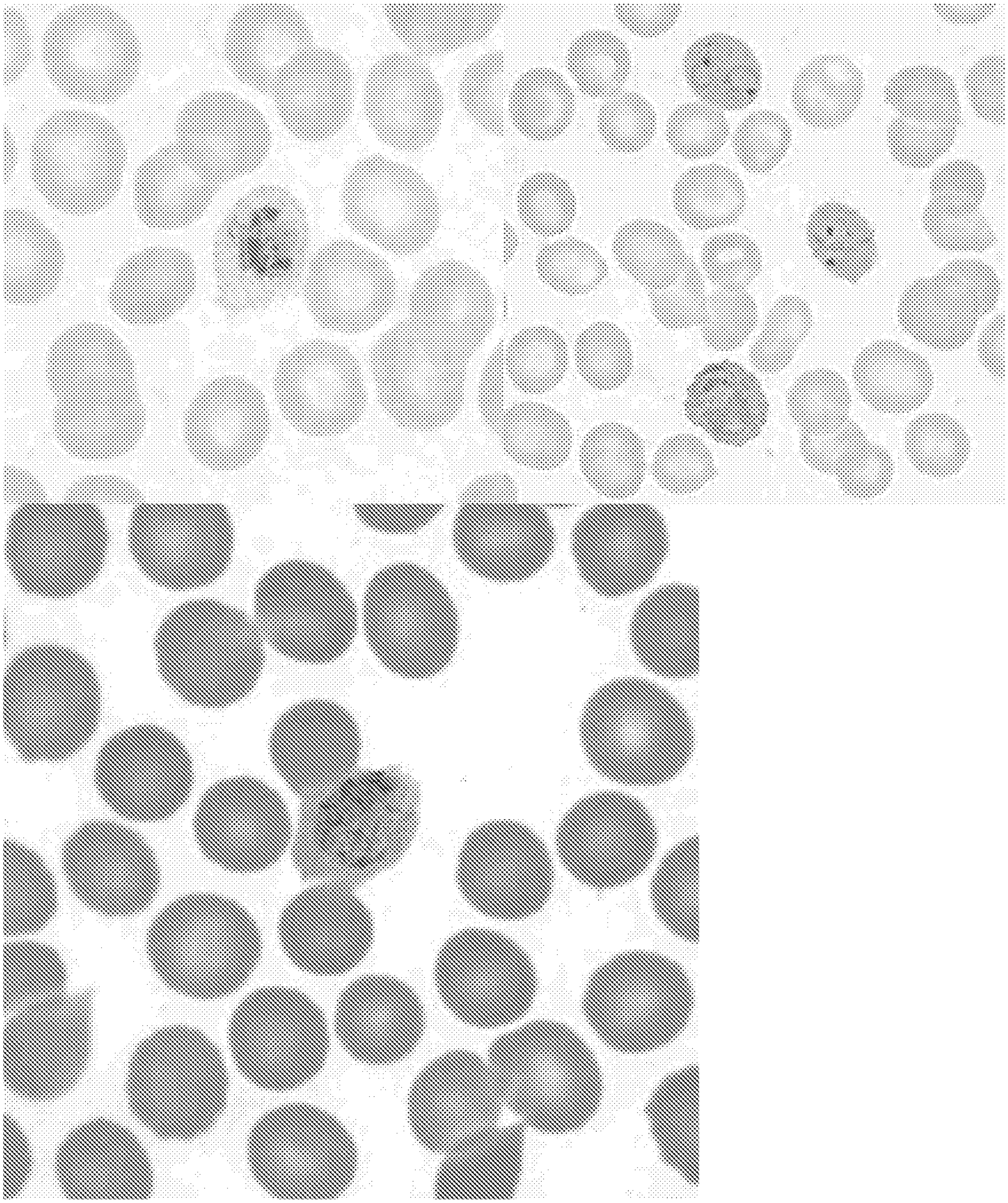
Figure 2H:
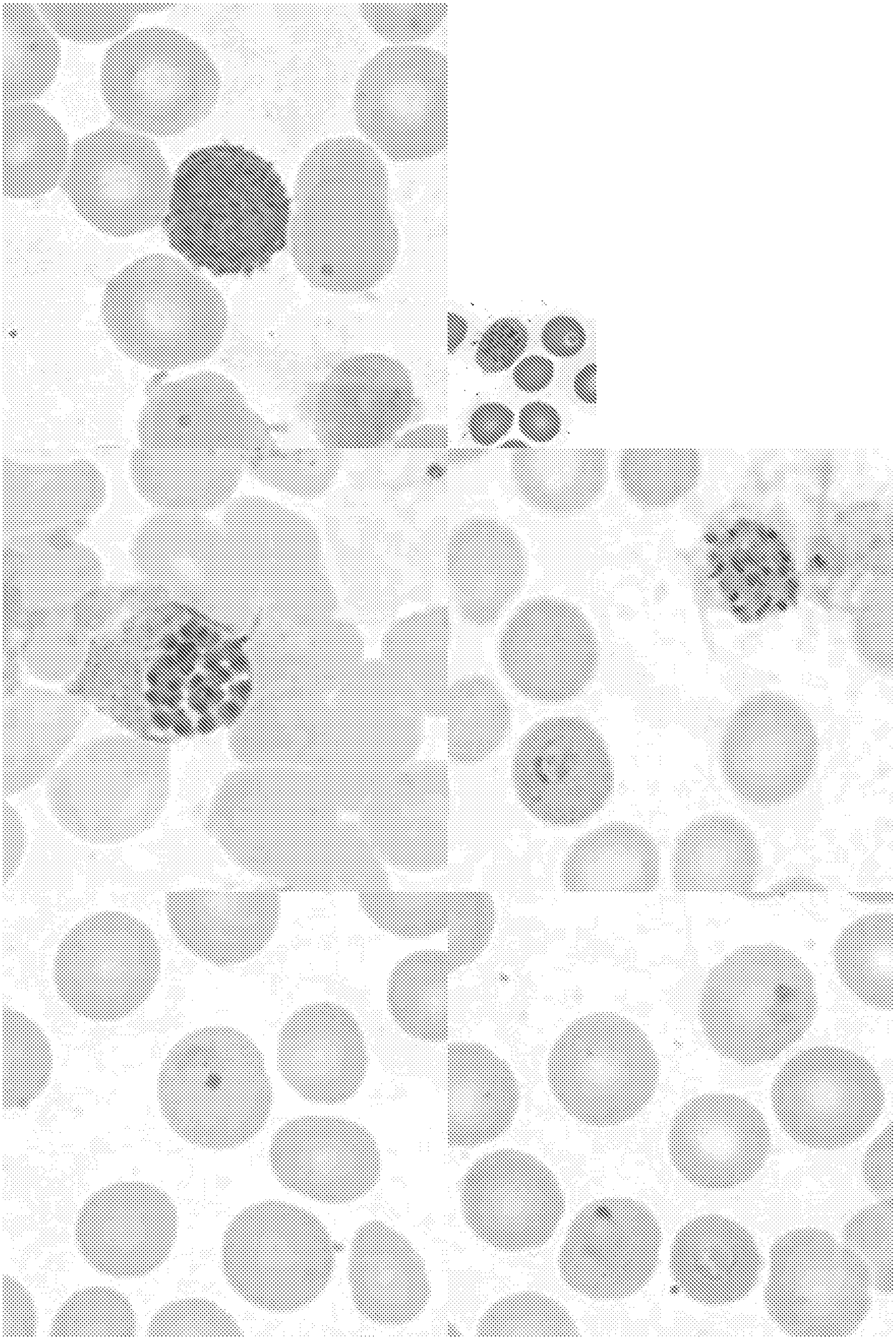
Figure 2I:
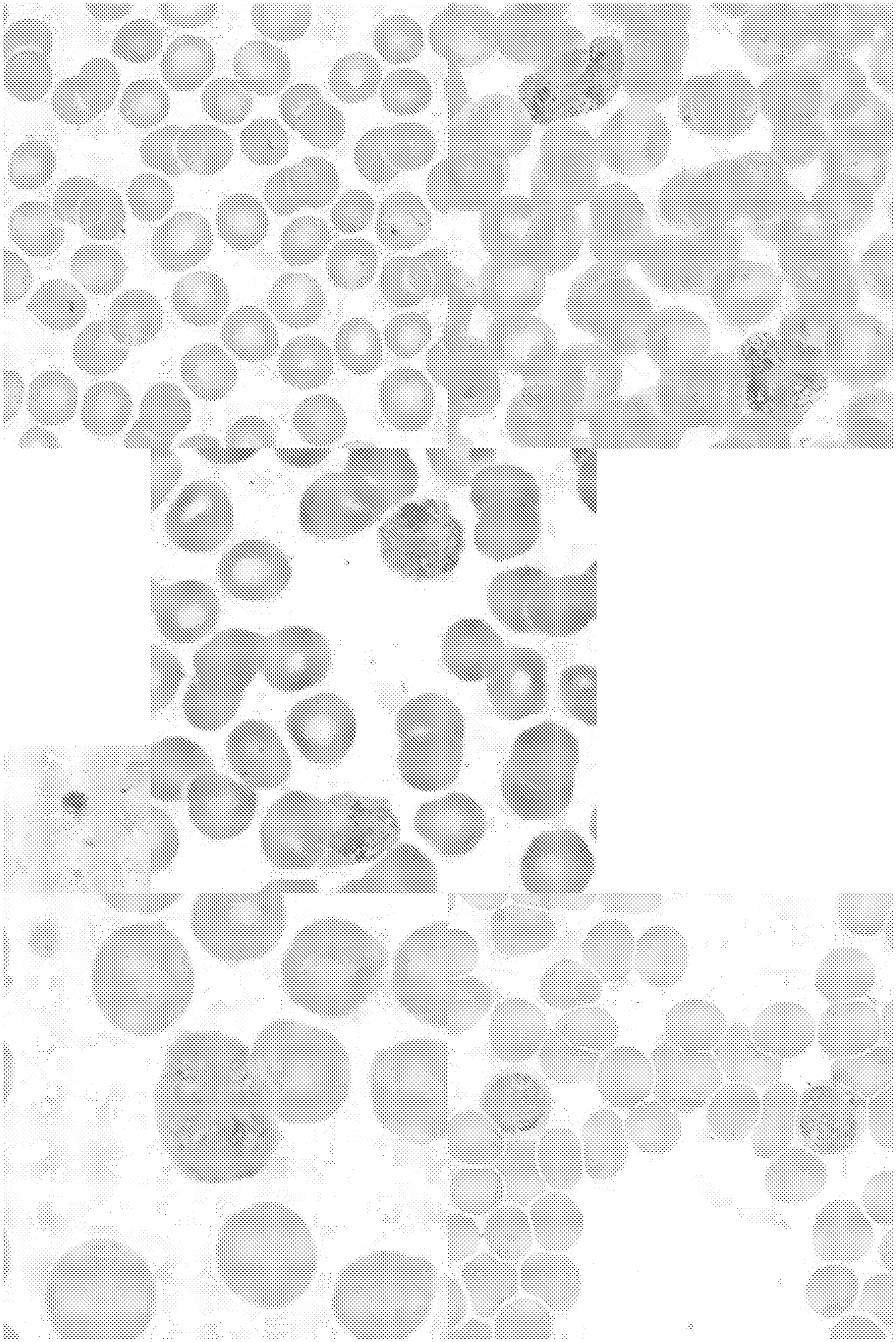
Figure 2J:
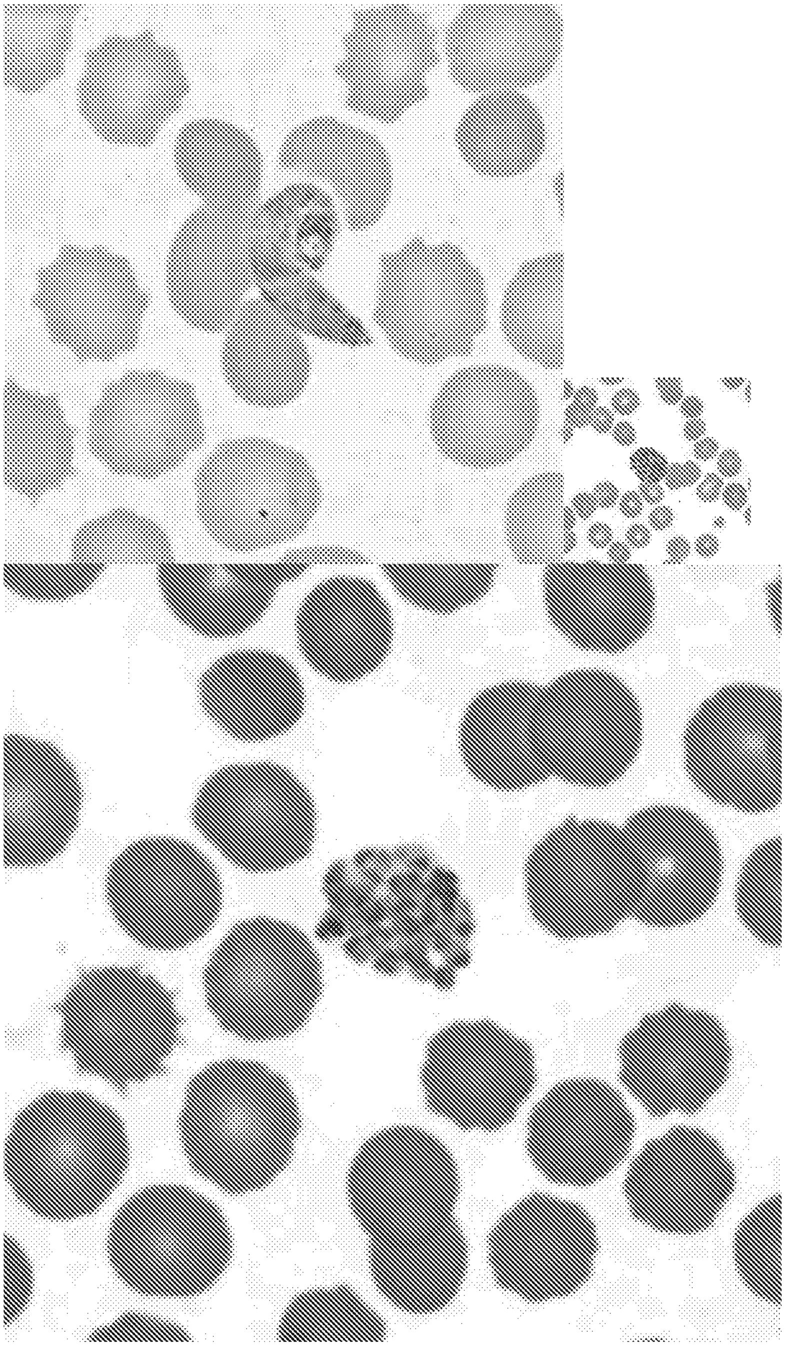
Figure 3A:
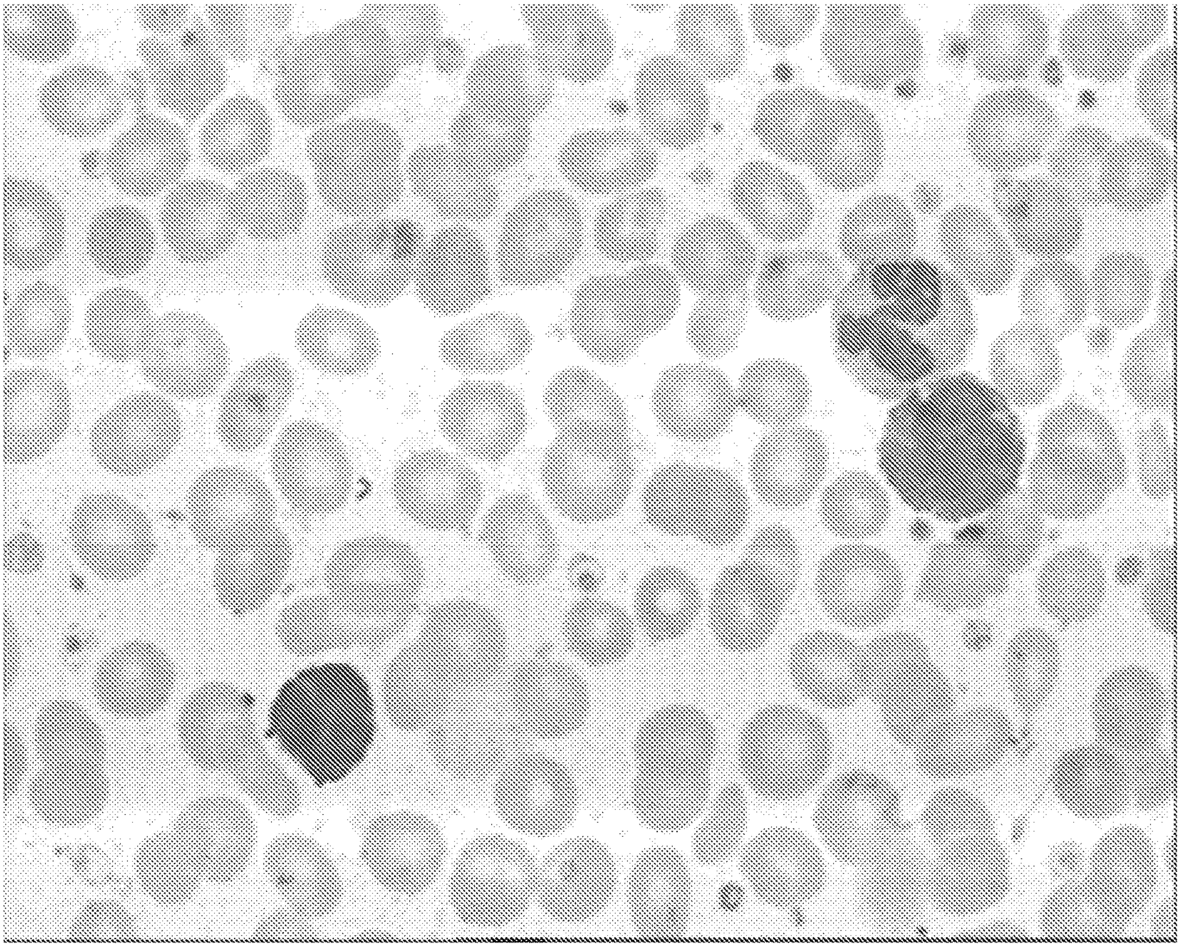
FIGS. 3A-3HH are images of known malaria negative blood samples used for training and/or testing the ML algorithm.
Figure 3B:
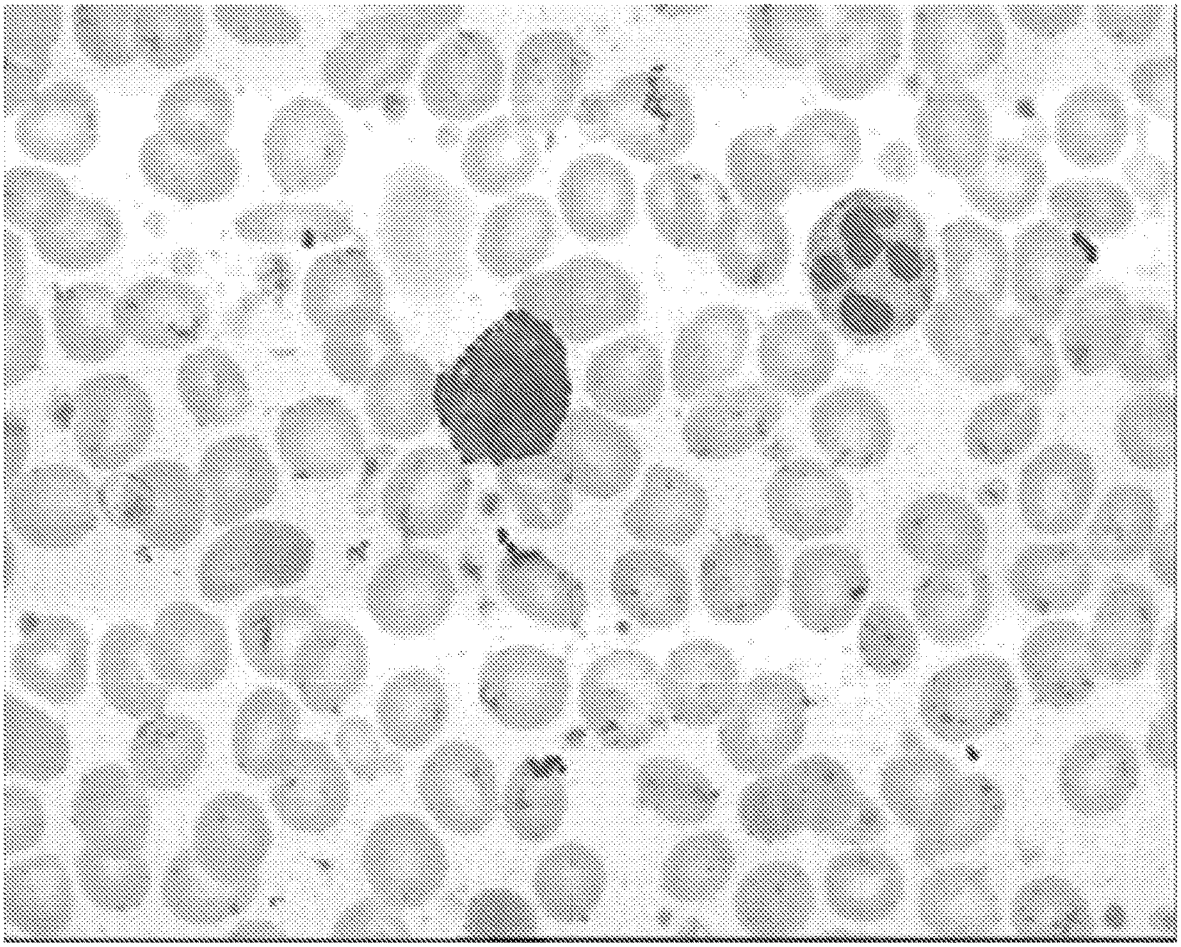
Figure 3C:
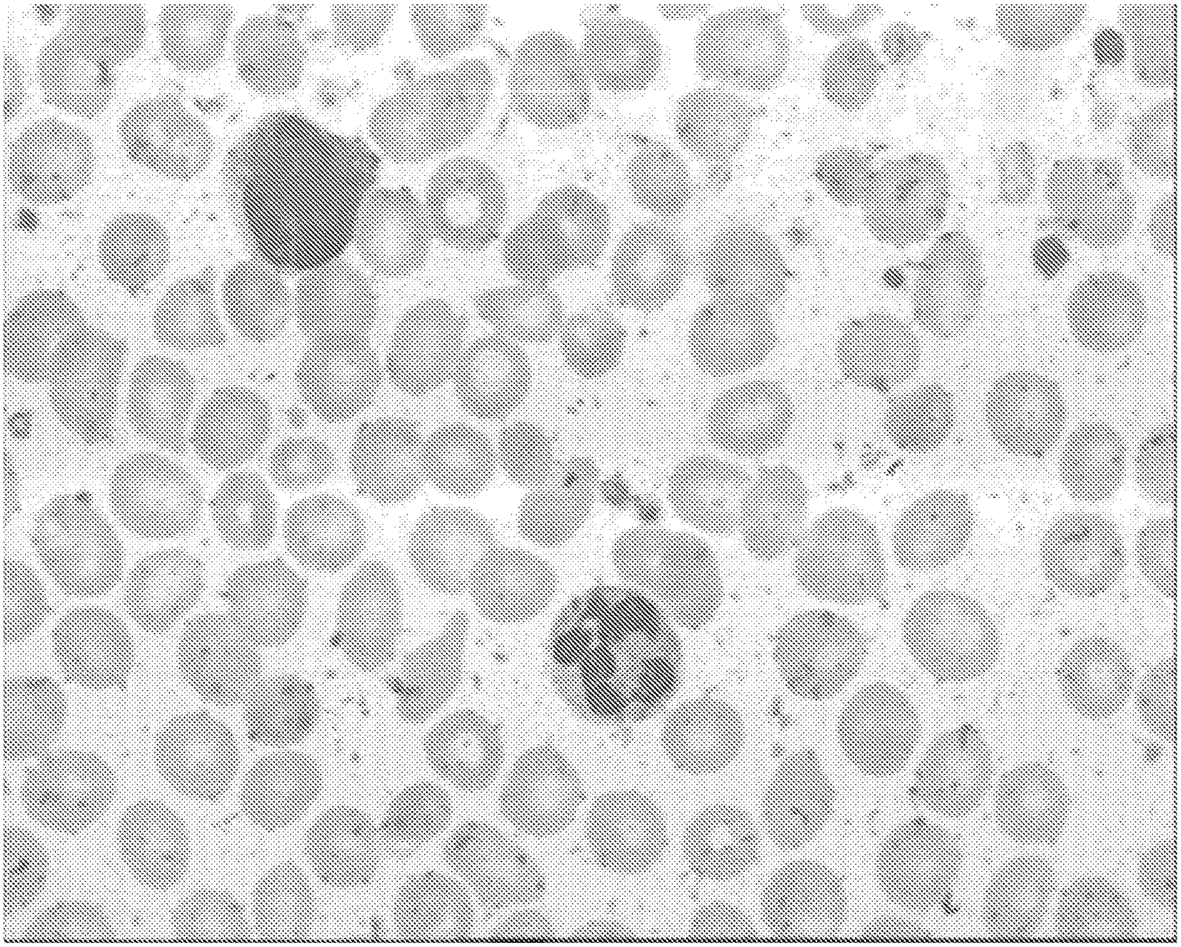
Figure 3D:
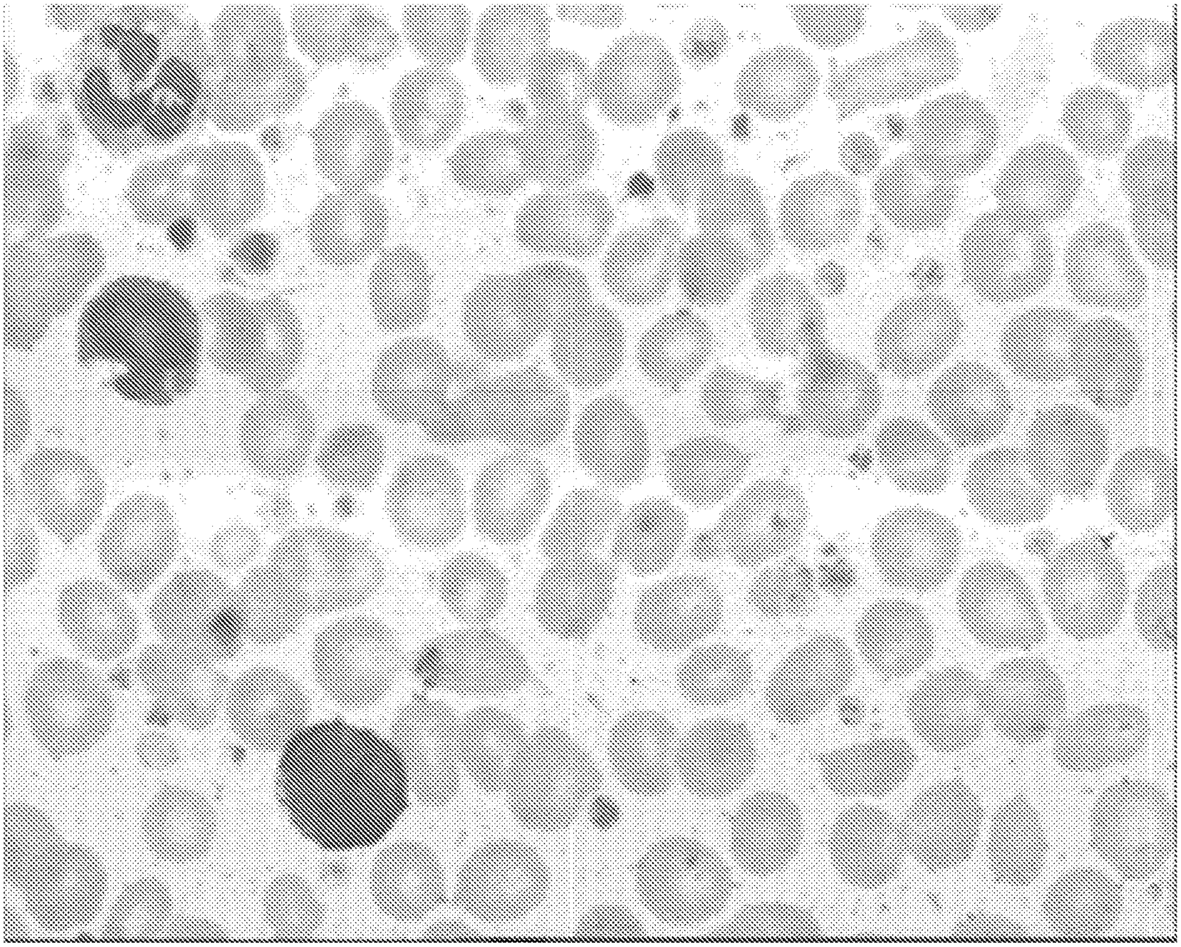
Figure 3E:
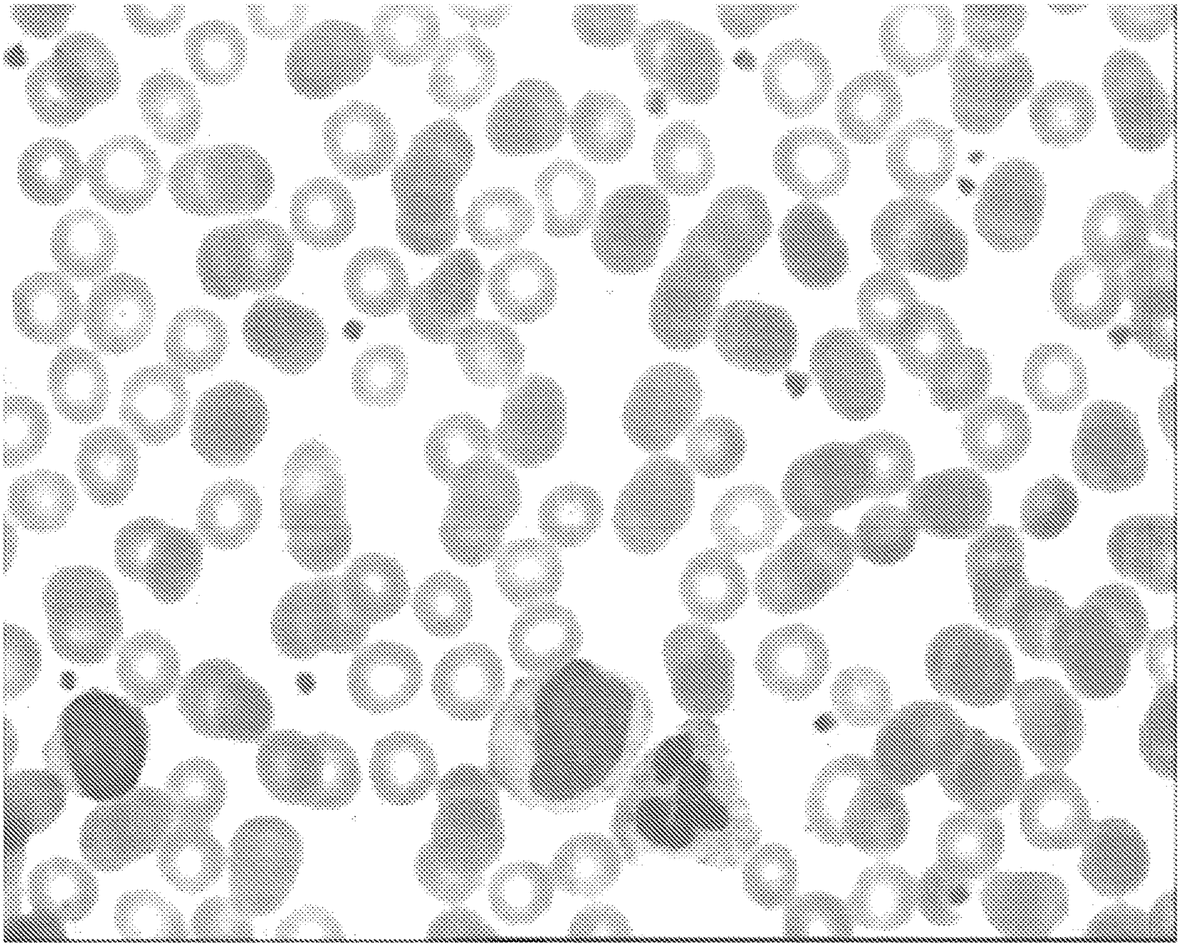
Figure 3F:
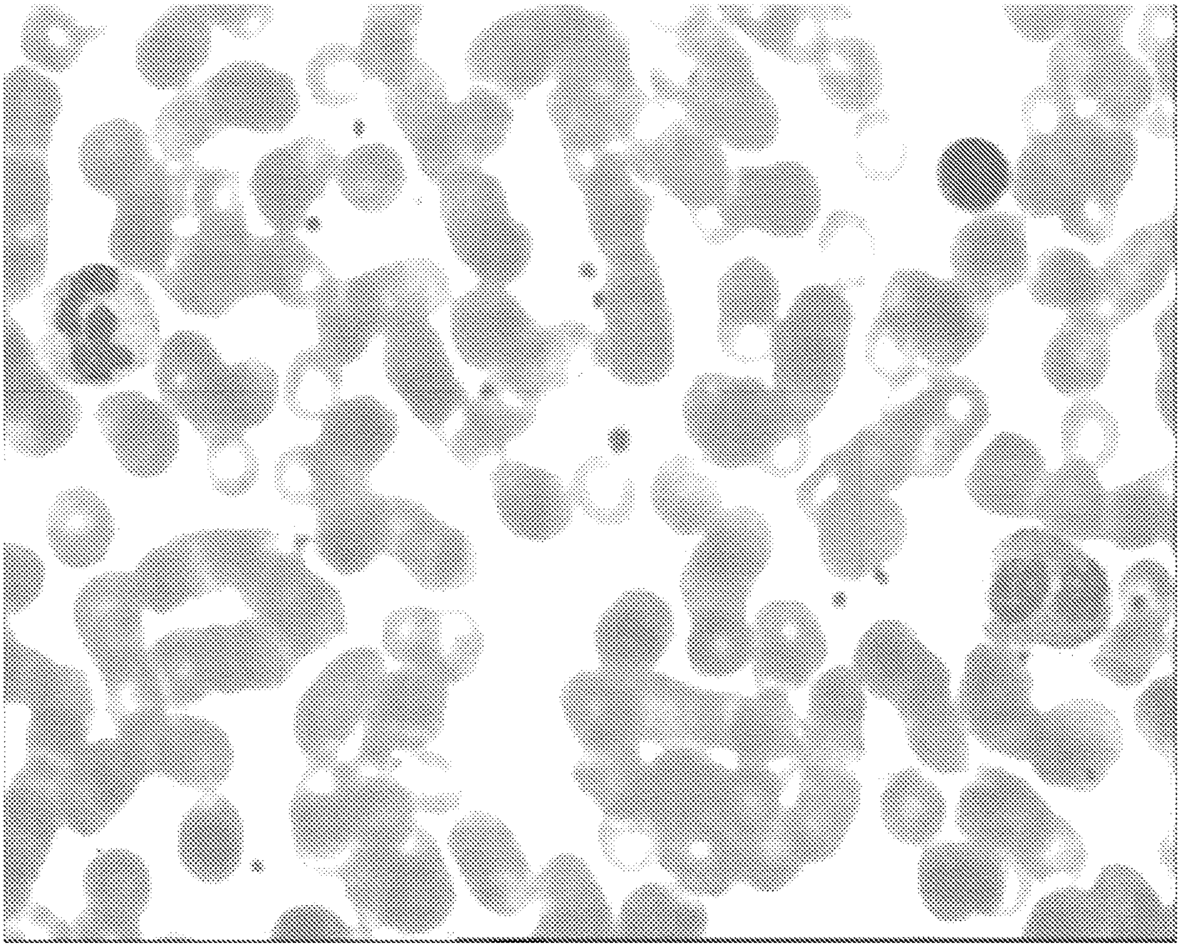
Figure 3G:
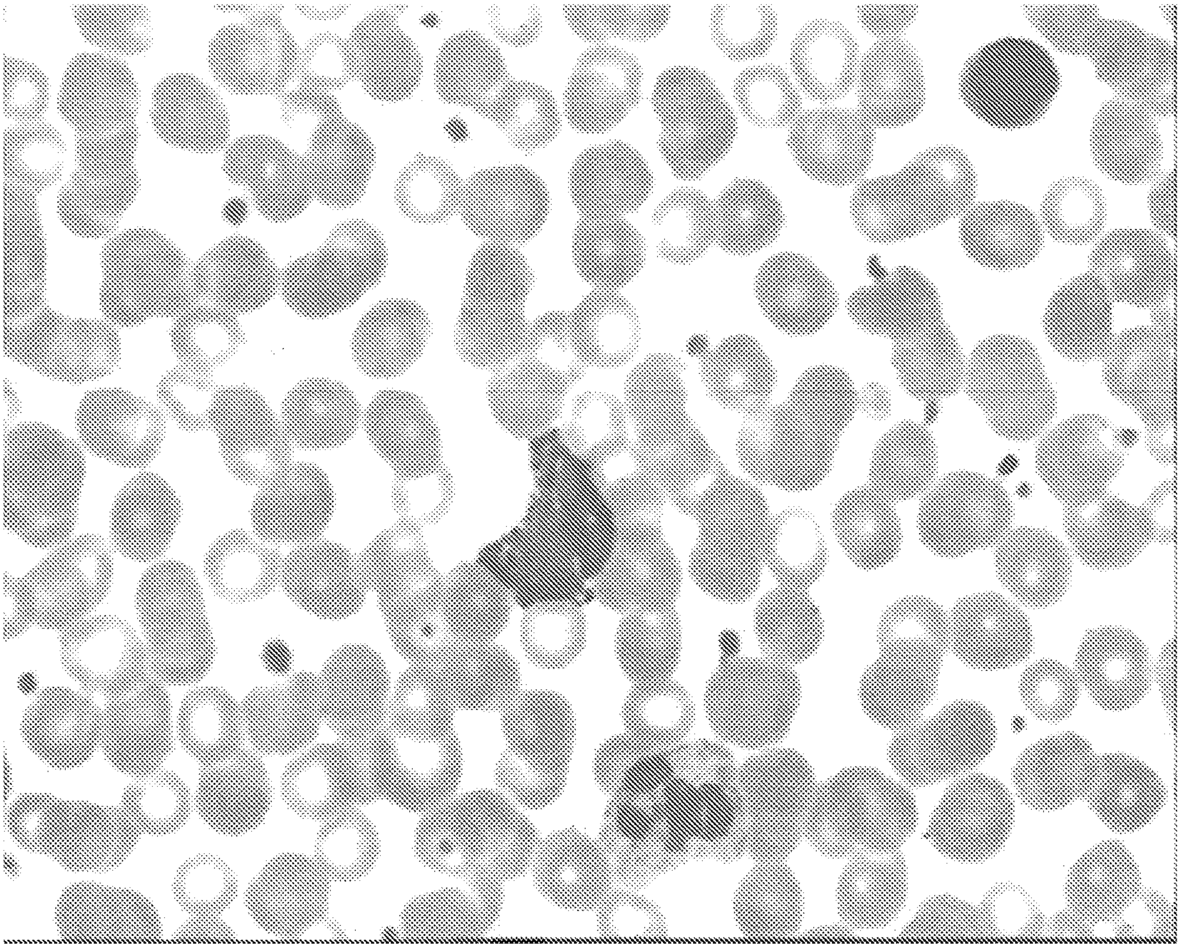
Figure 3H:
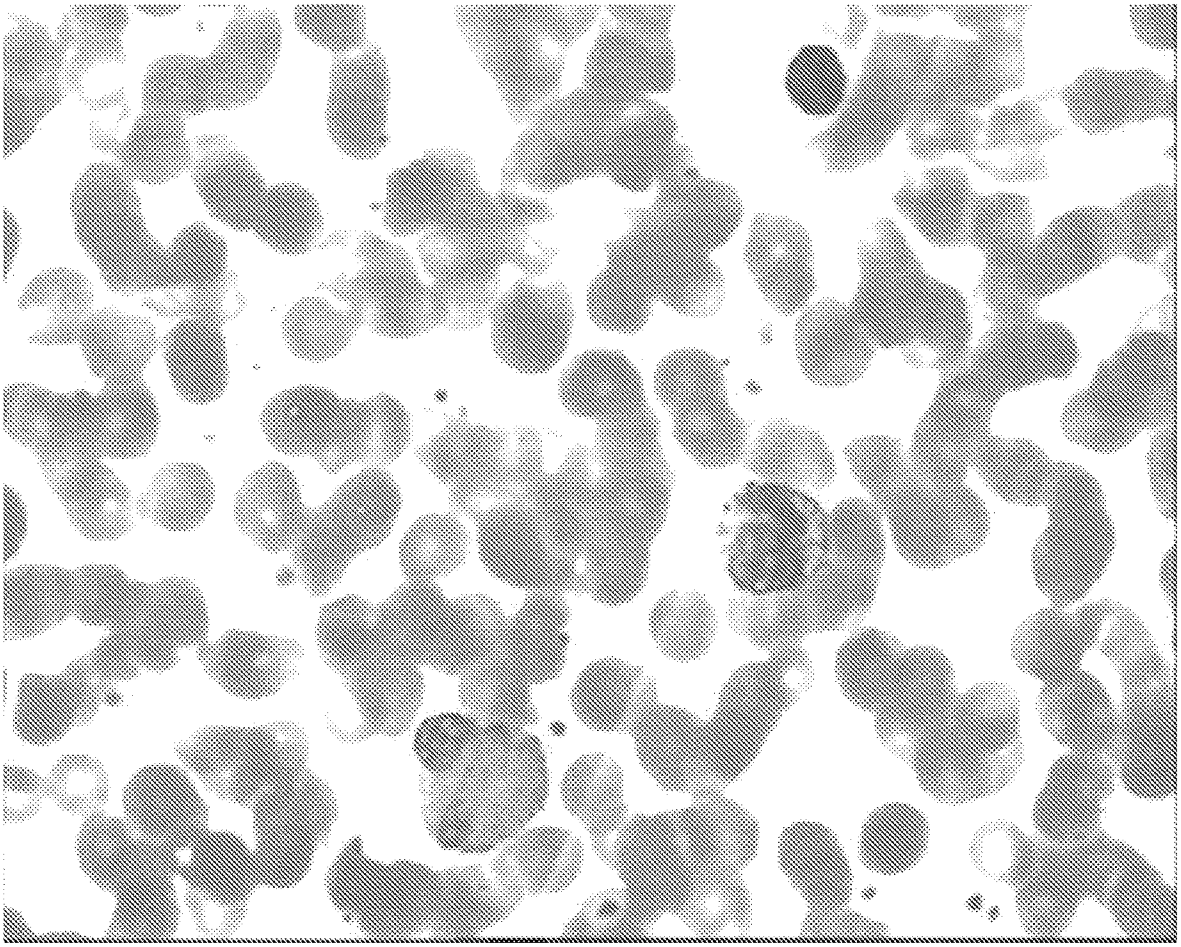
Figure 3I:
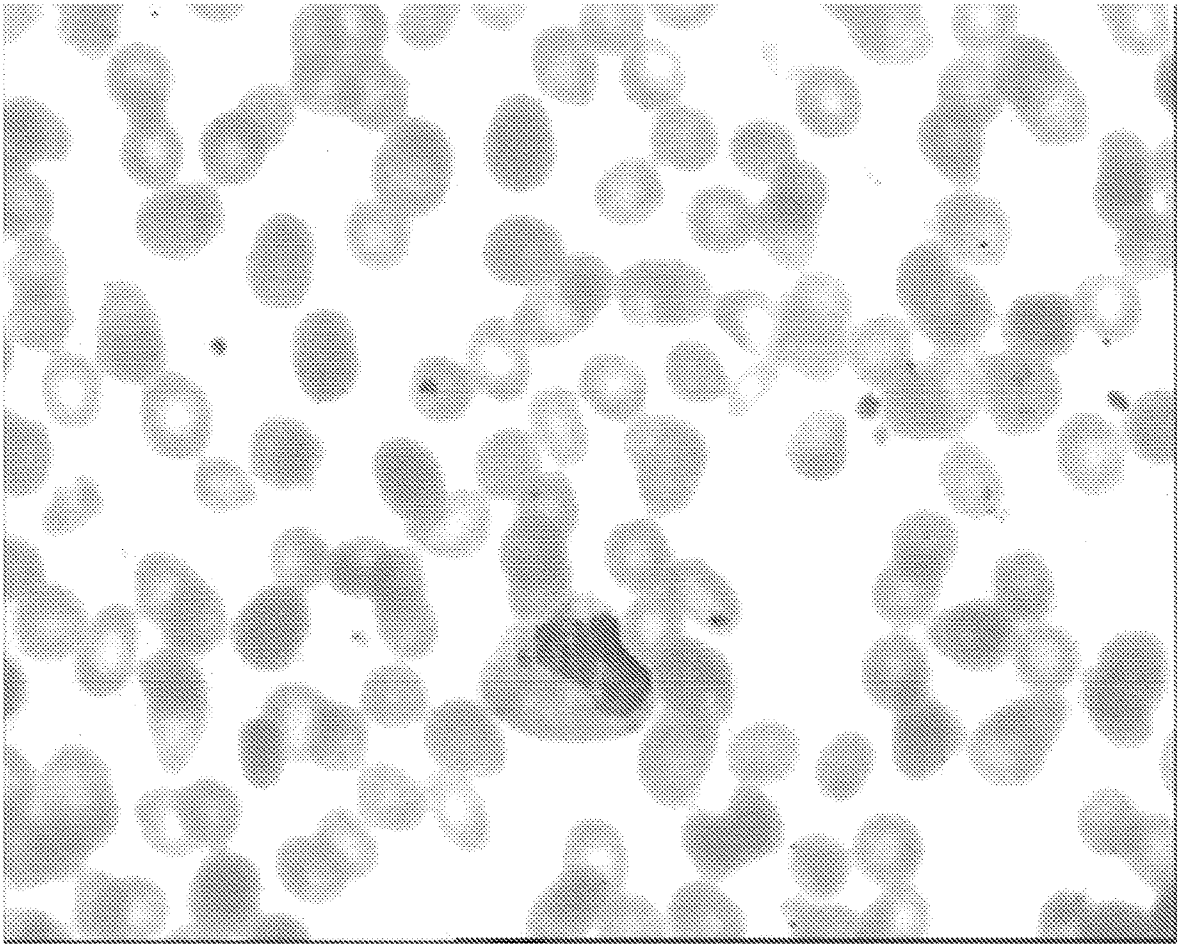
Figure 3J:
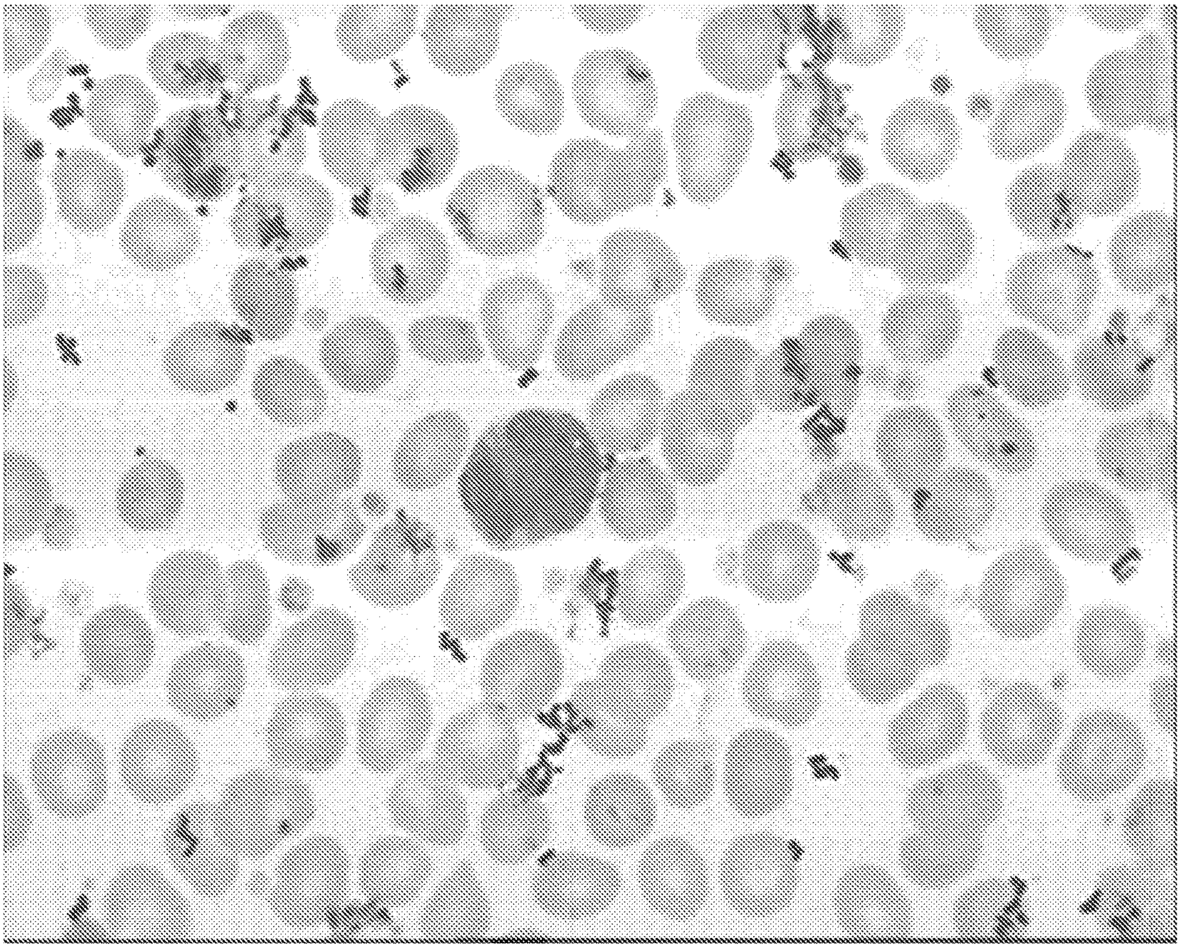
Figure 3K:
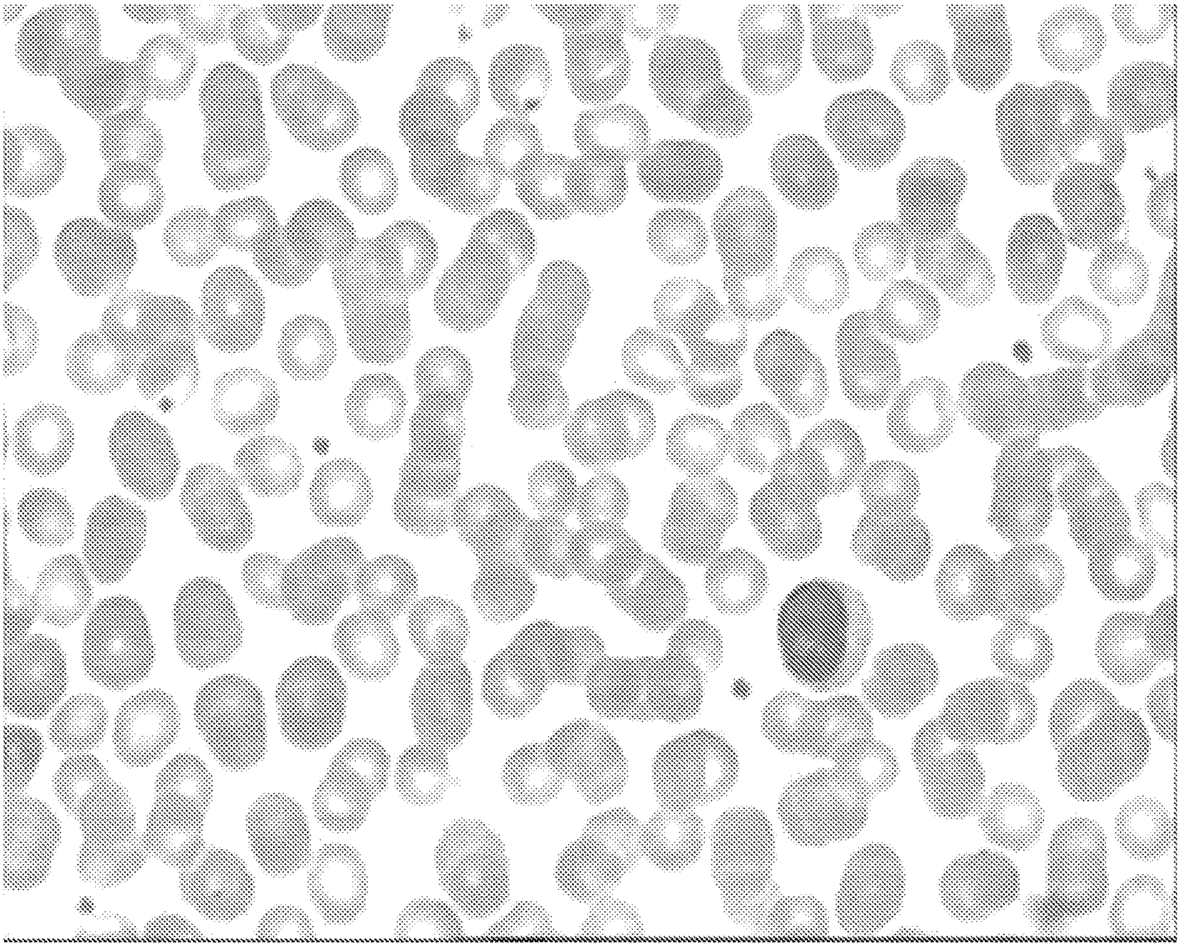
Figure 3L:
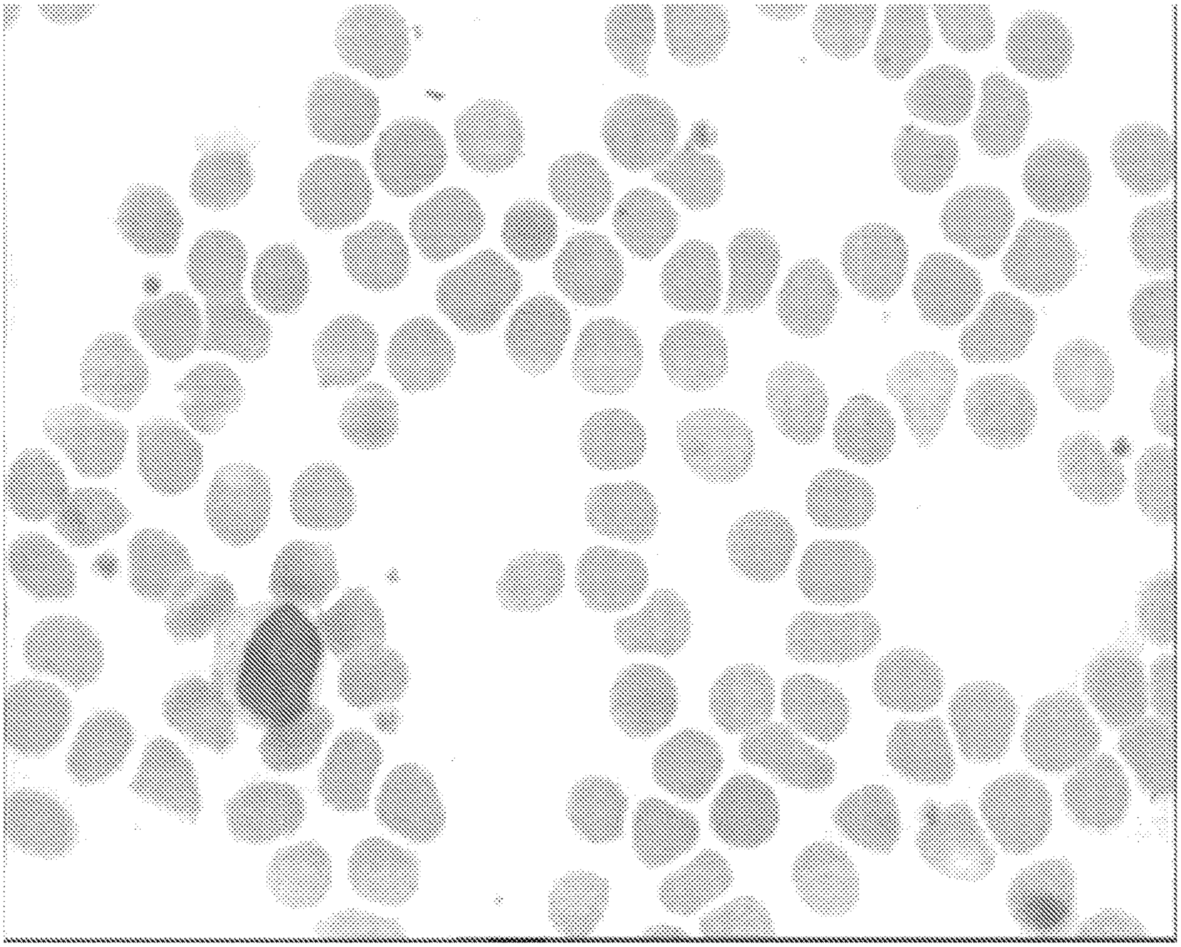
Figure 3M:
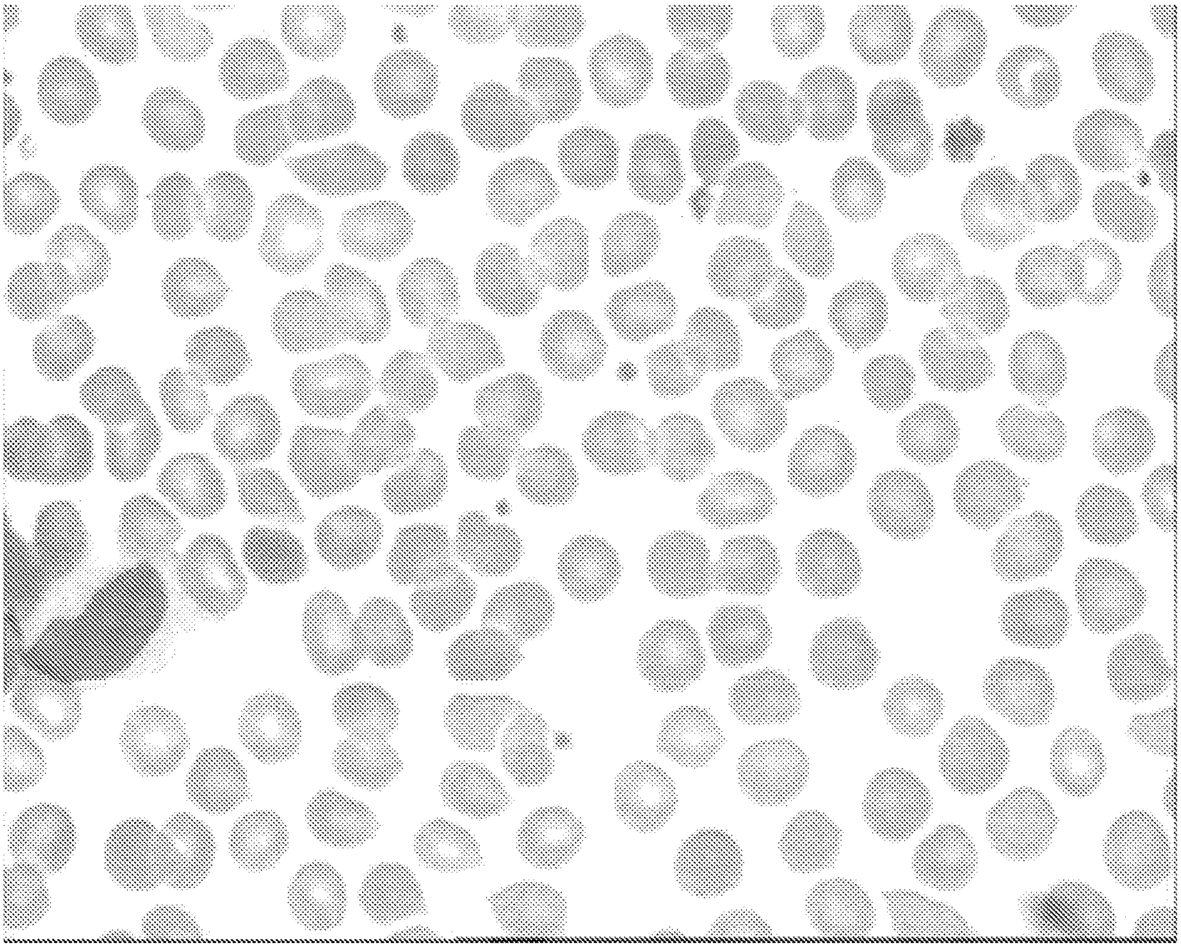
Figure 3N:
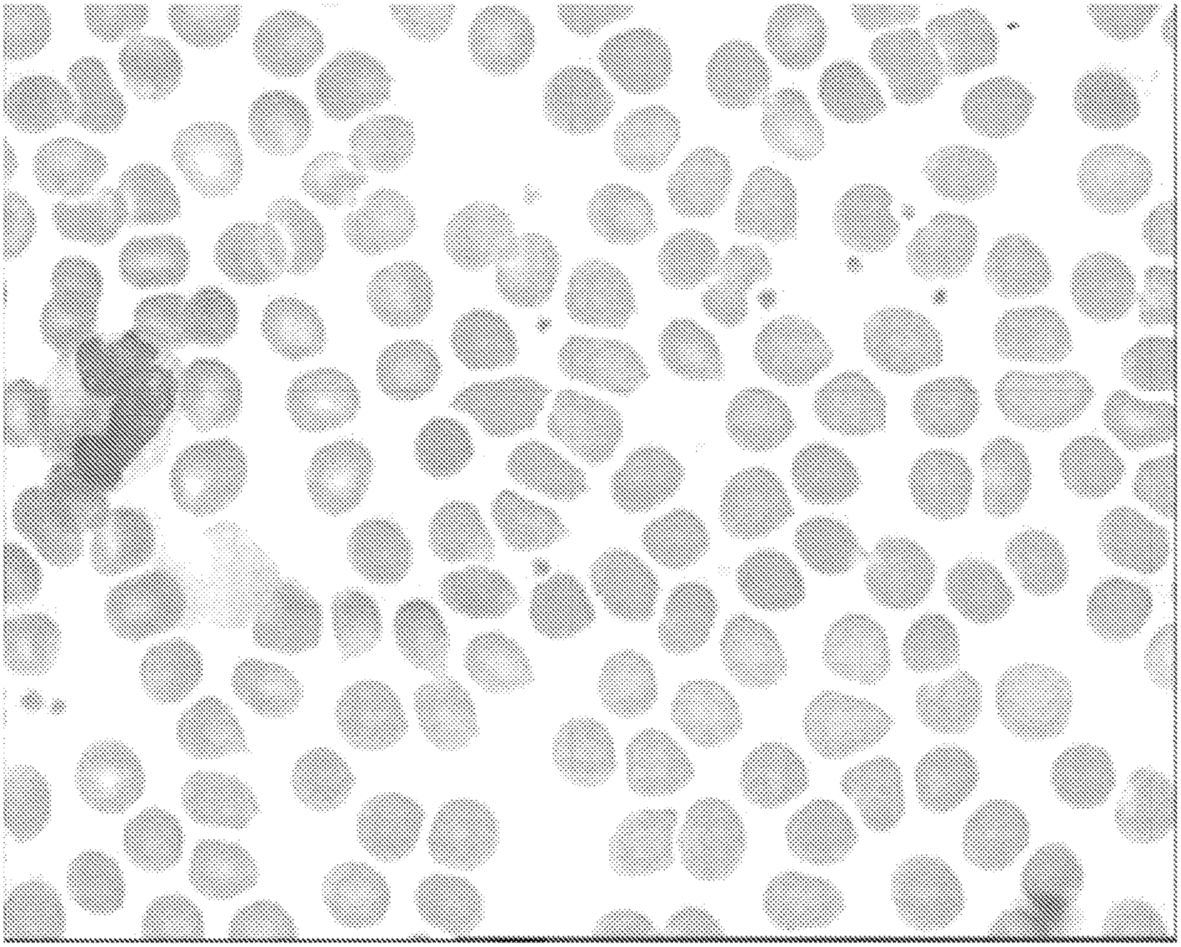
Figure 3O:
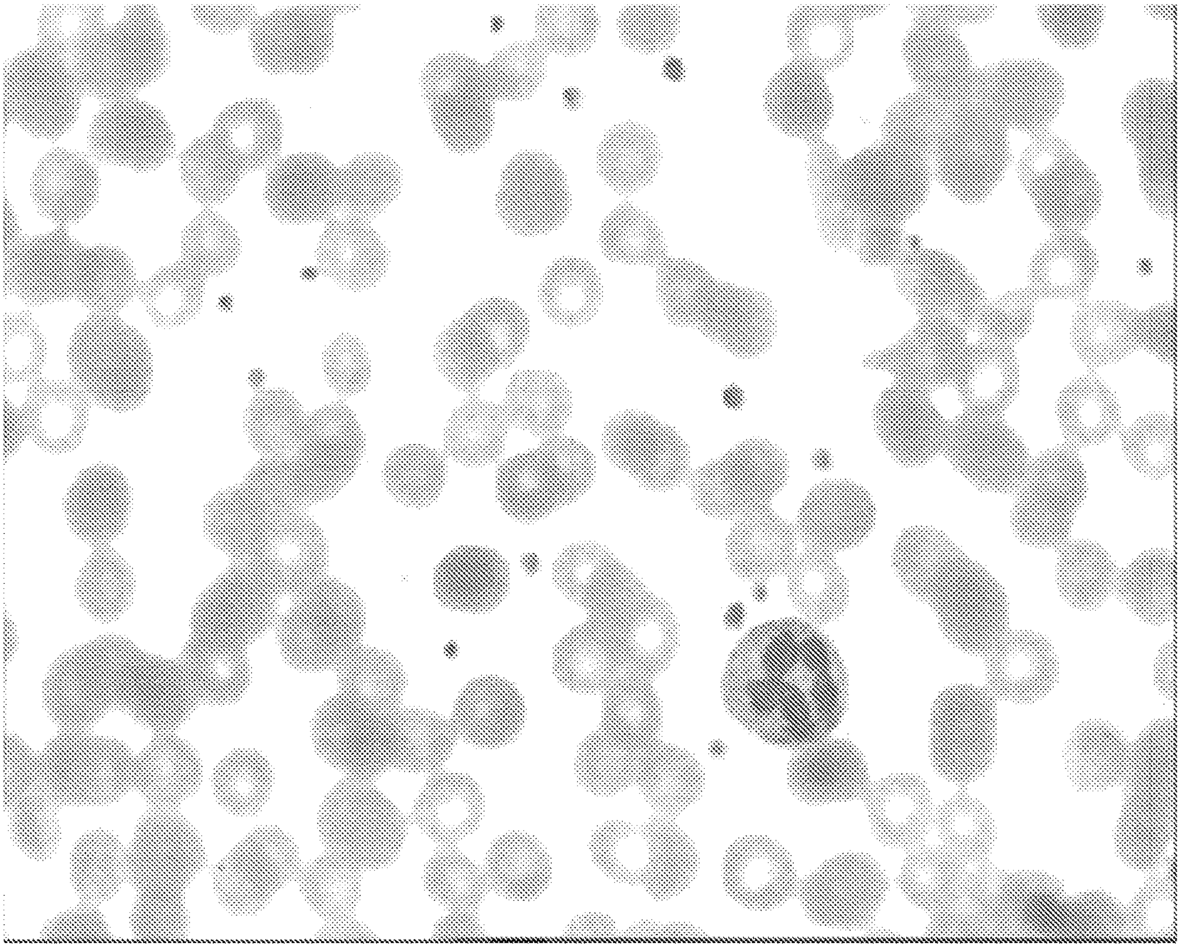
Figure 3P:
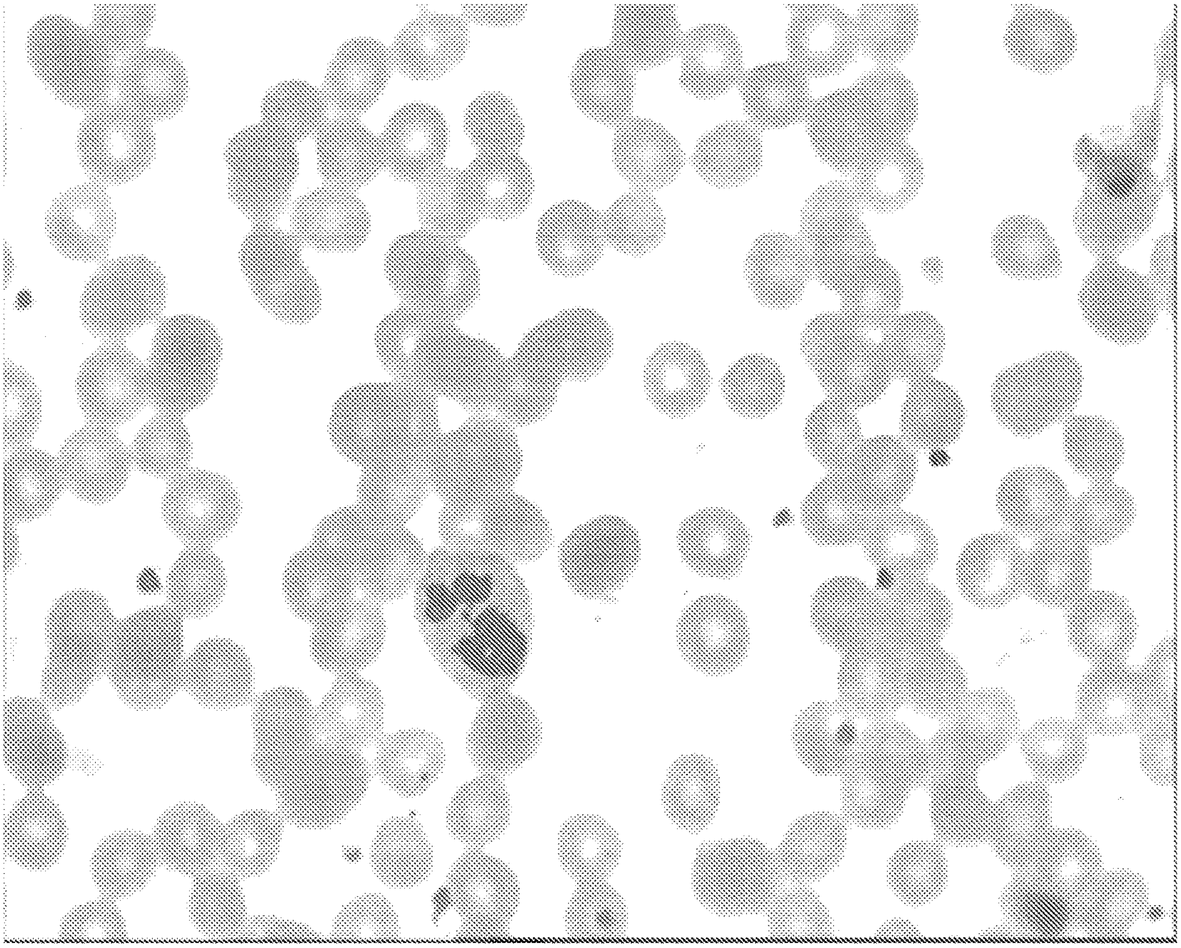
Figure 3Q:
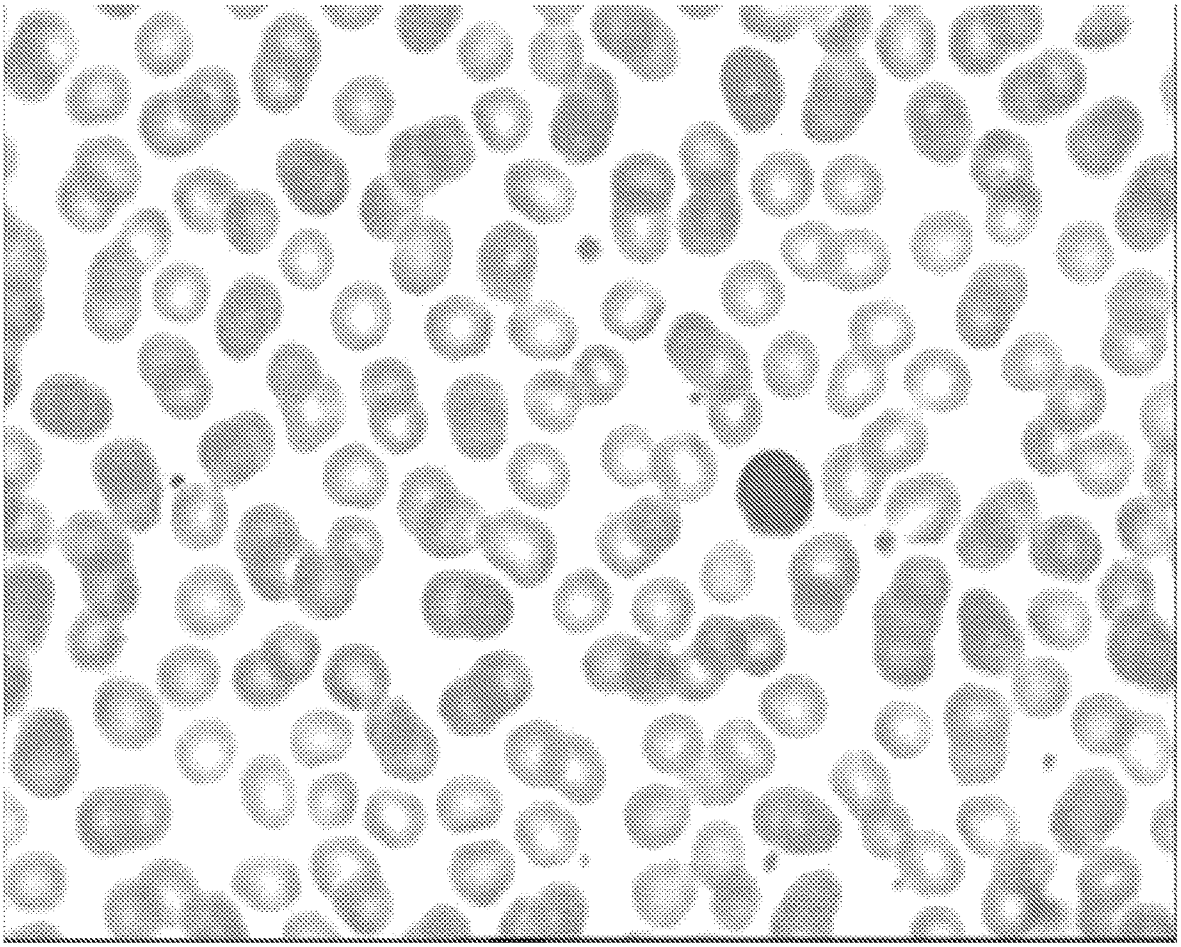
Figure 3R:
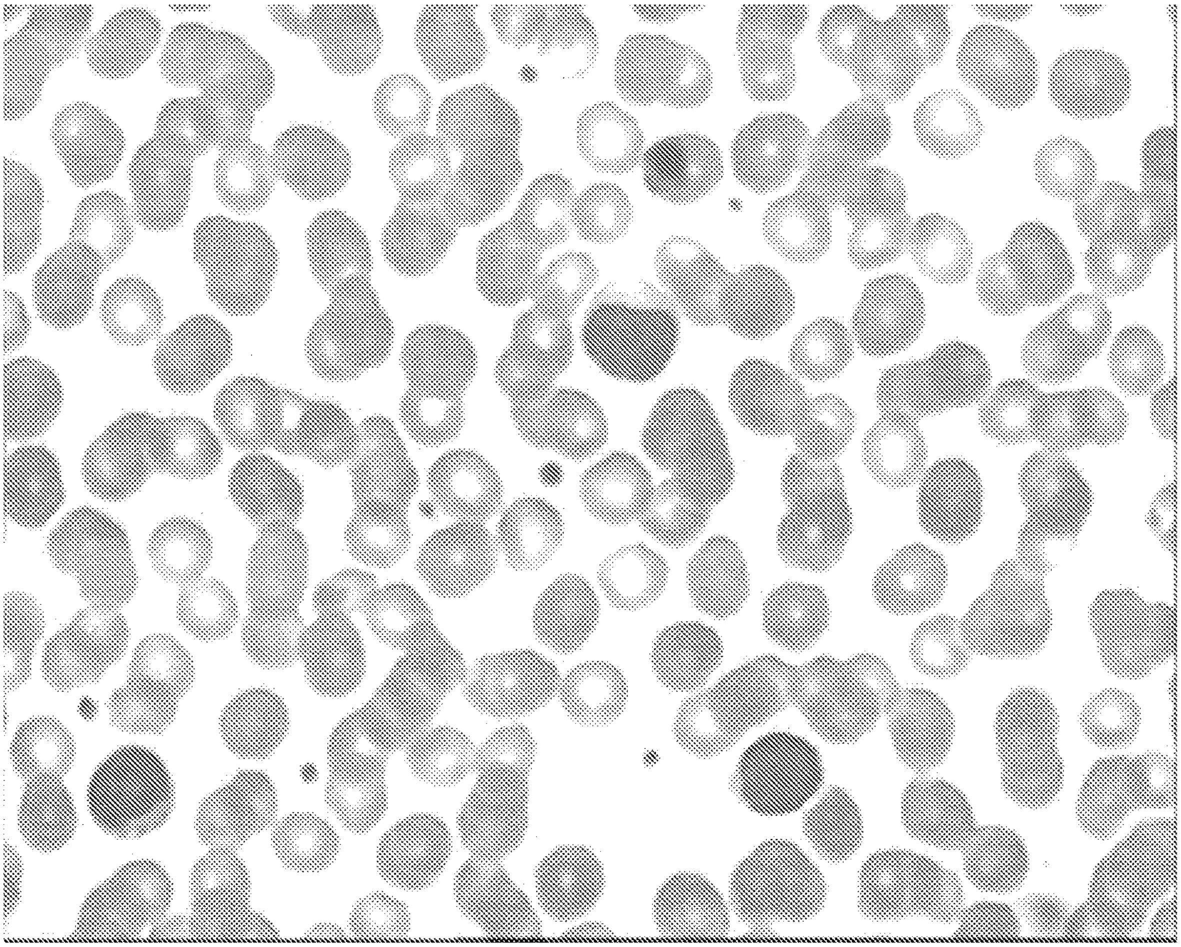
Figure 3S:
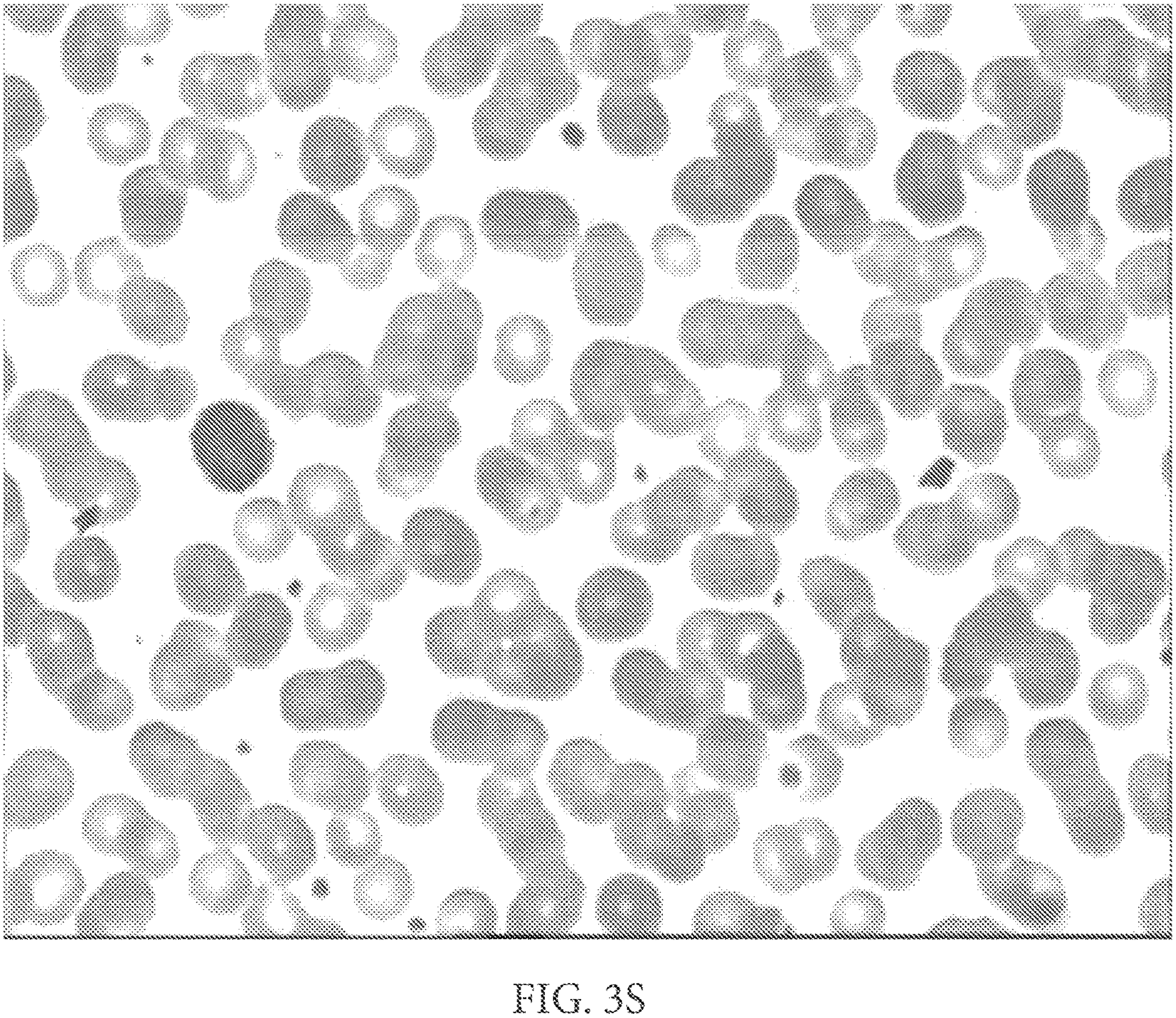
Figure 3T:
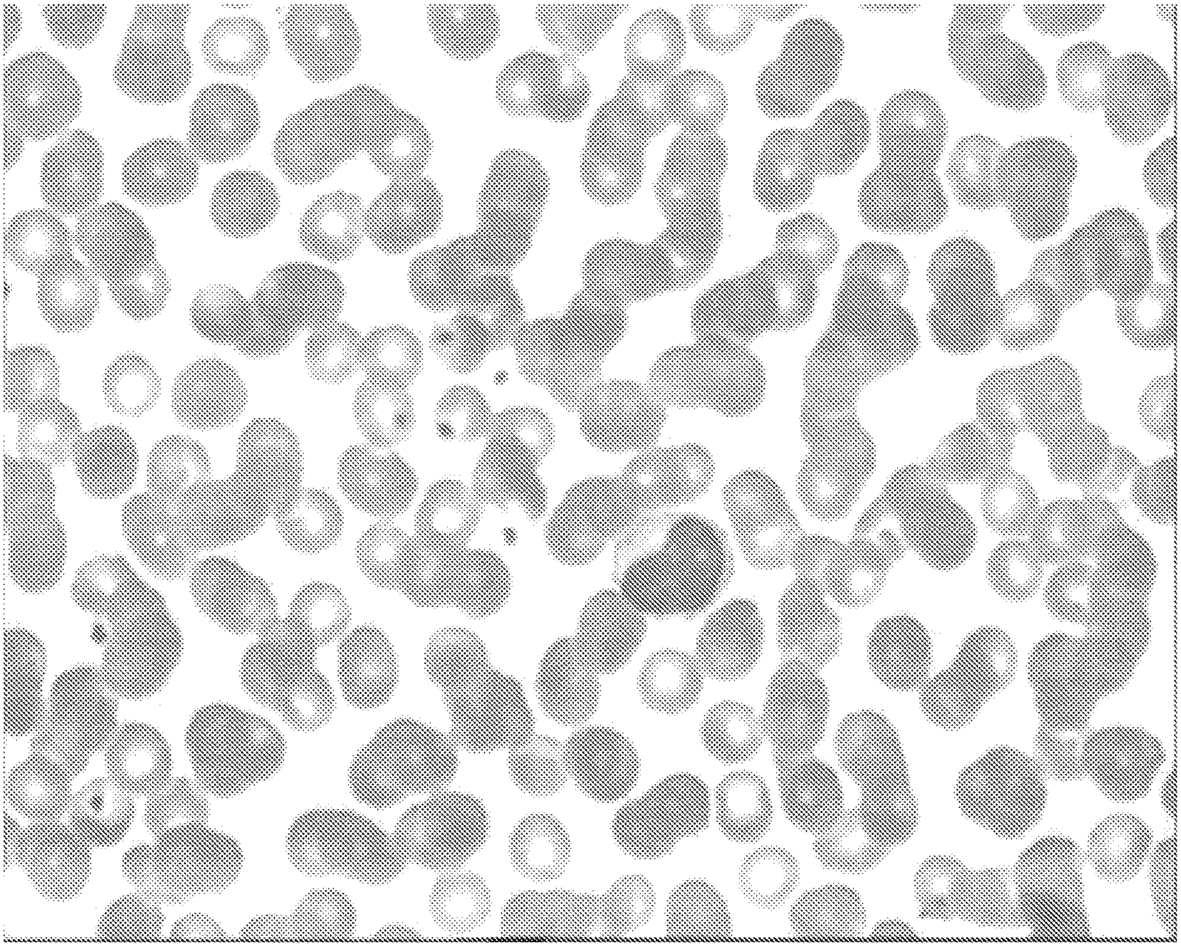
Figure 3U:
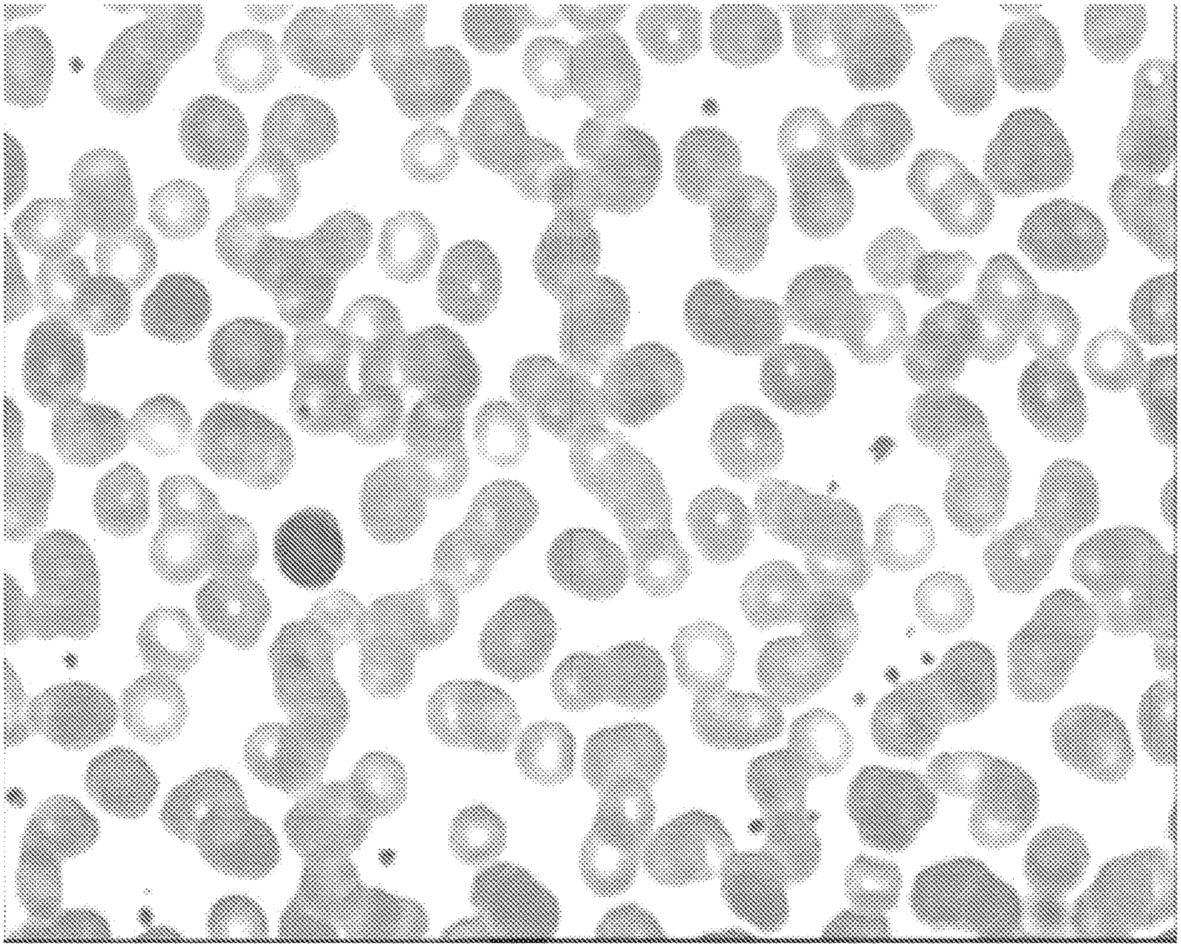
Figure 3V:
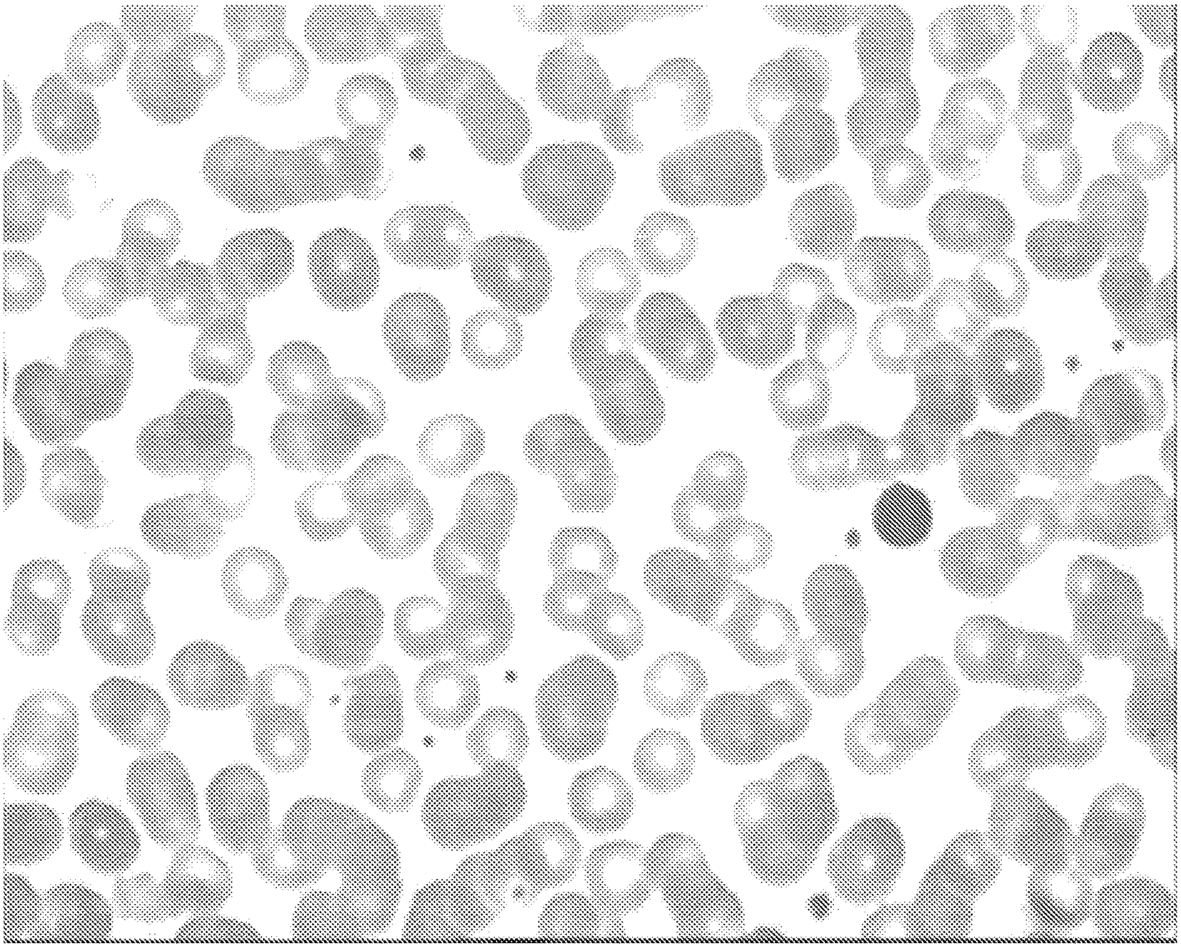
Figure 3W:
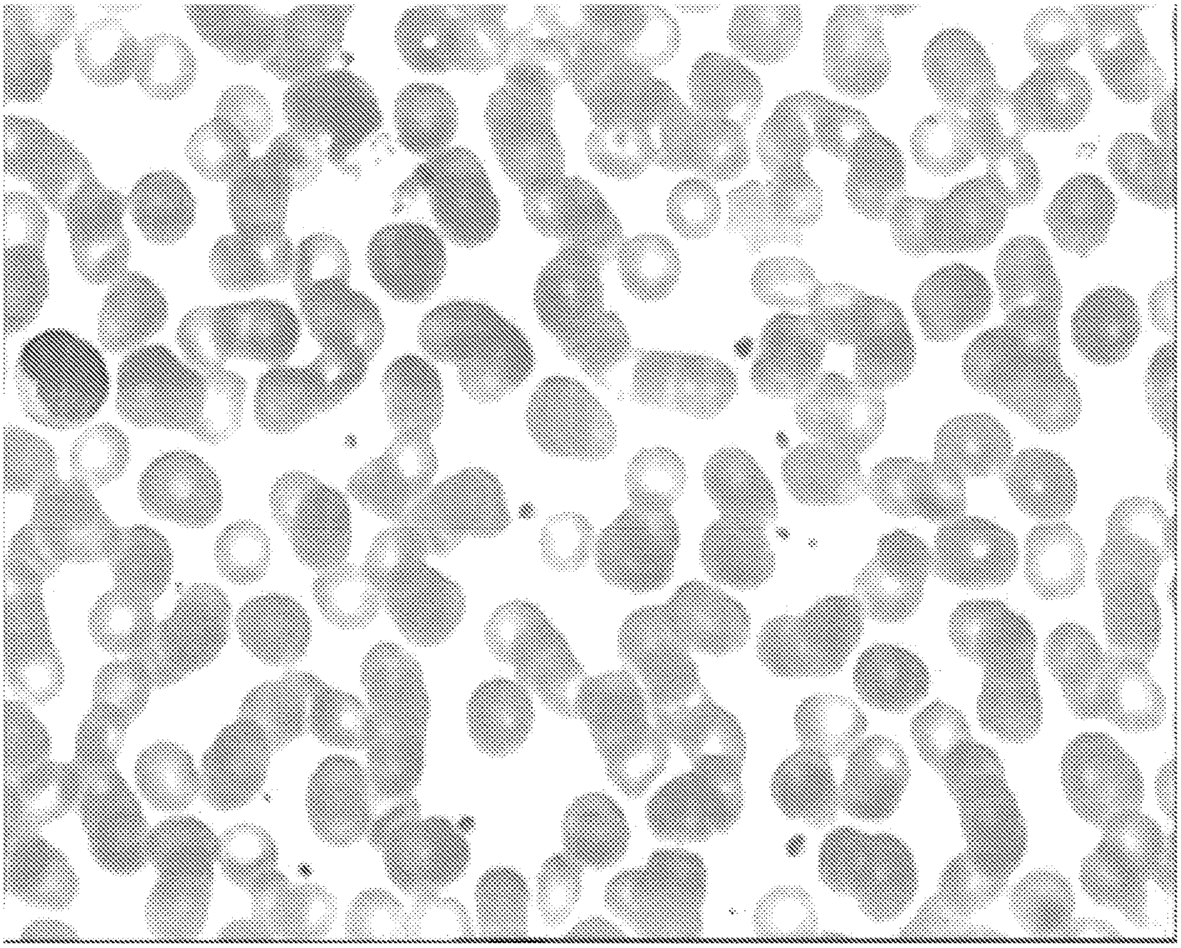
Figure 3X:
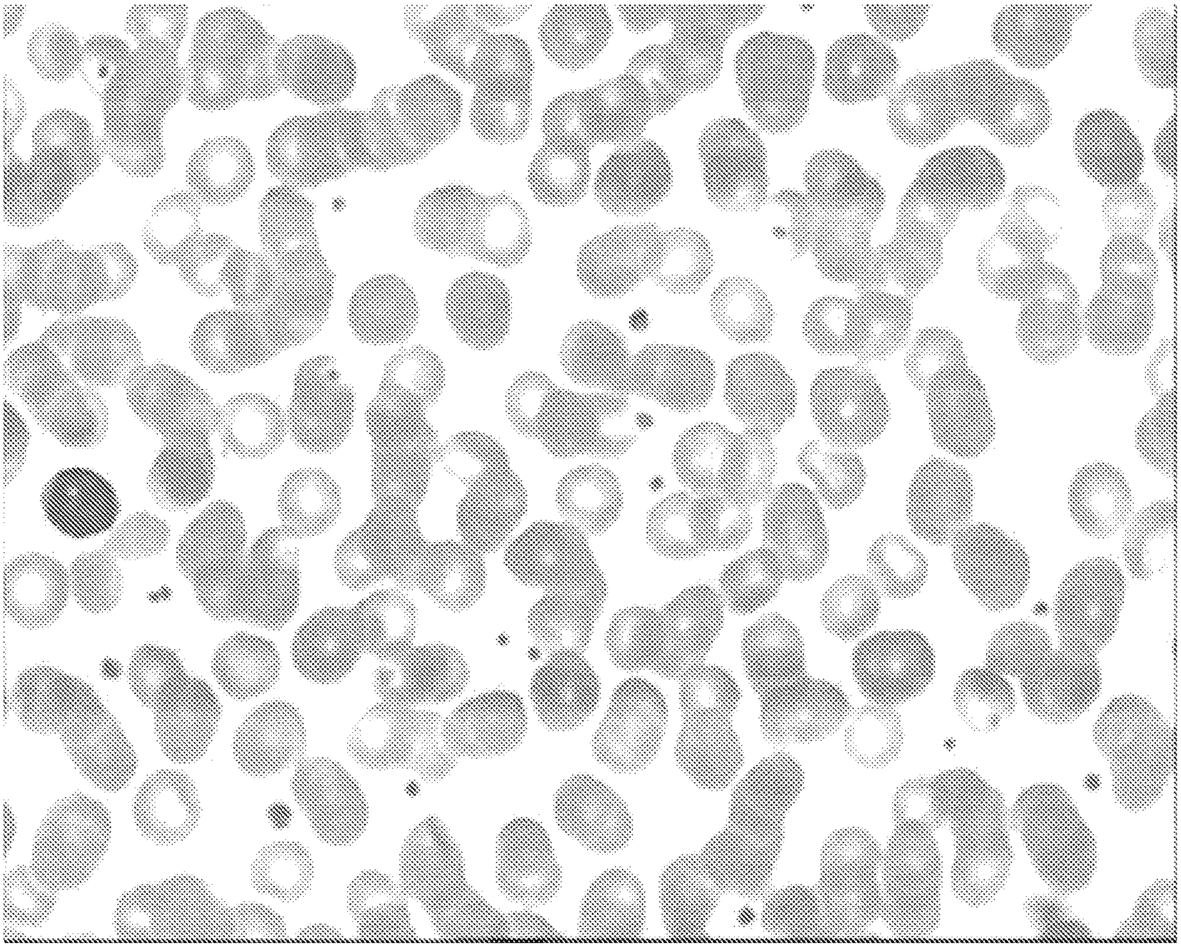
Figure 3Y:
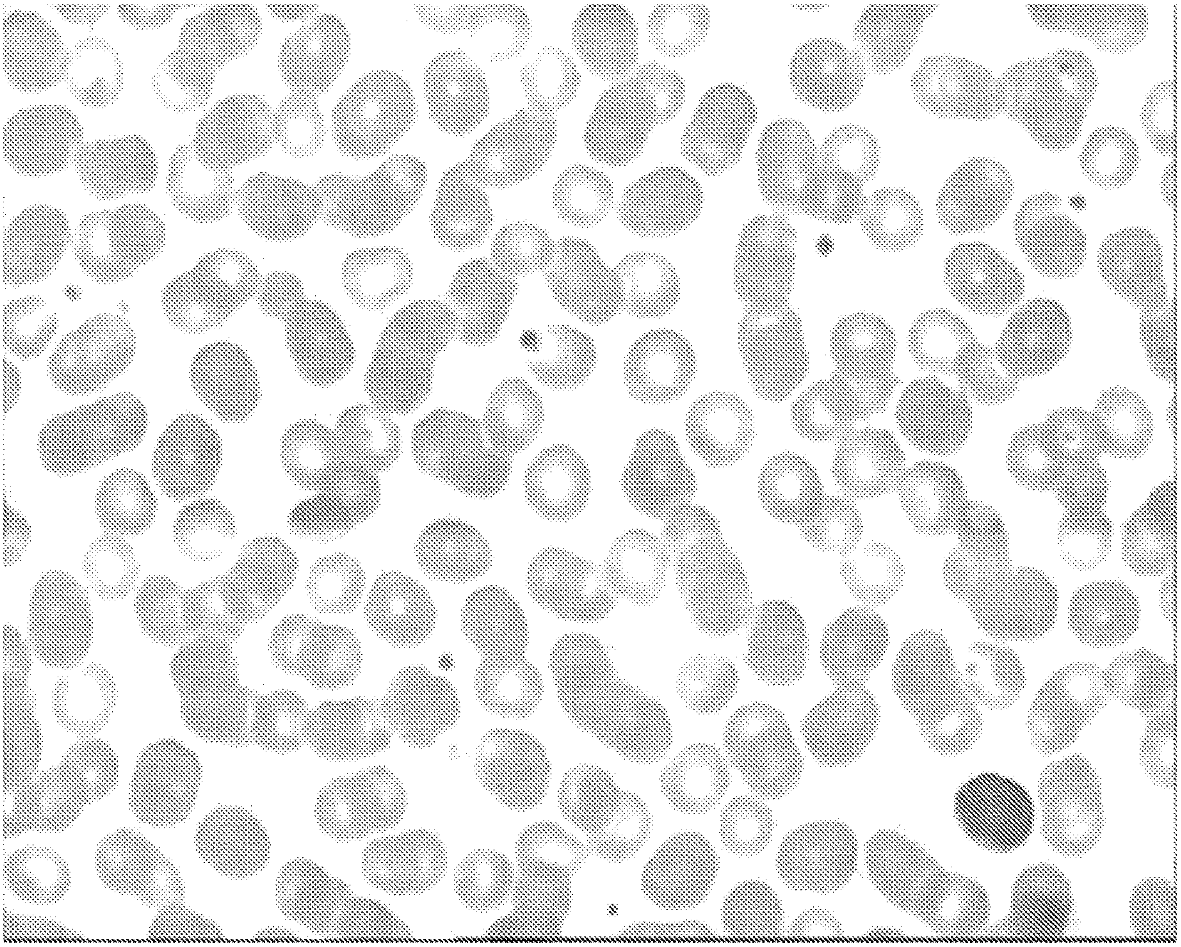
Figure 3Z:
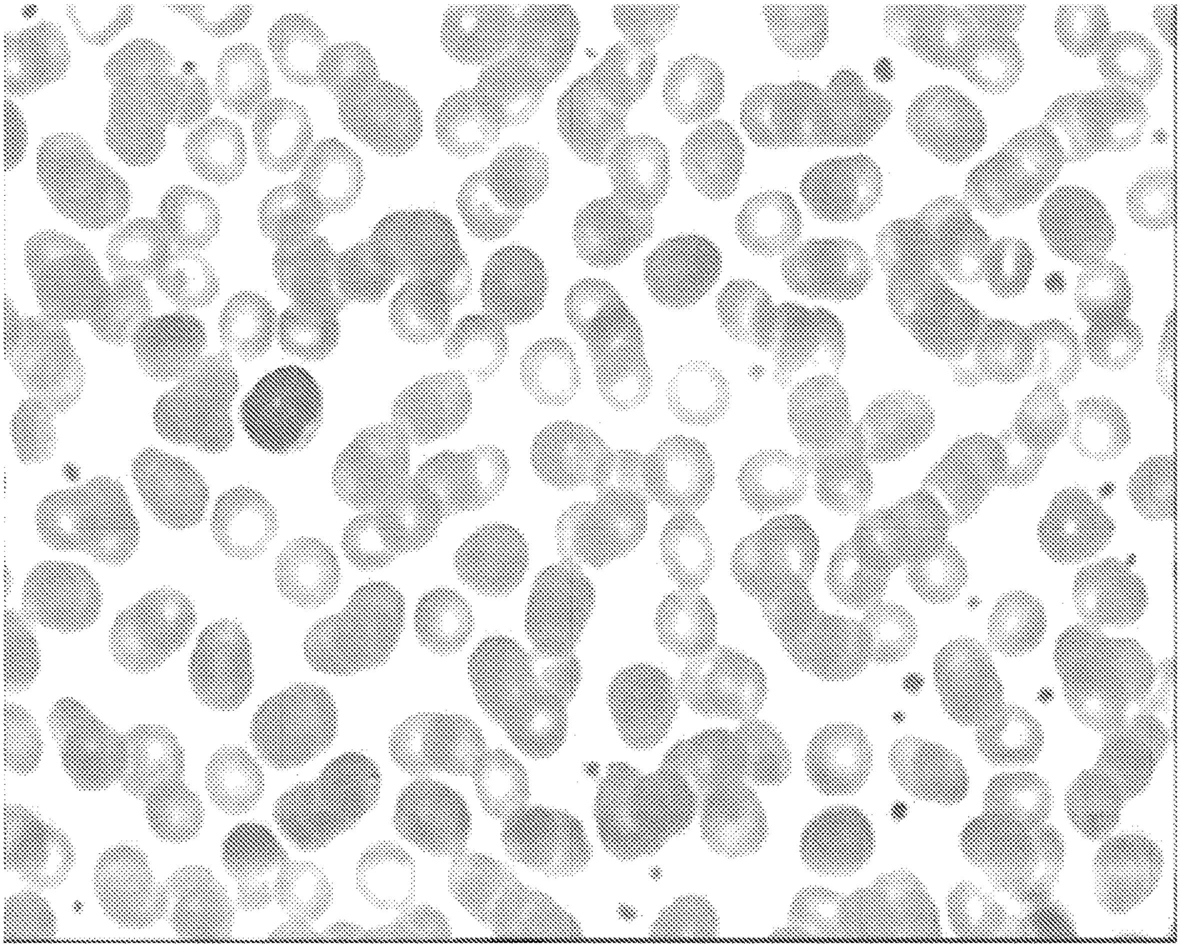
Figure 3A:
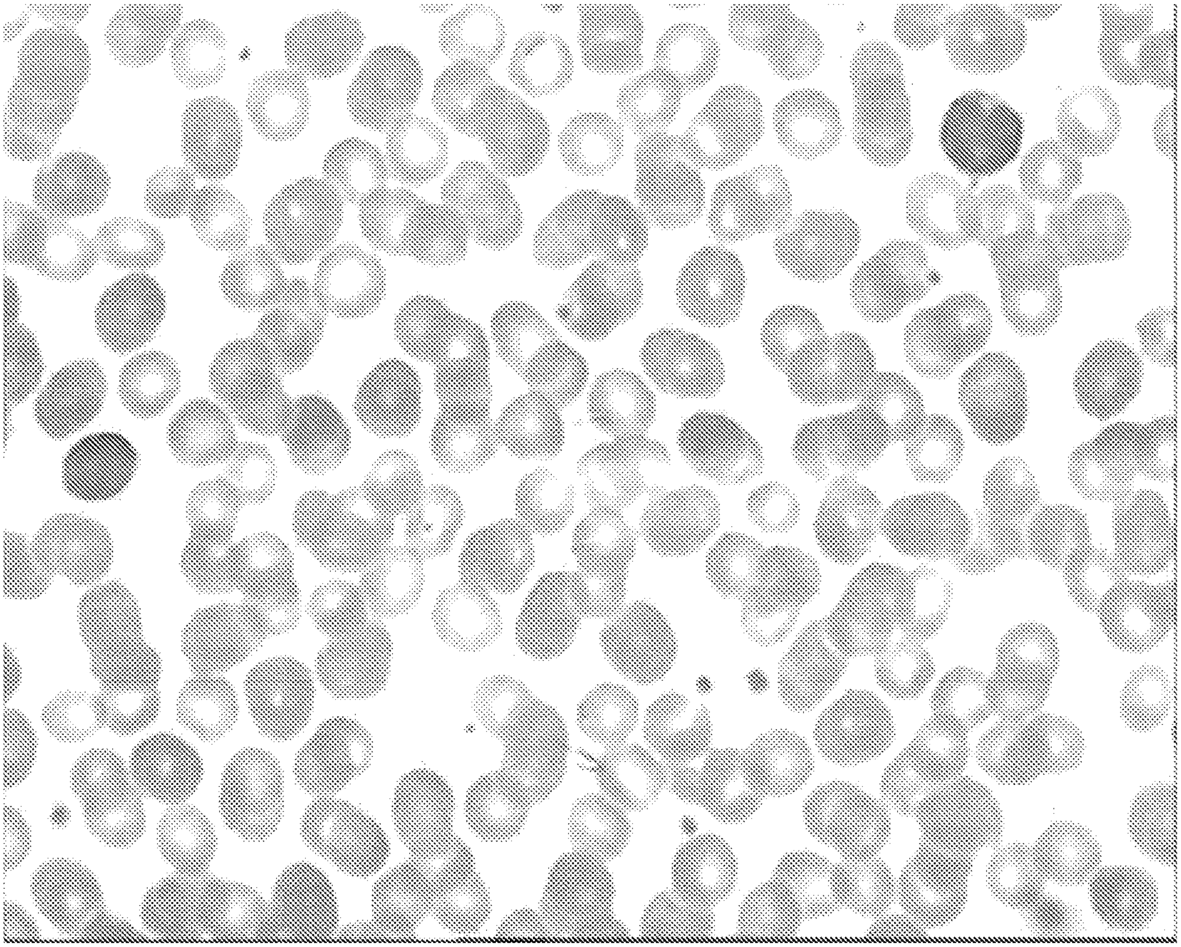
Figure 3B:
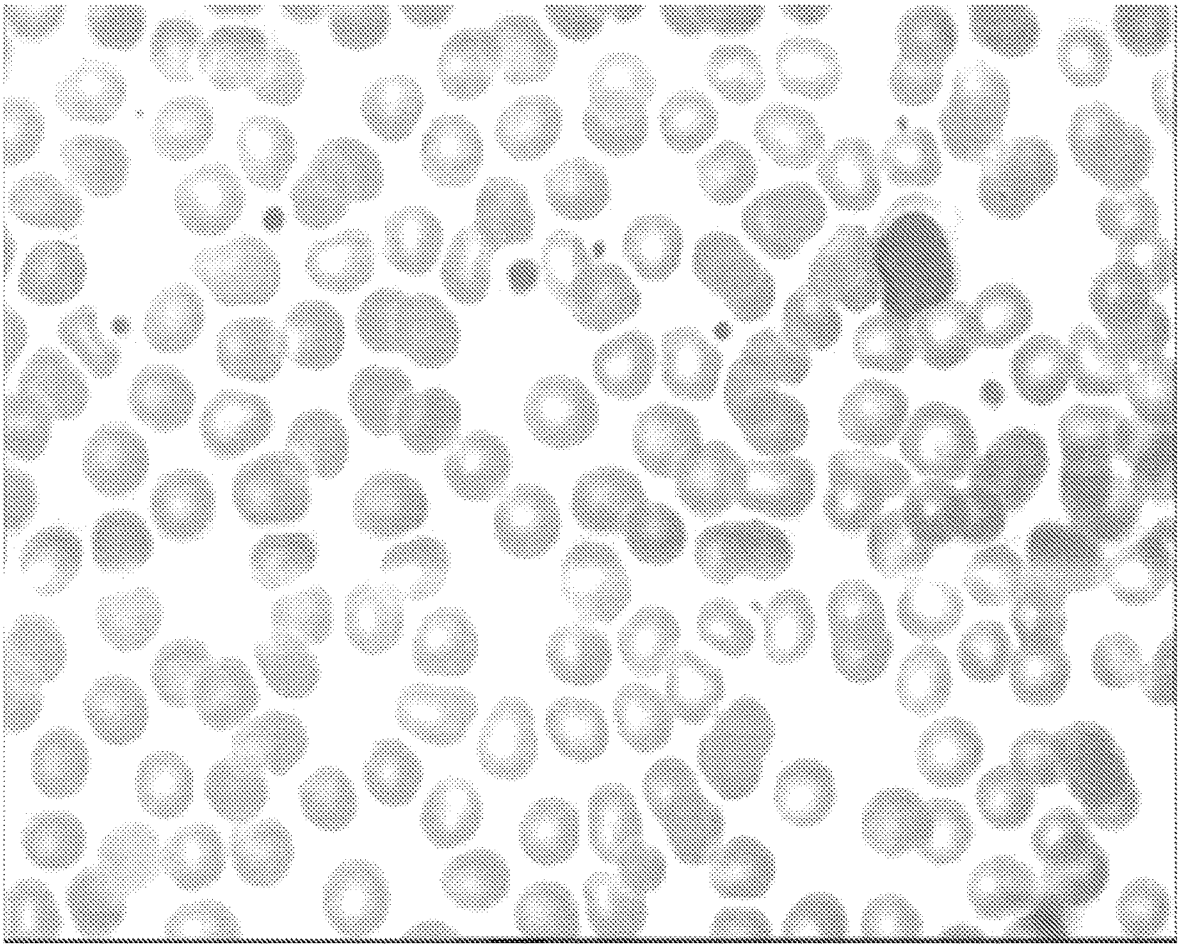
Figure 3C:
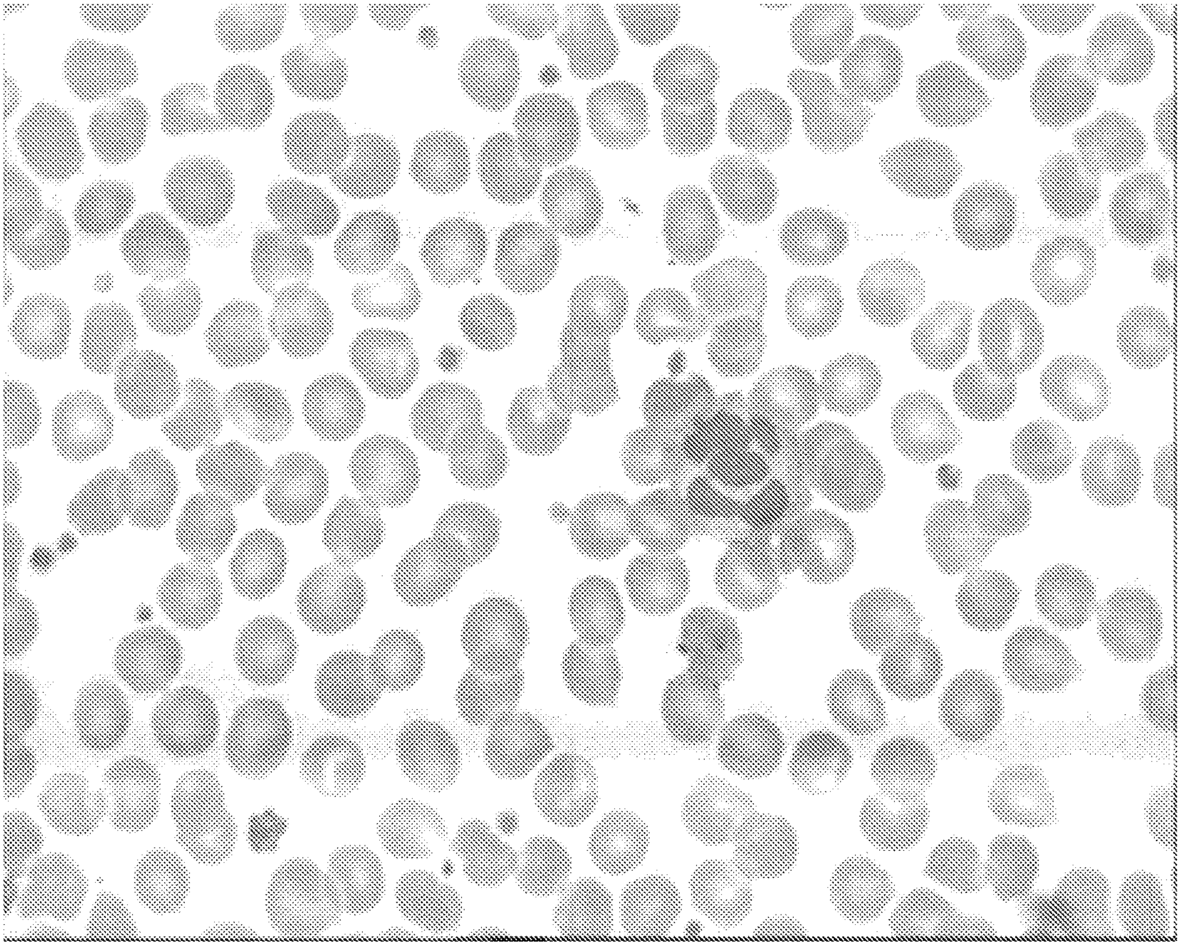
Figure 3D:
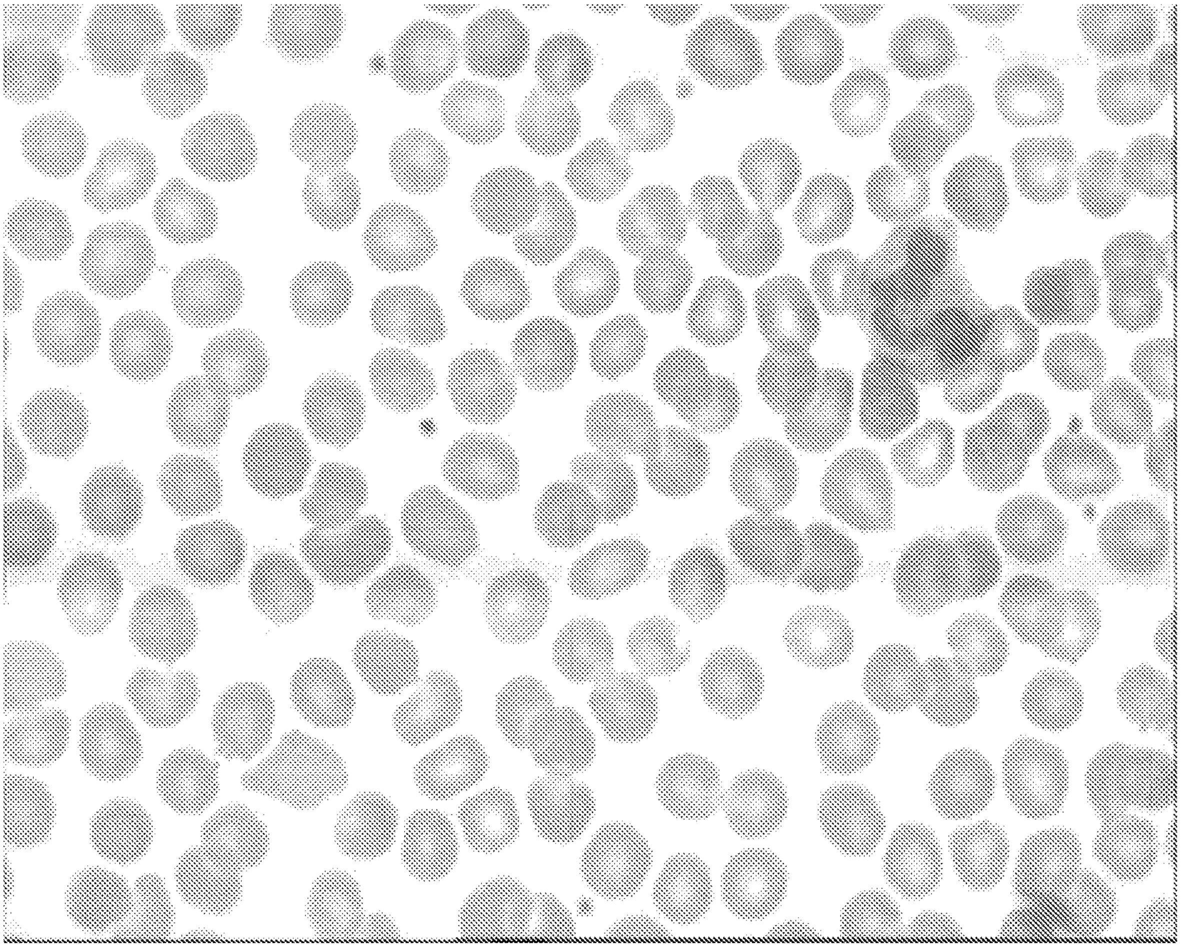
Figure 3E:
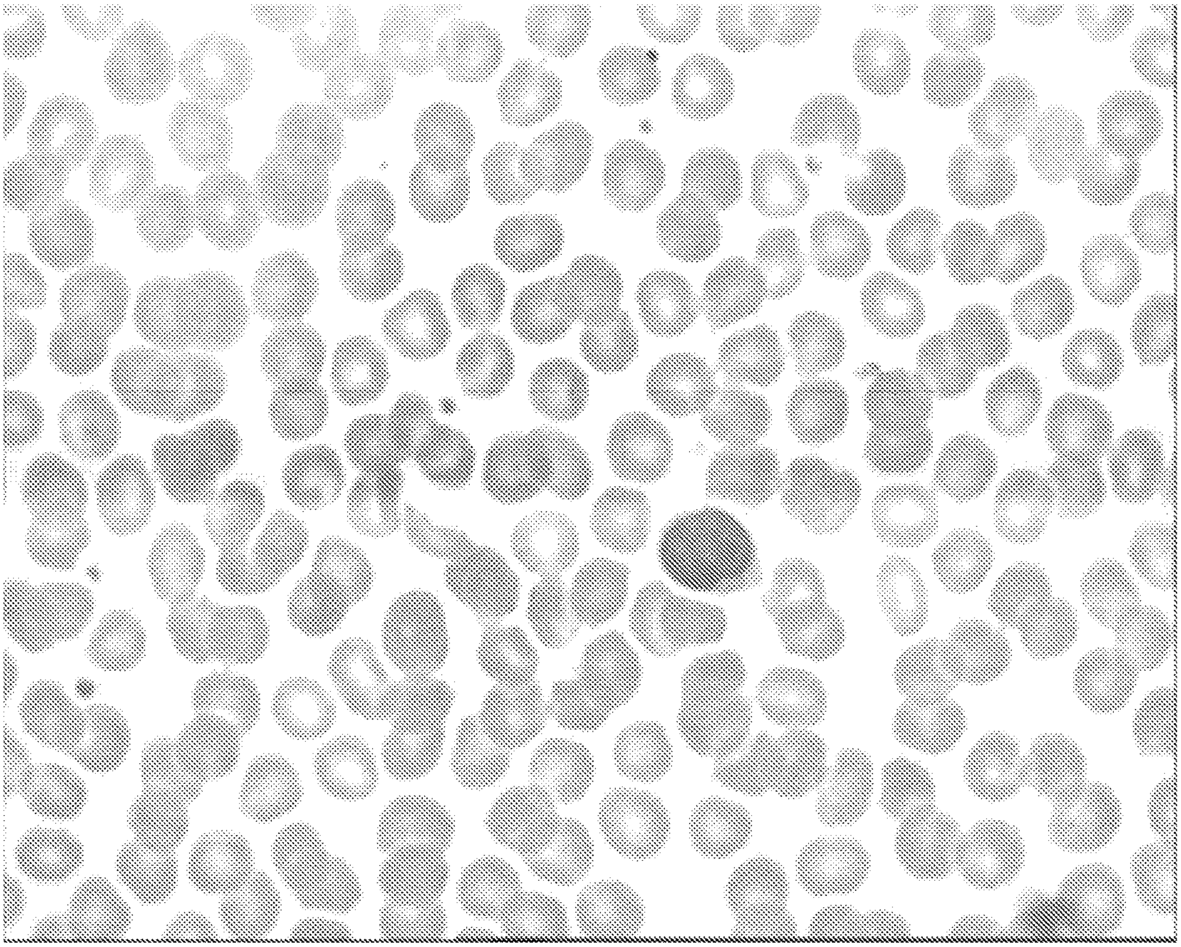
Figure 3F:
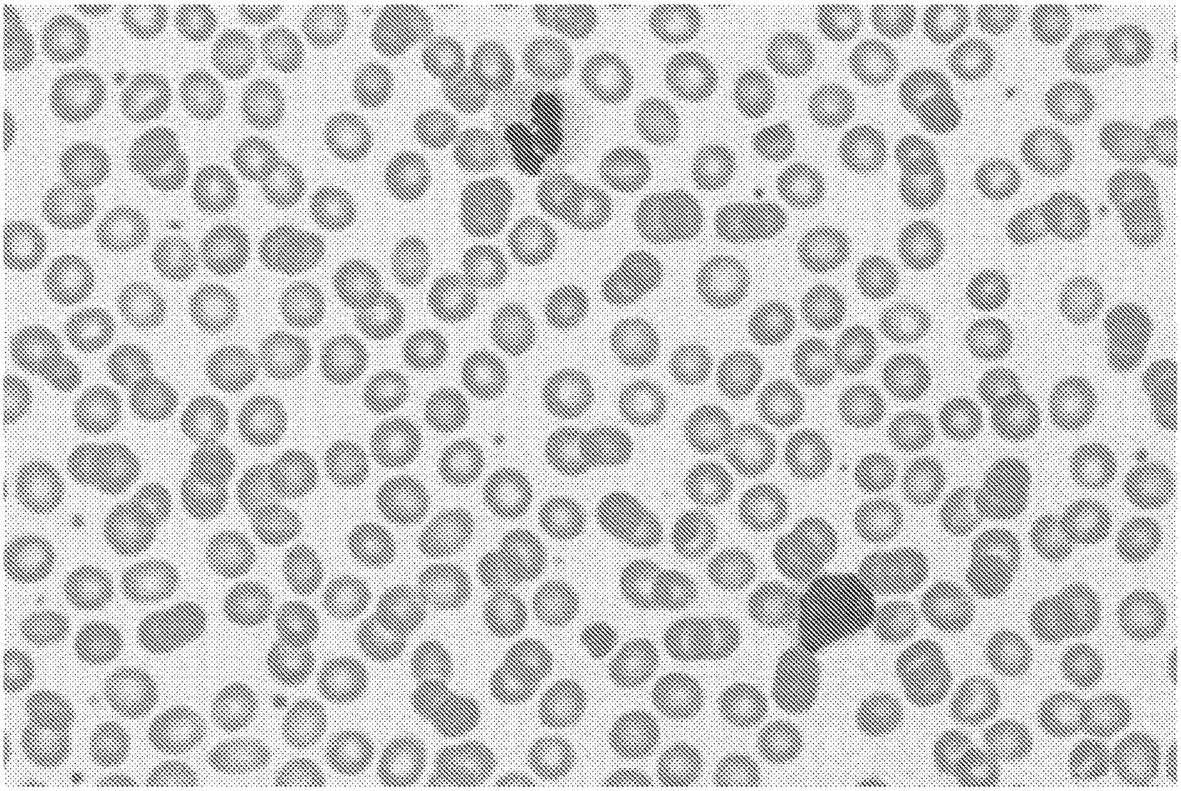
Figure 3G:
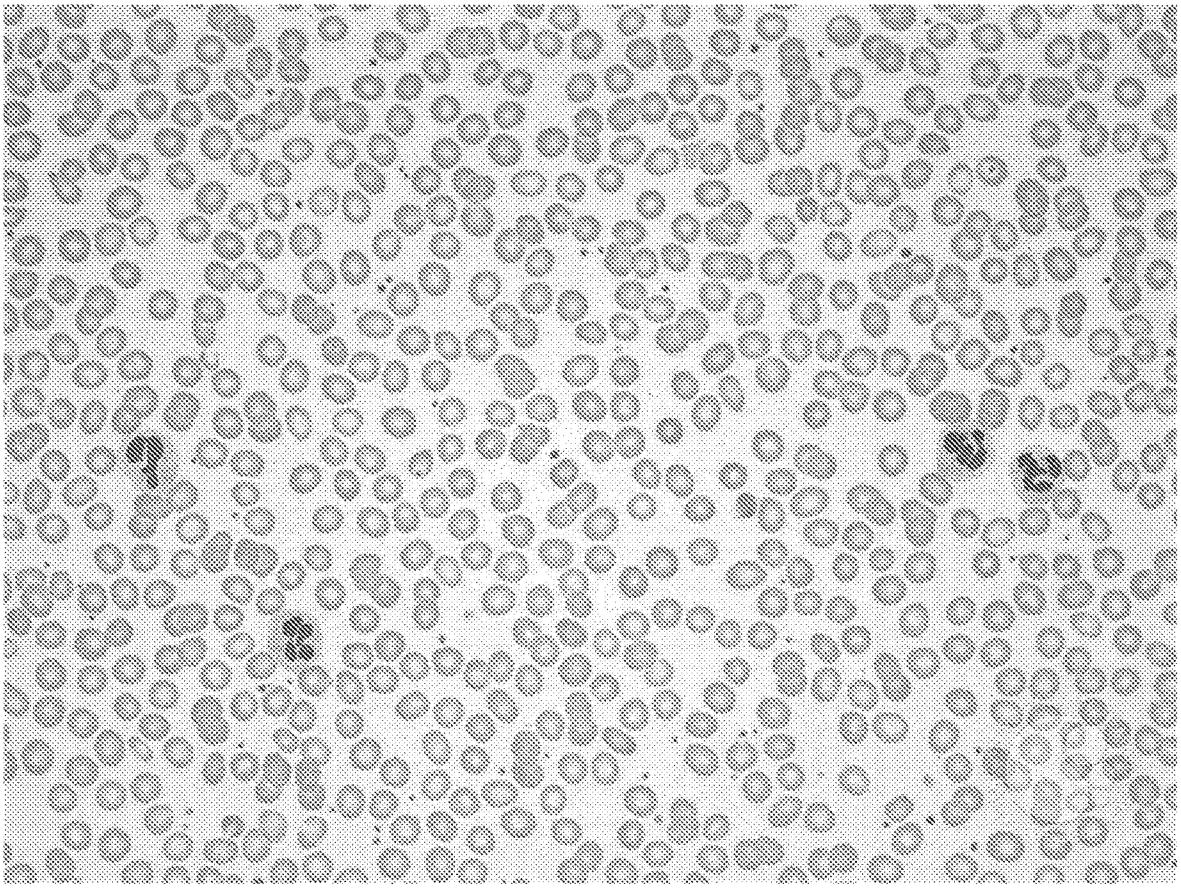
Figure 3H:
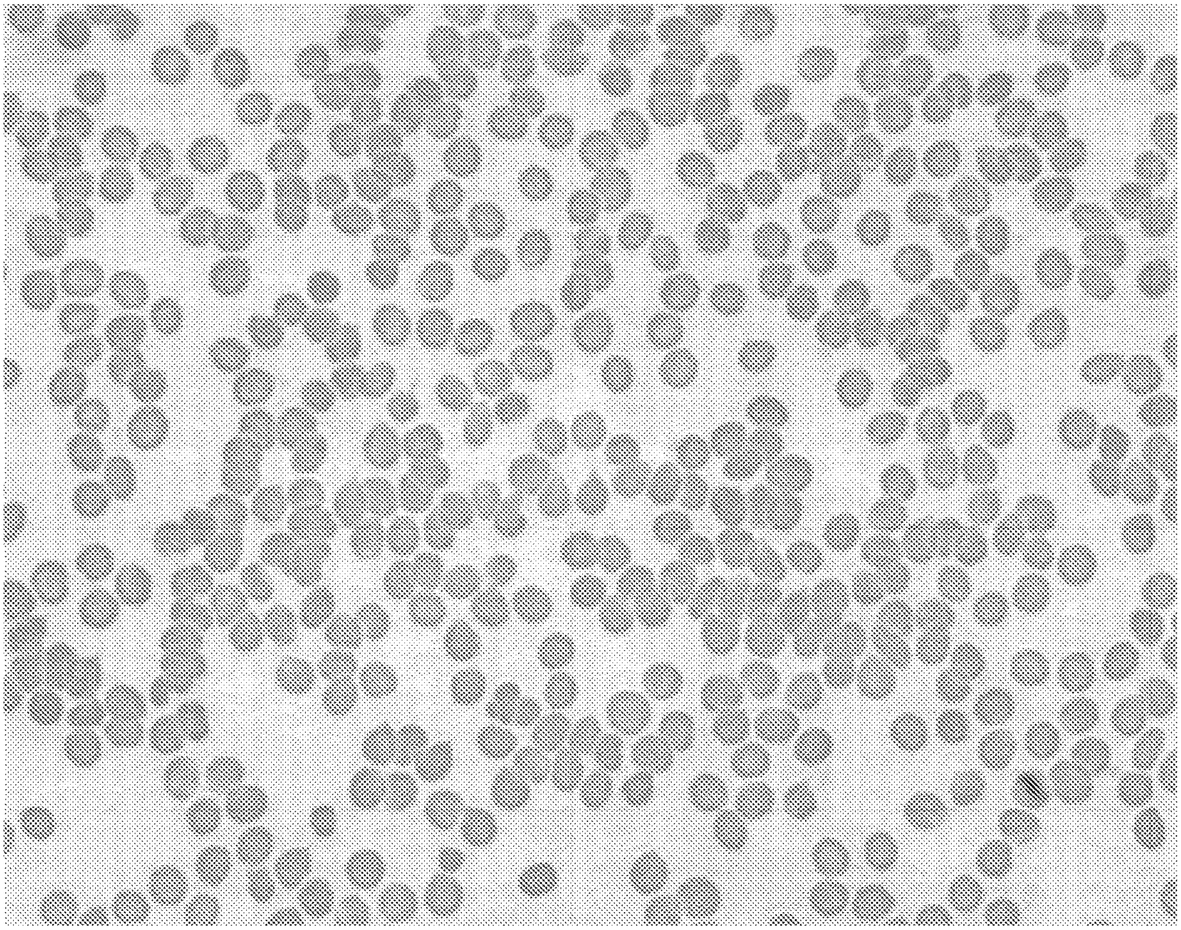
Figure 4A:
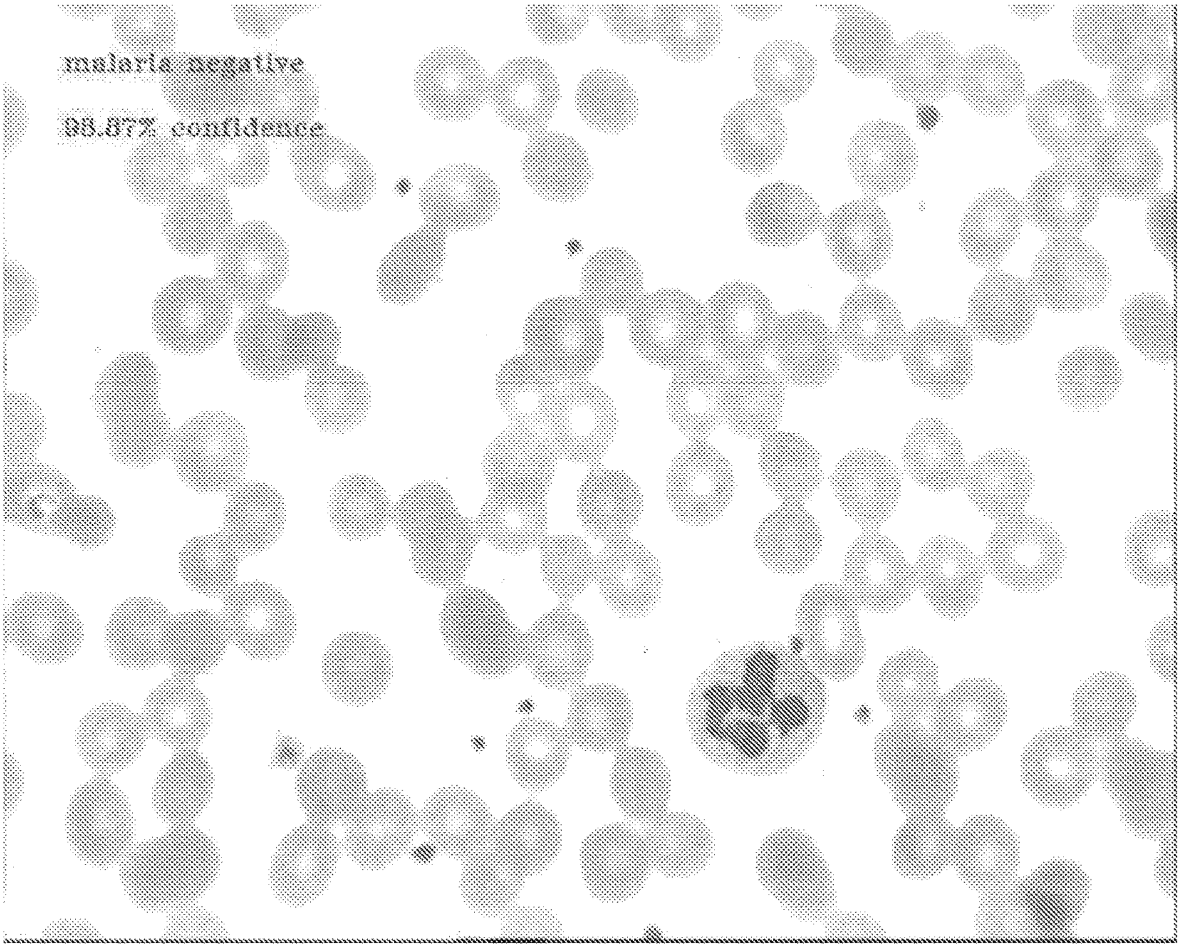
FIGS. 4A-4F are images used to test the trained ML algorithm with the inference label attached thereto.
Figure 4B:
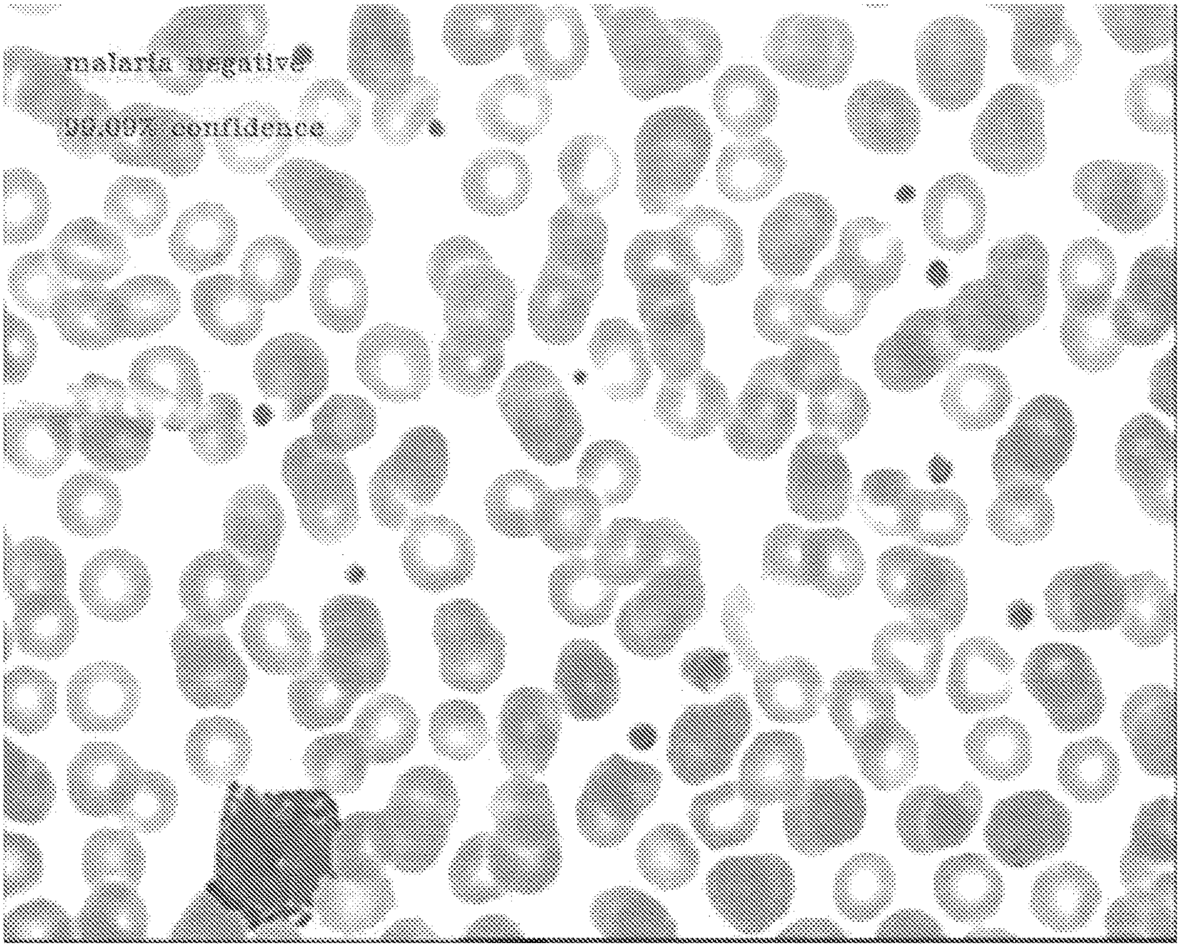
Figure 4C:
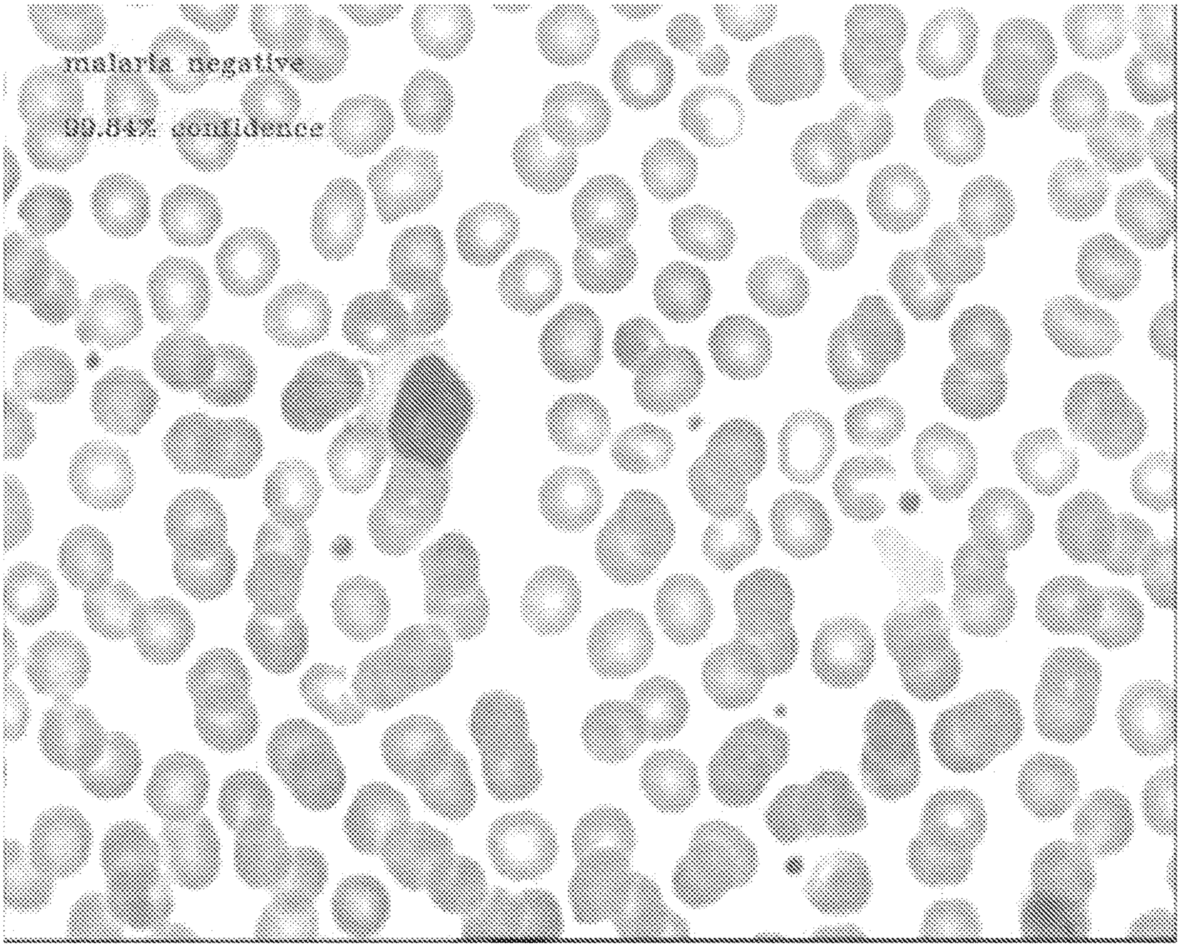
Figure 4D:
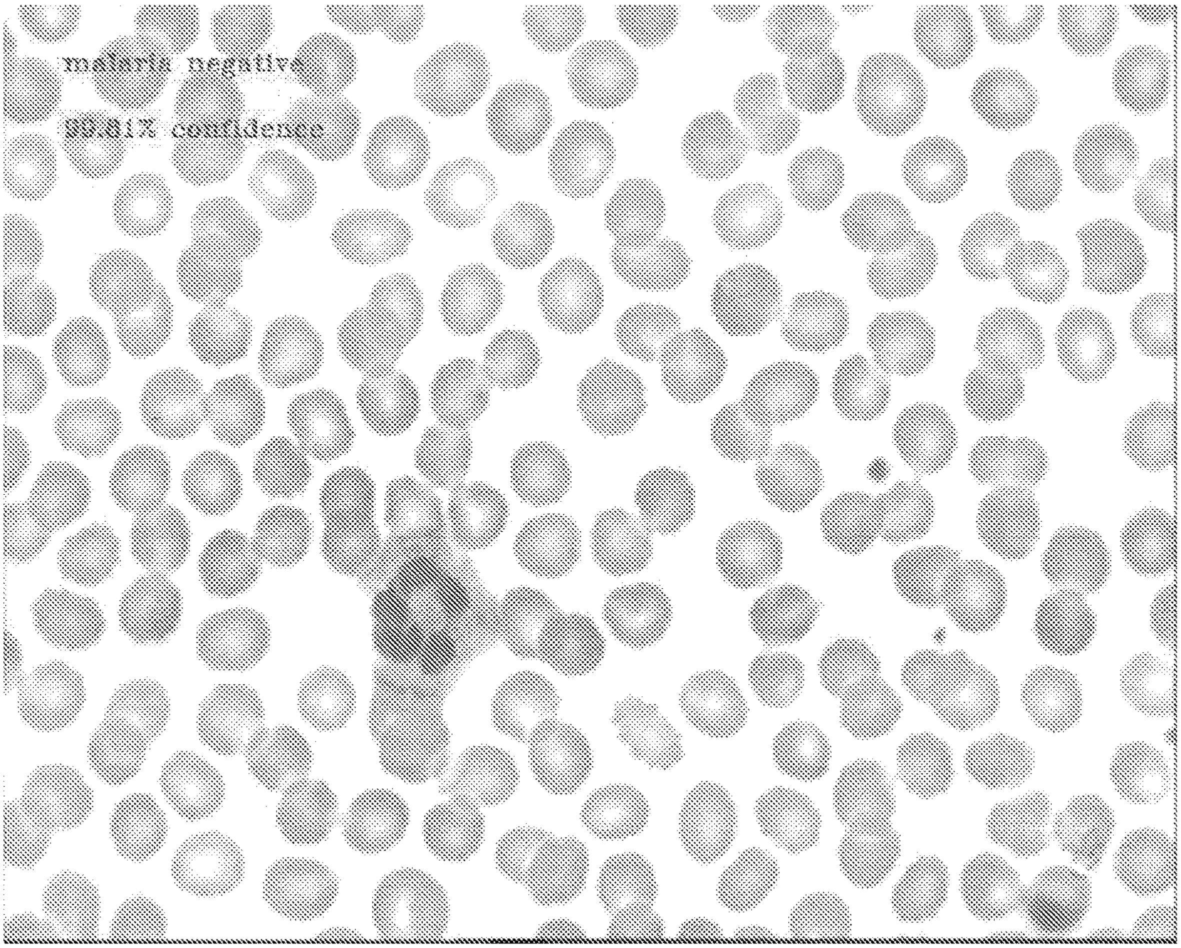
Figure 4E:
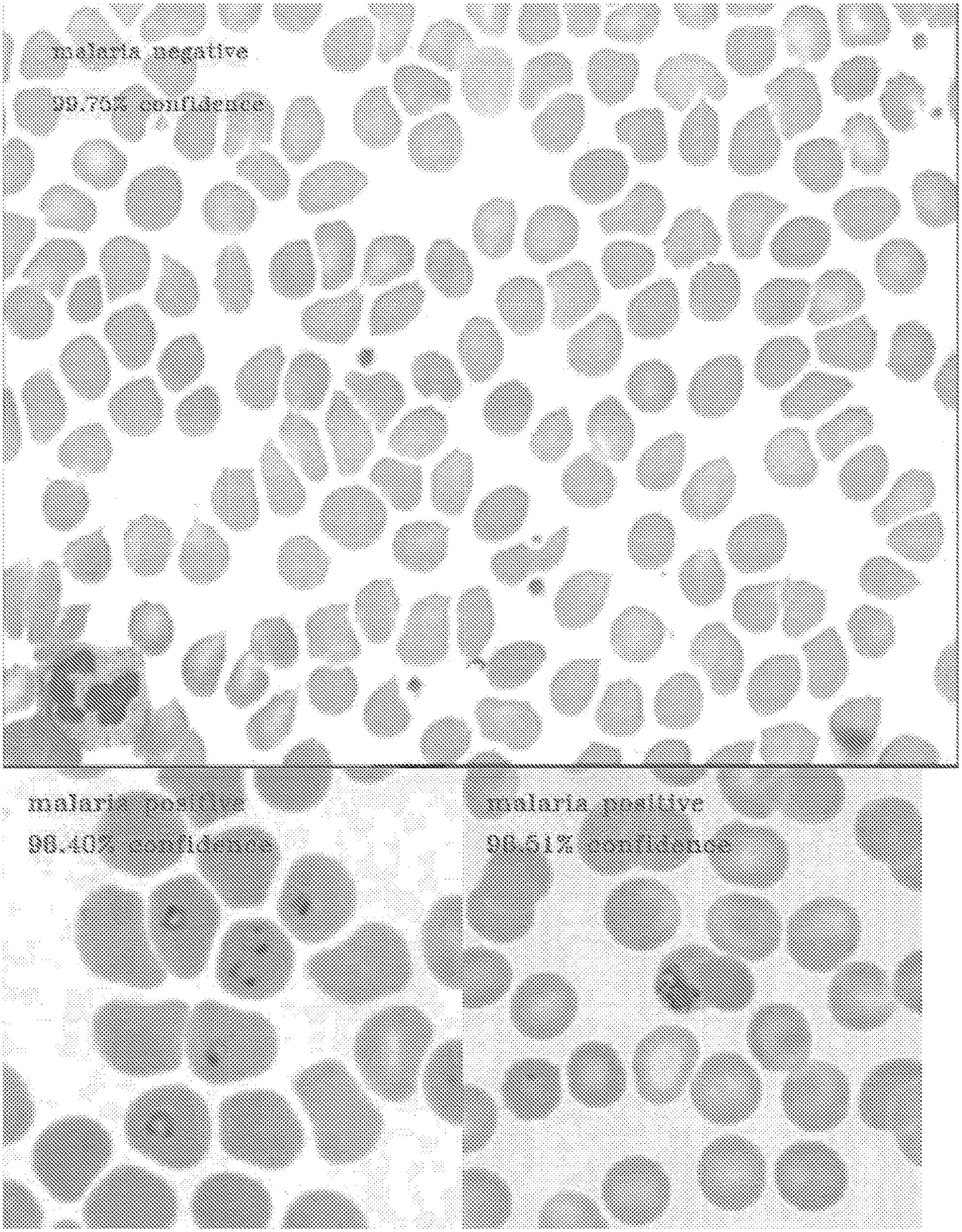
Figure 4F:
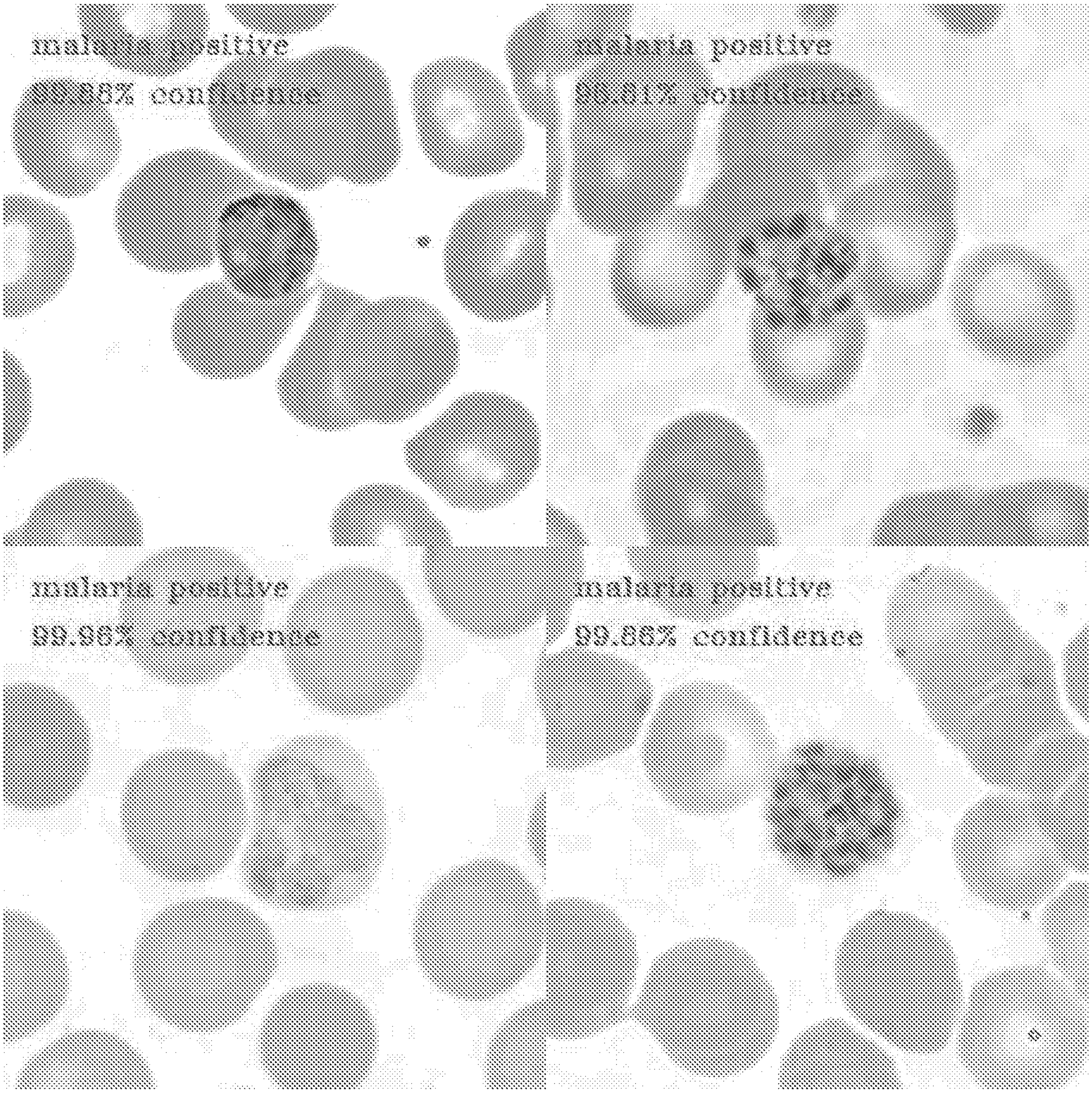

FIG. 1D is an illustration of an apparatus 100 for making a determination whether or not the malaria parasite is detected in a blood sample, wherein the ML code 116 is trained using a training set 114 of blood smear test strips. As shown in FIG. 1D, the apparatus may interface with a cloud network 118. The cloud network 118 can be used to obtain/download the ML code 116, receive data (including images) from the apparatus 100, and to communicate with health professionals located remotely from the location where the apparatus 100 is being used.

The training process comprises training ML algorithms 116 to classify stained blood sample images (e.g., 0=not infected; 1=infected). The training can be accomplished by performing supervised learning, where training images (stained blood samples) 114 are provided to the ML algorithm, where the training images 114 are correctly labeled beforehand by an expert pathologist (0=not infected; 1=infected). The ML algorithm 116 learns from the training data 114 and, after learning, makes inferences on new images based on its training. The new image is then classified (e.g., 0=not infected; 1=infected).

In one example, the ML code 116 comprises modified code from Google's open source ML library known as Tensorflow and OpenCV for handling images. Tensorflow is operated using Python and the IDE Spyder. The exemplary ML code 116 comprises a neural network. In one example, the neural network code was trained using images of (known) malaria positive blood samples (see, for example, FIGS. 2A-2J) and images of (known) malaria negative samples (see, for example, FIGS. 3A-3HH). In this instance, the malaria positive images were obtained from the CDC website and the malaria negative images were obtained from the LISC database. To improve the accuracy of the algorithm, at least some of the uninfected images (FIGS. 3A-3HH) contained various leukocytes (such as a neutrophil) that could produce false positives.

In one non-limiting example, the particular neural network being trained is the Inception v3 network. The training set comprised 10% of the training images and another 10% of the training set were taken to be the validation set. The training was run for only 500 steps at learning rate of 0.01. After the training, inferences were executed and eleven images containing both infected and uninfected samples were examined. The trained ML code returned 100% accurate results with high confidence (minimum 98.40%). The images with the inference label are attached hereto as FIGS. 4A-4F.

In one aspect, successively coarser images of the same blood sample are used to train the ML code 116 so that it only needs an image of a blood sample taken with an ordinary smartphone camera with no need for a microscope attachment 112 or magnification. This feature provides a significant advance over the state-of-the-art. Typically, this strategy for training the ML code: obtaining successive images of the same blood sample at different magnifications ranging from fine to coarse, which are used to train the ML code. The ML code is thus trained to be accurate in interpreting images generated at the coarse levels using a cell phone attachment—this ML training strategy advantageously results in a compact imaging attachment or compartment.

Figure 5A:
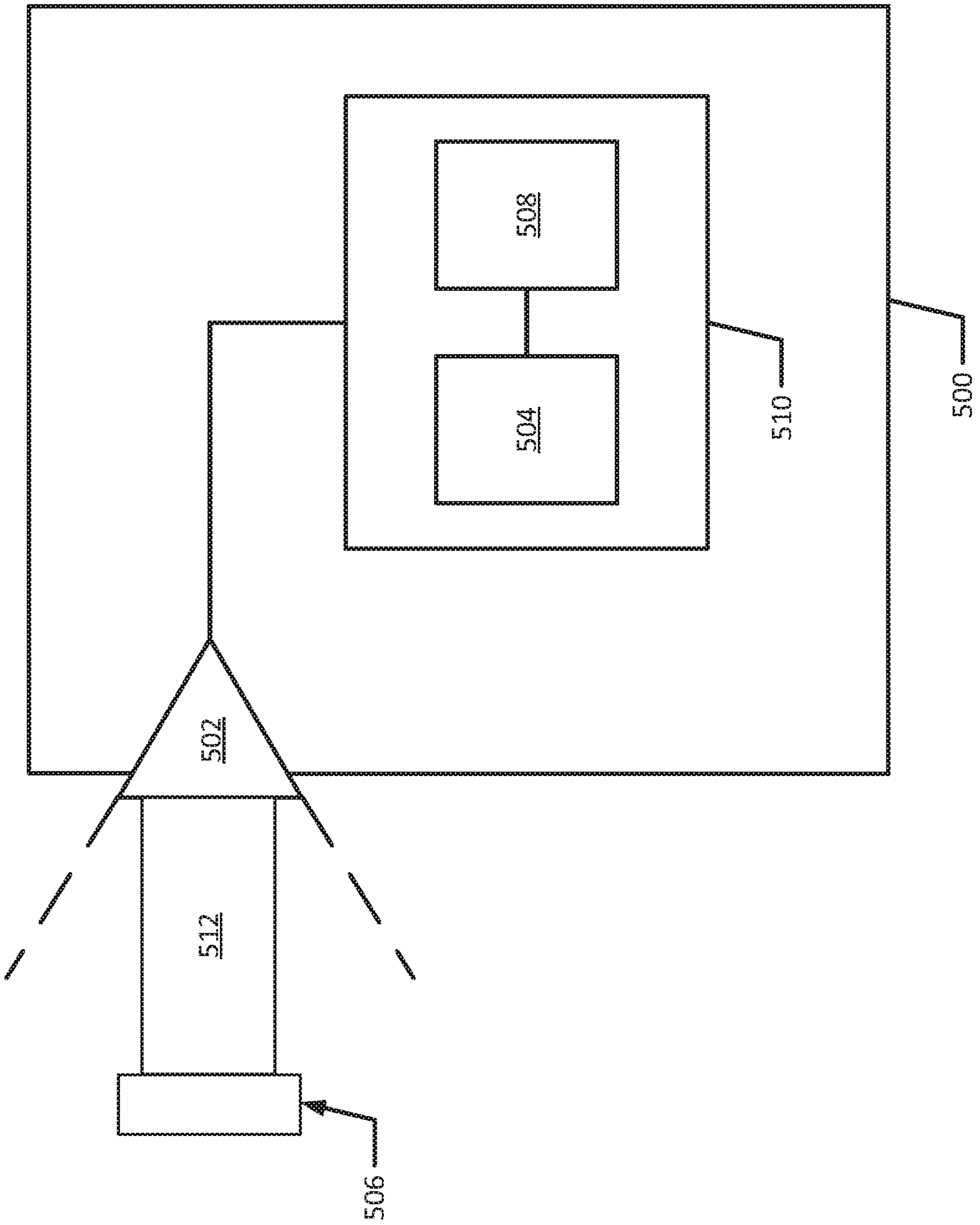
FIG. 5A illustrates another embodiment of an exemplary overview apparatus for making a determination whether or not the malaria parasite is detected in a blood sample.

FIG. 5A illustrates an embodiment of an exemplary overview apparatus for detecting *Plasmodium* parasites in a blood sample. In one aspect, the apparatus 500 uses a Polydimethylsiloxane (PDMS) microfluidic chip 506 for the separation of red blood cells infected with the parasite from uninfected red blood cells, the staining of the blood sample which differentially stains infected and uninfected red blood cells, and holds the sample of interest for imaging. When the sample is prepared for imaging, the microfluidic chip 506 is inserted into an optical subsystem 512 that uses two lenses to magnify the image created from transmitted light microscopy. The magnified image is captured with an image capture mechanism (e.g., a camera of a smartphone), and software using a machine learning algorithm assesses whether the sample does or does not contain a malarial infection.

Figure 5B:
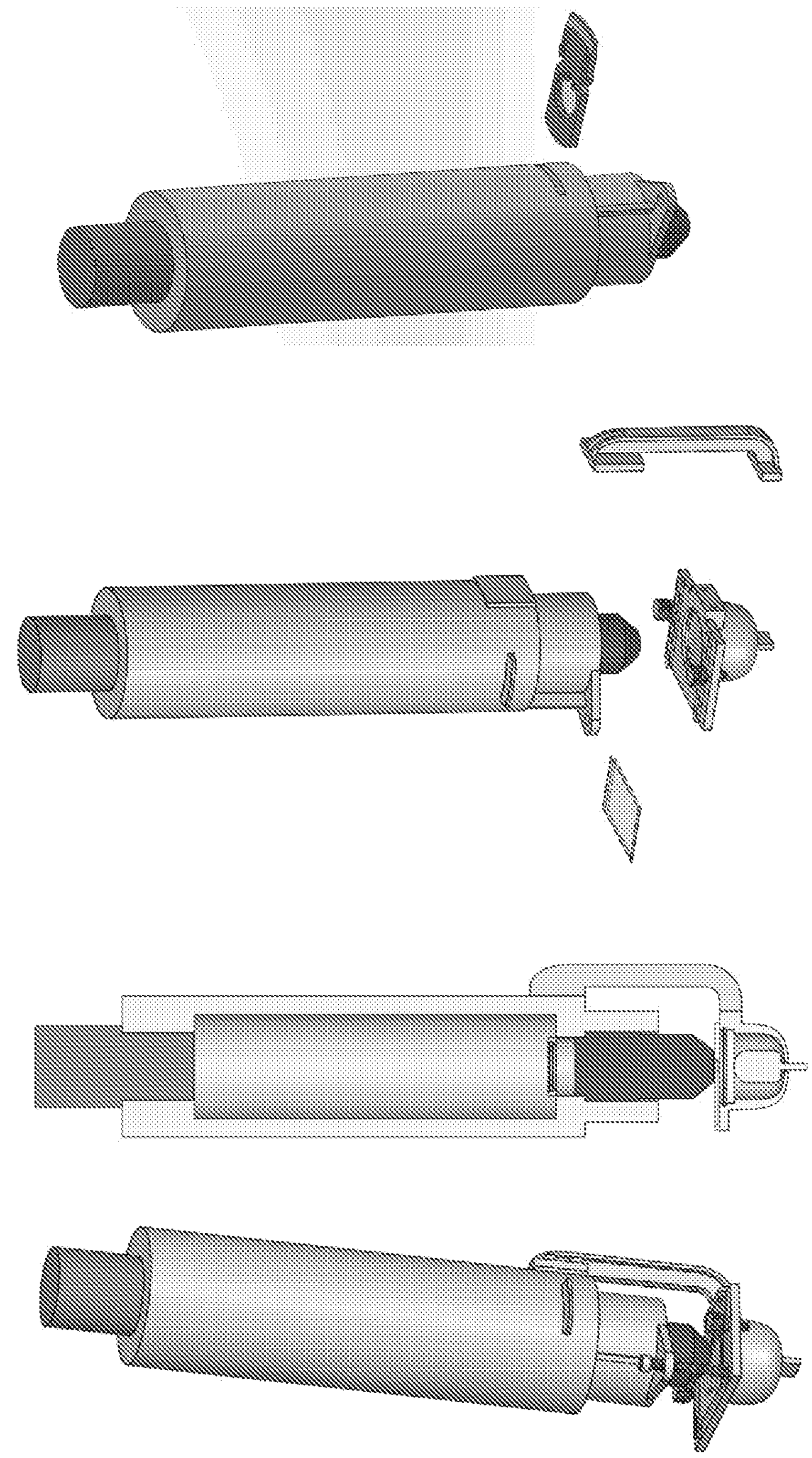
FIG. 5B illustrates various views of an exemplary optical subsystem for use with the embodiment of the apparatus shown in FIG. 5A.

As shown in FIG. 5A, one embodiment of the apparatus 500 comprises an image capture mechanism 502. In one aspect, the image capture mechanism 502 can be camera. The image capture mechanism 502 can take still and/or video images. Generally, the image capture mechanism 502 will be a digital camera, but can be an analog device equipped with or in communication with an appropriate analog/digital converter. The image capture mechanism 502 may also be a webcam, scanner, recorder, or any other device capable of capturing a still image or a video. The apparatus 500 further comprises an optical subsystem 512. The optical subsystem 512 provides magnification of a blood sample on or in a microfluidic chip 506. In various aspects, the optical subsystem 512 can be attached to or work with the image capture mechanism 502, so that magnified images of the blood sample are captured. Also in various aspects, the optical subsystem 512 can be configured for bright field microscopy when stains are employed or can be configured with the insertion of two light-polarizing films for polarized-light microscopy when stains are not used. The first polarizing film intercepts the light before it reaches the blood sample, which will only allow transmission of light with a polarization in one direction. The second polarizing film is oriented orthogonally with respect to the first film, and intercepts light between the sample and the objective lens. In most situations, the orthogonal polarization will obstruct all light from passing through to the objective, however, the hemozoin biocrystal mentioned herein has an established property of birefringence, which changes the polarization of the incident, linearly polarized light. The image received by the lens in this configuration is dark at all points except for where there exists malarial hemozoin. In one non-limiting example, an objective lens of the optical subsystem 512 has a 60× magnification, and the eyepiece of the optical subsystem 512 has a 10× magnification, for a complete system magnification of 600×. As noted above, the optical subsystem 512 works with an image acquisition device 502, which can be a camera of a smartphone, which captures the magnified image. The light source for the device can be a white LED source connected to the optical structure 512. The stage on which the light source and microfluidic chip 506 are located may be held with a compliant C-shaped beam, which allows the distance between the sample and objective to be controlled with the adjustment of a countering fine-adjustment screw. FIG. 5B illustrates various views of the exemplary optical subsystem 512. Specifications of this non-limiting example include 600× (incl. eyepiece) total magnification single objective microscope; DIN standard; removable optical filters, which allow different imaging methods, cross-polarized light, Leishman staining, and DNA fluorescent staining; and a compliant handle that allows for simple micro-adjustment mechanism in achieving focus.

Figure 5C:
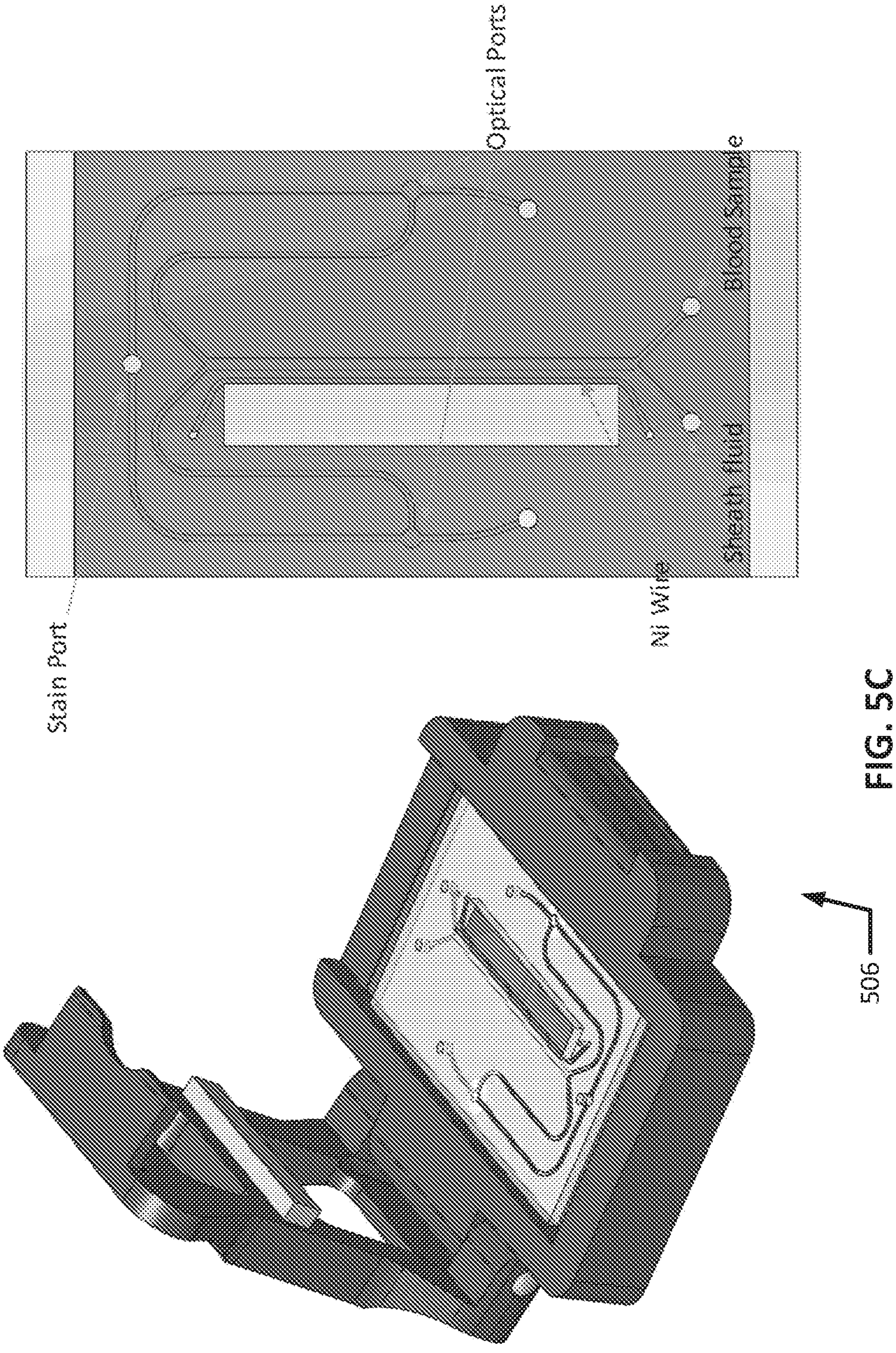
FIG. 5C illustrates an exemplary microfluidic chip for use with the optical subsystem shown in FIG. 5B.

As noted herein, the optical subsystem 512 provides magnification of a blood sample on or in a microfluidic chip 506. FIG. 5C illustrates an exemplary microfluidic chip. Referring to FIG. 5C, when a blood sample enters the chip inlet, a stream of water enters a second chip inlet at approximately the same flow rate. The two inlet streams converge at a "Y junction" where they will not mix and remain adjacent through a straight channel. The water stream is called a "sheath flow" at this point. On the edge of the channel in contact with the sheath flow, an array of magnets are positioned near the wall of the channel. A Nickel wire is positioned between the array of magnets and the channel wall, so that a diverging static magnetic field is created inside the channel, with the field diverging from the sheath flow side to the sample flow side. This diverging magnetic field attracts the parasite's paramagnetic biocrystal, hemozoin, which is produced inside mature PF parasites and is a paramagnetic dipole when subjected to an external magnetic field, to the sheath flow throughout this straight channel. At the end of this magnetophoretic separation stage, the sheath flow with infected red blood cells is diverted from the sample flow at a second "Y channel." The two leaving channels symmetrically flow through circular cavities designed for microscopic imaging and extend further to outlet ports, where the flow will be removed. A separate port has channels diverting symmetrically towards each of the two imaging cavities, where an aqueous stain may be inserted. Staining options include Leishman Stain, Acridine Orange, or no stain. These staining options may require different chip protocols and wait time before imaging. For example, device staining of *Plasmodium* parasites within human red blood cells comprises collecting approximately five microliters of whole blood by sterile finger (or heel) stick and drawn by capillary action into the microfluidic chip 506. As the blood flows into a chamber of the microfluidic chip 506, it mixes with both a preloaded parasite stain and an aqueous diluent/buffer. Following incubation, the microfluidic chip 506 can be inserted into the optical subsystem 512 and imaged using the image capture device 502. In one non-limiting specific example, the stain comprises a blend of azure B (trimethylthionine) and eosin Y (tetrabromofluorescein) in methanol; the diluent comprises phosphate buffered saline (PBS), pH 6.8; the final dilution of RBC sample in stain and diluent is approximately 1:1,000; and the staining protocol is optimized for use at ambient temperatures with an incubation time of five minutes Non-limiting examples of specifications for the microfluidic chip 506 shown in FIG. 5C include a 22×40 mm coverslip; variable channel width (~300 μm) with sheath flow (preliminary), geometric bifurcation, port for stain (preliminary), and Ni wire for magnetic field disruption. The shown PLA staging assembly includes a large ND magnet for integration in chip; two small magnets for cell focusing; and a snap piece. Typically, the microfluidic chip requires a blood sample of less than 50 μL blood draw.

In one aspect, the image capture mechanism 502 is in direct communication with a computing device 510 through, for example, a network (wired (including fiber optic), wireless or a combination of wired and wireless) or a direct-connect cable (e.g., using a universal serial bus (USB) connection, IEEE 1394 "Firewire" connections, and the like). In other aspects, the image capture mechanism 502 can be located remotely from the computing device 510, but capable of capturing an image and storing it on a memory device such that the image can be downloaded or transferred to the computing device 510 using, for example, a portable memory device and the like. In one aspect, the computing device 510 and the image capture mechanism 502 can comprise or be a part of a device such as a smartphone, table, laptop computer or any other mobile computing device.

In a basic configuration, the computing device 510 can be comprised of a processor 504 and a memory 508. The processor 504 can execute computer-readable instructions that are stored in the memory 508. Moreover, images captured by the image capture device 502, whether still images or video, can be stored in the memory 508 and processed by the processor 504 using computer-readable instructions stored in the memory 508.

The processor 504 is in communication with the image capture device 502 and the memory 508. The processor 504 can execute computer-readable instructions stored on the memory 508 to capture, using the image capture device 502, an image of a blood sample on or contained in a microfluidic chip 506, wherein the lens of the image capture device 502 works in concert with the optical subsystem 512 configured to adapt to a smartphone camera so that the captured image is a magnification of the blood sample on or contained in the microfluidic chip 506.

Figure 5D:
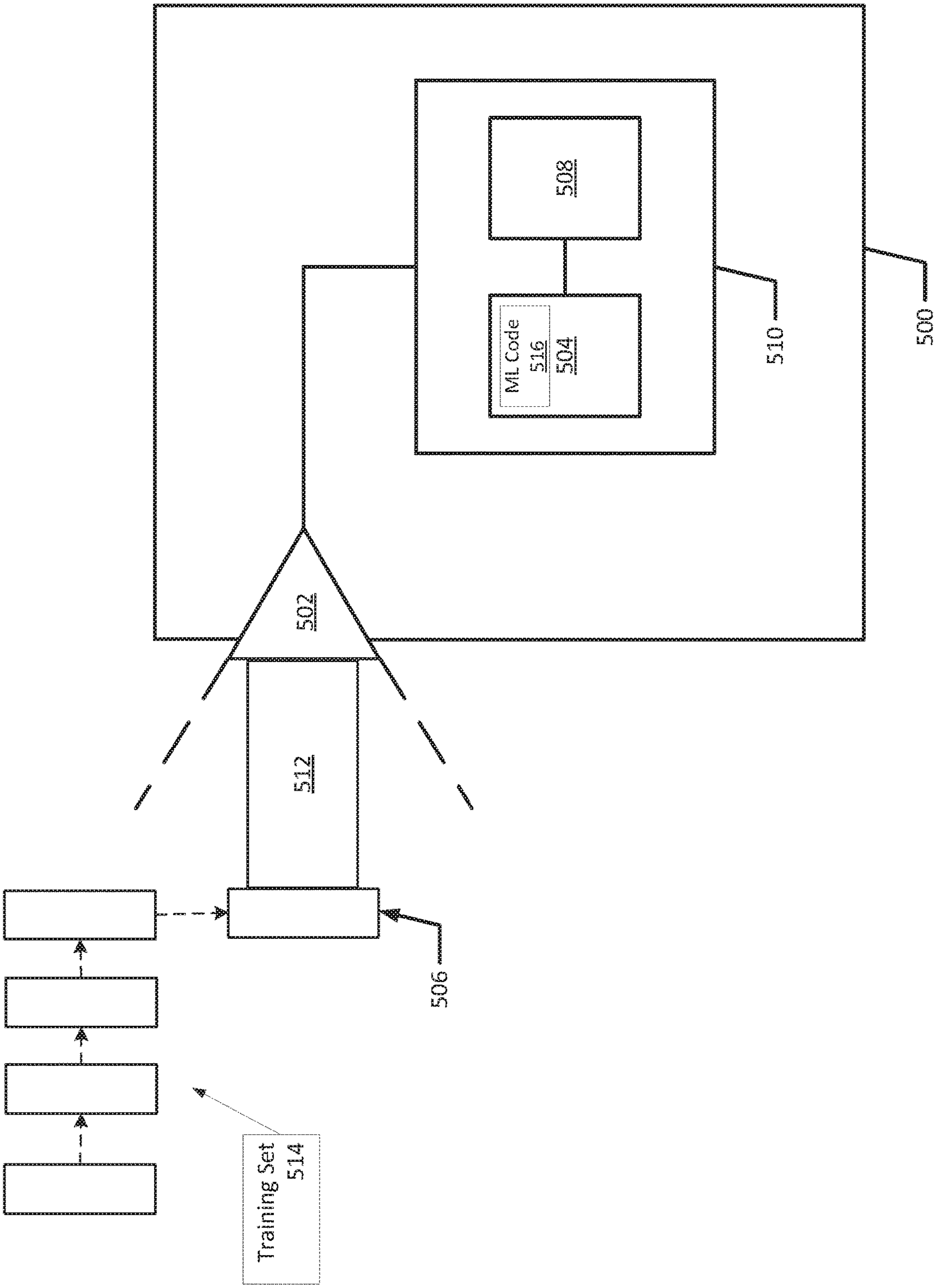
FIG. 5D is an illustration of an embodiment of an apparatus for making a determination whether or not the malaria parasite is detected in a blood sample, wherein the ML code is trained using a training set of blood sample images.

The processor 504 can further execute computer-readable instructions stored on the memory 508 to detect, from the image of the blood sample on or contained in the microfluidic chip 506, the presence or absence of the malaria parasite in the blood sample represented by the blood sample on or contained in the microfluidic chip 506. Generally, the processor 504 of the apparatus 500 executing computer-readable instructions stored in the memory 508 cause the processor 504 to make a determination about the image acquired by the image capture device 502 of the blood sample on or contained in the microfluidic chip 506. As shown in FIG. 5D, the processor 504 executes machine learning (ML) code 516 that has been trained to identify the malaria parasite in the image of the blood sample on or contained in microfluidic chip 506 captured by the image capture device 502. Generally, the executable ML code 516 is stored in the memory 508.

FIG. 5D is an illustration of an apparatus 500 for making a determination whether or not the malaria parasite is detected in a blood sample, wherein the ML code 516 is trained using a training set 514 of blood sample images, such as those shown herein. Initial blood sample images captured with the apparatus 500 are validated with traditional blood-smear microscopy techniques to be labeled "infected" or "uninfected." These images and labels are employed to create the training set 514 for training the ML code 516. In one aspect, the ML code 516 comprises a machine learning "Linear Support Vectors Machine" algorithm and the accuracy of the device is assessed with a separate set of images captured through proper use of the device. The trained and validated machine learning algorithm is tested by assessing unknown blood samples for malaria content and aid diagnosis. In some embodiments, the ML code 516 may comprise a trained convolutional neural network.

Figure 6:
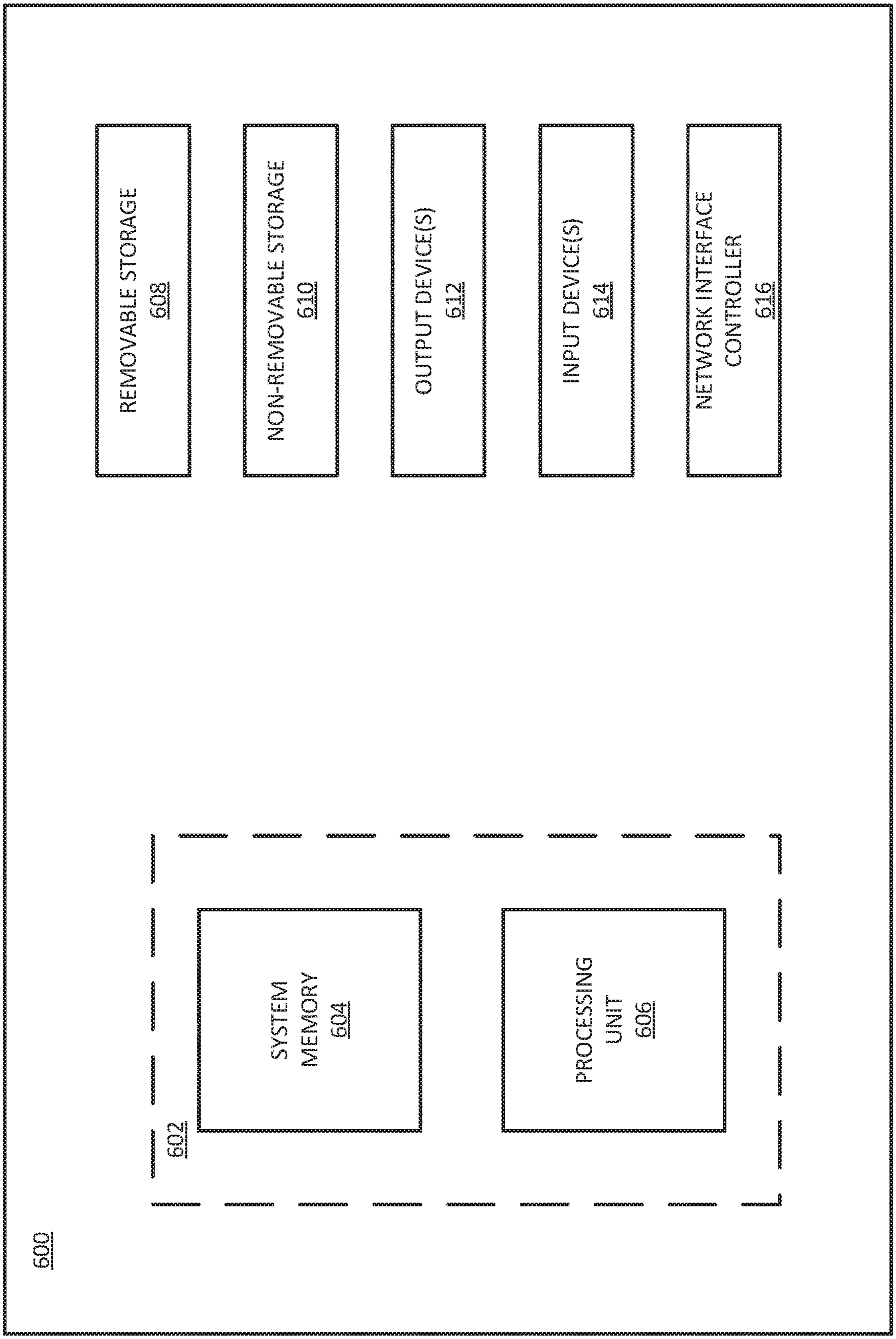
FIG. 6 illustrates an example computing device upon which embodiments of the invention may be implemented.

When the logical operations described herein are implemented in software, the process may execute on any type of computing architecture or platform. Such a computing device 600 as shown in FIG. 6 can be the same as computing device 110, 510, described above, or used alternatively for computing device 110, 510. For example, referring to FIG. 6, an example computing device 600 upon which embodiments of the invention may be implemented is illustrated. The computing device 600 can optionally be a mobile computing device such as a laptop computer, a tablet computer, a smartphone and the like. The computing device 600 may include a bus or other communication mechanism for communicating information among various components of the computing device 600. In its most basic configuration, computing device 600 typically includes at least one processing unit 606 and system memory 604. Depending on the exact configuration and type of computing device, system memory 604 may be volatile (such as random access memory (RAM)), non-volatile (such as read-only memory (ROM), flash memory, etc.), or some combination of the two. This most basic configuration is illustrated in FIG. 6 by dashed line 602. The processing unit 606 may be a standard programmable processor that performs arithmetic and logic operations necessary for operation of the computing device 600.

Computing device 600 may have additional features/functionality. For example, computing device 600 may include additional storage such as removable storage 608 and non-removable storage 610 including, but not limited to, magnetic or optical disks or tapes. Computing device 600 may also contain network connection(s) 616 that allow the device to communicate with other devices. Computing device 600 may also have input device(s) 614 such as a keyboard, mouse, touch screen, etc. Output device(s) 612 such as a display, speakers, printer, etc. may also be included. The additional devices may be connected to the bus in order to facilitate communication of data among the components of the computing device 600. All these devices are well known in the art and need not be discussed at length here.

The processing unit 606 may be configured to execute program code encoded in tangible, computer-readable media. Computer-readable media refers to any media that is capable of providing data that causes the computing device 600 (i.e., a machine) to operate in a particular fashion. Various computer-readable media may be utilized to provide instructions to the processing unit 606 for execution. Common forms of computer-readable media include, for example, magnetic media, optical media, physical media, memory chips or cartridges, or any other non-transitory medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 606 may execute program code stored in the system memory 604. For example, the bus may carry data to the system memory 604, from which the processing unit 606 receives and executes instructions. The data received by the system memory 604 may optionally be stored on the removable storage 608 or the non-removable storage 610 before or after execution by the processing unit 606.

Computing device 600 typically includes a variety of computer-readable media. Computer-readable media can be any available media that can be accessed by device 600 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 604, removable storage 608, and non-removable storage 610 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 600. Any such computer storage media may be part of computing device 600.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

The techniques for making a determination about whether or not a blood sample contains a malaria parasite as described herein can optionally be implemented with a mobile computing device, such as a laptop computer, tablet computer or smartphone. Accordingly, the mobile computing device is extremely small compared to conventional devices and is very portable, which allows the mobile computing device to be used wherever needed.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 7:
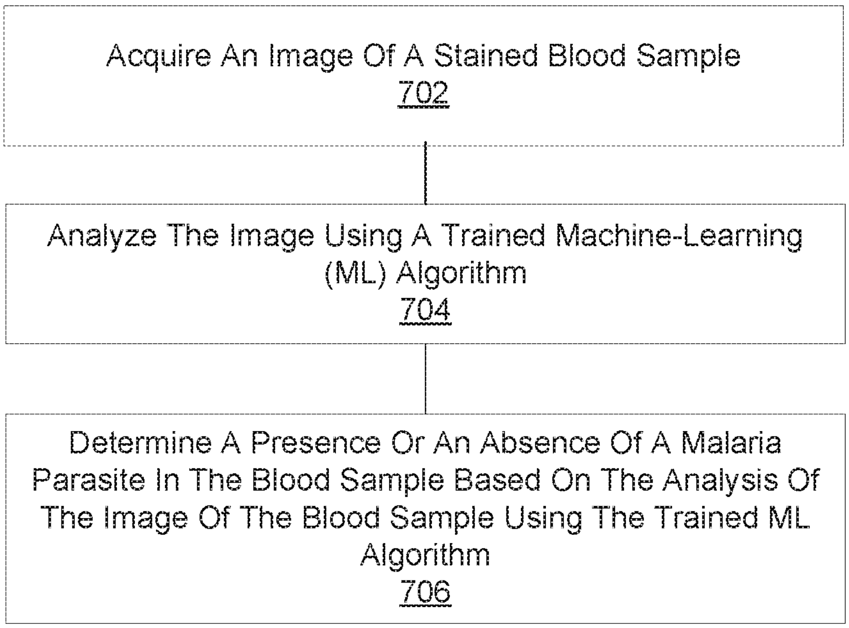
FIGS. 7 and 8 are flowcharts that illustrate example methods for making a determination about a presence or an absence of a malaria parasite in the blood sample based on an analysis of the image of the stained blood sample using a trained ML algorithm.

FIG. 7 illustrates an example method for making a determination about a presence or an absence of a malaria parasite in the blood sample based on an analysis of the image of the blood sample using a trained ML algorithm. At 702, an image of a stained blood sample is acquired using an image acquisition device in communication with a computing device. In some instances, the stained blood sample is magnified using a magnification device when acquiring the image of the stained blood sample. In other instances, the ML algorithm is trained using successively coarser images of a same stained blood sample such that high magnification (e.g. 1000×) of the stained blood sample is not required to determine the presence or absence of a malaria parasite in the blood sample based on the analysis of the image of the stained blood sample using the trained ML algorithm.

At 704, the acquired image of the stained blood sample is analyzed using the trained machine-learning (ML) algorithm executing on the computing device. In some instances, the ML algorithm comprises a neural network. Generally, the ML algorithm is trained using a training set of images, wherein each image of the training set of images is known to be malaria positive or known to be malaria negative.

At, 706, the presence or the absence of a malaria parasite in the blood sample is determined based on the analysis of the image of the stained blood sample using the trained ML algorithm. In some instances, an indication (e.g., visible and/or audible and/or haptic, etc.) is provided by the computing device to indicate the determined presence or absence of the malaria parasite in the blood sample. For example, the user may be informed visually (e.g. green light or red light) or by audio in the local language or dialect that he/she is or is not infected. In some instances, data from the analysis can be securely uploaded to a cloud computing system and melded with existing data sets to (1) continuously re-train the ML code, and (2) to track epidemiological data such as location and number of outbreaks in real-time. Alternatively and/or optionally, the analysis data can be combined with patient data such as gender, age, axillary temperature, hematocrit, case-history, etc. and stored with the analysis data. This additional information is highly desirable to epidemiological studies.

In some instances, the image acquisition device and the computing device comprise parts of a smartphone. In some instances, the smartphone is wirelessly connected to a network for receiving and/or transmitting data. For example, the network may comprise a cloud-based network.

Figure 8:
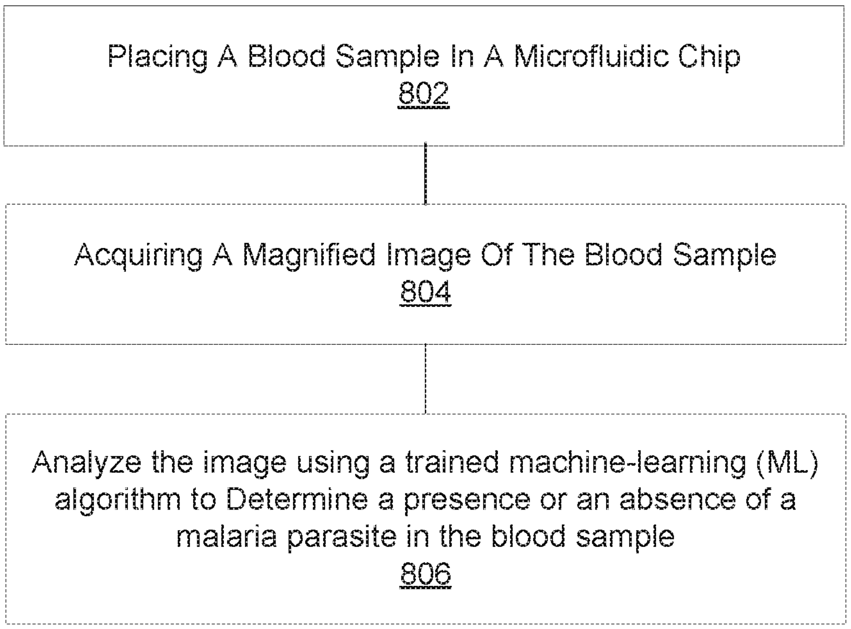

FIG. 8 illustrates an example method for making a determination about a presence or an absence of a malaria parasite in the blood sample based on an analysis of the image using a trained ML algorithm. At 802, a blood sample is placed in a microfluidic chip, wherein the microfluidic chip concentrates red blood cells infected with a parasite (e.g., *Plasmodium* parasites) from uninfected red blood cells, stains the blood sample by selectively staining infected red blood cells, and holds the blood sample for imaging. At 804, an image of the stained blood sample in the microfluidic chip is acquired using an optical subsystem and an image acquisition device in communication with a computing device, wherein the optical subsystem magnifies the stained blood sample such that the acquired image is of the magnified blood sample. In some instances, wherein the microfluidic chip is inserted into the optical subsystem. In some instances, the optical subsystem uses two lenses to magnify the image of the stained blood sample created from transmitted light microscopy. In some instances, the image acquisition device comprises a camera of a smartphone. At 806, the magnified image is analyzed using a trained machine-learning (ML) algorithm executing on the computing device, to assess whether the sample does or does not contain a malarial infection. In some instances, an indication of the determined presence or absence of the malaria parasite in the blood sample is provided (e.g., visible and/or audible and/or haptic, etc.). In some instances, the ML algorithm comprises a neural network.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus comprised of:

a microfluidic chip;

an image capture device;

a memory; and a processor in communication with the memory and the image capture device, wherein the processor executes computer-readable instructions comprising a trained machine-learning (ML) algorithm stored in the memory that cause the processor to;

capture, using the image capture device, an image of a stained blood sample;

analyze, using the trained ML algorithm, the image of the stained blood sample; and determine a presence or an absence of a malaria parasite in the blood sample based on the analysis of the image of the stained blood sample using the trained ML algorithm, wherein the microfluidic chip, preloaded with a shelf-stable stain in a reservoir on the chip, receives a blood sample, selectively stains red blood cells in the blood sample infected with the malaria parasite using the preloaded shelf-stable stain to create the stained blood sample, and holds the stained blood sample in one or more circular cavities designed for microscopic imaging for capturing the image of the stained blood sample on or in the microfluidic chip.

2. The apparatus of claim 1, further comprising computer-readable instructions comprising the trained ML algorithm stored in the memory that cause the processor to provide an indication of the determined presence or absence of the malaria parasite in the blood sample.

3. The apparatus of claim 1, wherein the apparatus comprises a smartphone wirelessly connected to a network for receiving and/or transmitting data.

4. The apparatus of claim 3, wherein the network comprises a cloud-based network.

5. The apparatus of claim 1, wherein the ML algorithm comprises a trained neural network, trained using a training set of images, wherein each image of the training set of images is known to be malaria positive or known to be malaria negative.

6. The apparatus of claim 1, further comprising a magnification device, wherein the stained blood sample is magnified by the magnification device when acquiring the image of the stained blood sample.

7. The apparatus of claim 5, wherein the ML algorithm is trained using successively coarser images of a same stained blood sample such that magnification of the stained blood sample is not required to determine the presence or absence of a malaria parasite in Filed Nov. 29, 2021 the blood sample based on the analysis of the image of the stained blood sample using the trained ML algorithm.

8. The apparatus of claim 1, wherein the microfluidic chip further separates red blood cells infected with the malaria parasite from uninfected red blood cells in the blood sample, wherein a stream of unstained blood sample is introduced into a first chip inlet of the microfluidic chip and a single stream of aqueous buffer solution enters a second chip inlet of the microfluidic chip at approximately a same flow rate as the unstained blood sample introduced into the first chip inlet, wherein the stream of unstained blood sample and the stream of aqueous buffer solution converge at a first Y junction where they do not mix and remain adjacent through a straight channel, said stream of aqueous buffer solution proximate a first side of the straight channel and said stream of unstained blood sample proximate a second side of the straight channel, and wherein an array of magnets are positioned near the first side of the straight channel proximate the stream of aqueous buffer solution and a wire is positioned between the array of magnets and a channel wall so that a diverging magnetic field is created inside the straight channel, with the diverging magnetic field diverging from the first side of the straight channel proximate the stream of aqueous buffer solution to the second side of the straight channel proximate the stream of unstained blood sample, wherein the diverging magnetic field attracts the malaria parasite in the stream of unstained blood sample and causes red blood cells infected with the malaria parasite in the stream of unstained blood sample to move from the stream of unstained blood sample to the stream of aqueous buffer solution, wherein the stream of aqueous buffer solution with the red blood cells infected with the malaria parasite is diverted from the stream of unstained blood sample at a second Y junction and are stained using the shelf-stable preloaded stain to create the stained blood sample, wherein the stained blood sample with the infected red blood cells and the stream of unstained blood sample each flow from the second Y junction through the one or more circular imaging cavities designed for microscopic imaging, wherein at least one of the circular imaging cavities holds the stained blood sample on or in the microfluidic chip for the imaging.

9. The apparatus of claim 1, wherein acquiring the image of the stained blood sample on or in the microfluidic chip comprises using an optical subsystem in communication with the processor, wherein the optical subsystem magnifies the stained blood sample such that the acquired image is of the magnified blood sample.

10. The apparatus of claim 9, wherein the microfluidic chip is inserted into the optical subsystem.

11. The apparatus of claim 9, wherein the optical subsystem uses two lenses to magnify the image of the stained blood sample created from transmitted light microscopy when acquiring the image of the stained blood sample on or in the microfluidic chip.

12. The apparatus of claim 3, wherein the image capture device comprises a camera of the smartphone.

13. The apparatus of claim 1, wherein the preloaded shelf-stable stain comprises a blend of azure B (trimethylthionine) and eosin Y (tetrabromofluorescein) in methanol.

14. The apparatus of claim 1, wherein the microfluidic chip is preloaded with the shelf-stable stain and an aqueous diluent/buffer, wherein the preloaded shelf-stable stain comprise a blend of azure B (trimethylthionine) and eosin Y (tetrabromofluorescein) in methanol; and the aqueous diluent/buffer comprises phosphate buffered saline (PBS), pH 6.8 such that the stained blood sample comprises a final dilution of red blood cells infected with the malaria parasite in stain and diluent is approximately 1:1,000; and the staining protocol is optimized for use at ambient temperatures with an incubation time of five minutes.

15. The apparatus of claim 8, wherein the microfluidic chip further comprises a staining port, said staining port having channels diverting symmetrically towards each of the separate circular imaging cavities, where an aqueous stain may be inserted.

* * * * *